(12) United States Patent
Schramm

(10) Patent No.: US 8,541,567 B2
(45) Date of Patent: Sep. 24, 2013

(54) TRANSITION STATE STRUCTURE OF 5'-METHYLTHIOADENOSINE/S-ADENOSYLHOMOCYSTEINE NUCLEOSIDASES

(75) Inventor: Vern L. Schramm, New Rochelle, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 593 days.

(21) Appl. No.: 11/988,651

(22) PCT Filed: Jul. 26, 2006

(86) PCT No.: PCT/US2006/029289
§ 371 (c)(1), (2), (4) Date: Nov. 26, 2008

(87) PCT Pub. No.: WO2007/016291
PCT Pub. Date: Feb. 8, 2007

(65) Prior Publication Data
US 2011/0086812 A1    Apr. 14, 2011

Related U.S. Application Data

(60) Provisional application No. 60/702,893, filed on Jul. 27, 2005.

(51) Int. Cl.
   *C07H 21/04* (2006.01)
(52) U.S. Cl.
   USPC ....... 536/24.5; 536/23.1; 536/23.2; 536/24.1; 536/24.3; 536/124
(58) Field of Classification Search
   None
   See application file for complete search history.

(56) References Cited

U.S. PATENT DOCUMENTS

| | | | |
|---|---|---|---|
| 5,985,848 A | 11/1999 | Furneaux et al. | |
| 6,066,722 A | 5/2000 | Furneaux et al. | |
| 6,121,296 A | 9/2000 | Schramm et al. | |
| 6,228,847 B1 | 5/2001 | Furneaux et al. | |
| 6,379,911 B2 | 4/2002 | Schramm et al. | |
| 6,458,799 B1 | 10/2002 | Montgomery et al. | |
| 6,492,347 B2 | 12/2002 | Furneaux et al. | |
| 6,693,193 B1 | 2/2004 | Furneaux et al. | |
| 6,764,829 B2 | 7/2004 | Schramm et al. | |
| 6,803,455 B2 | 10/2004 | Furneaux et al. | |
| 7,022,852 B2 | 4/2006 | Furneaux et al. | |
| 7,098,334 B2 | 8/2006 | Furneaux et al. | |
| 7,109,331 B2 | 9/2006 | Furneaux et al. | |
| 7,211,653 B2 | 5/2007 | Furneaux et al. | |
| 7,211,677 B2 | 5/2007 | Furneaux et al. | |
| 7,390,890 B2 | 6/2008 | Furneaux et al. | |
| 7,405,297 B2 | 7/2008 | Furneaux et al. | |
| 7,553,839 B2 | 6/2009 | Evans et al. | |
| 7,655,795 B2 | 2/2010 | Evans et al. | |
| 7,777,025 B2 | 8/2010 | Schramm et al. | |
| 2004/0110772 A1 | 6/2004 | Furneaux et al. | |
| 2006/0041013 A1 | 2/2006 | Brittain et al. | |
| 2006/0160765 A1 | 7/2006 | Evans et al. | |
| 2006/0217551 A1 | 9/2006 | Evans et al. | |
| 2007/0015772 A1 | 1/2007 | Furneaux et al. | |
| 2007/0275988 A1 | 11/2007 | Schramm | |
| 2008/0280334 A1 | 11/2008 | Lenz et al. | |
| 2009/0012104 A1 | 1/2009 | Babu et al. | |
| 2009/0233948 A1 | 9/2009 | Evans et al. | |
| 2009/0239885 A1 | 9/2009 | Evans et al. | |
| 2009/0325986 A1 | 12/2009 | Furneaux et al. | |
| 2010/0062995 A1 | 3/2010 | Schramm | |
| 2010/0168141 A1 | 7/2010 | Evans et al. | |
| 2010/0222370 A1 | 9/2010 | Schramm et al. | |
| 2011/0046167 A1 | 2/2011 | Clinch et al. | |
| 2011/0092521 A1 | 4/2011 | Furneaux et al. | |
| 2011/0130412 A1 | 6/2011 | Clinch et al. | |
| 2011/0190265 A1 | 8/2011 | Schramm | |
| 2012/0157479 A1 | 6/2012 | Evans et al. | |

FOREIGN PATENT DOCUMENTS

| | | |
|---|---|---|
| WO | WO 03/080620 A | 10/2003 |
| WO | WO 2006/123953 | 11/2006 |
| WO | WO 2007/069923 | 6/2007 |
| WO | WO 2007/097647 | 8/2007 |
| WO | WO 2007/097648 | 8/2007 |
| WO | WO 2008/030118 | 3/2008 |
| WO | WO 2008/030119 | 3/2008 |
| WO | WO 2008/039324 A1 | 4/2008 |
| WO | WO 2008/079028 | 7/2008 |

OTHER PUBLICATIONS

Bagdassarian C K et al., entitled "Molecular electrostatic potential analysis for enzymatic substrates, competitive inhibitors and transition-state inhibitors," J. Am. Chem. Soc., 1996, V118, pp. 8825-8836.

Singh V et al., entitled "Femtomolar transition state analogue inhibitors of 5'-Methylthioadenosine/S-Adenosylhomocysteine Nucleosidase from *Escherichia coli.*," J Biol Chem.May 6, 2005;280(18):18265-73. Epub Mar. 4, 2005.

Lee J E et al., entitled "Structural comparison of MTA phosphorylase and MTA/AdoHcy nucleosidase explains substrate preferences and identifies regions exploitable for inhibitor design," Biochemistry, May 11, 2004, V43 (18) 5159-69, abstract only.

(Continued)

*Primary Examiner* — Patrick Lewis

(74) *Attorney, Agent, or Firm* — Amster, Rothstein & Ebenstein LLP

(57) ABSTRACT

Provided are methods of designing a putative inhibitor of a 5'-methylthioadenosine/S-adenosylhomocysteine nucleosidase. The methods comprise designing a chemically stable compound that resembles the charge and geometry of the 5'-methylthioadenosine/S-adenosylhomocysteine nucleosidase transition state. Also provided are methods of inhibiting 5'-methylthioadenosine/S-adenosylhomocysteine nucleosidases using the inhibitors found by the above methods.

20 Claims, 29 Drawing Sheets

(56) References Cited

OTHER PUBLICATIONS

Lee J et al., entitled "Structural rationale for the affinity of pico-and femtomolar transition state analogues of *Escherichia coli* 5'-Methylthioadenosine/S-Adenosylhomocysteine Nucleosidase," The Journal of Biological Chemistry, vol. 280, No. 18, Issue May 6, pp. 18274-18282, 2005.

Evans G B et al., entitled "Synthesis of second-generation transition state analogues of human purine nucleoside phosphorylase," Journal of Medicinal Chemistry, vol. 46, No. 24, Nov. 20, 2003, 5271-5276.

Supplementary Partial European Search Report, issued by the European Patent Office on Jan. 13, 2009 in connection with European Patent Aplication No. 06788712.5.

Schramm, V L, entitled "Enzymatic transition states: thermodynamics, dynamics and analogue design," Archives of Biochemistry and Biophysics, 2005, vol. 433, No. 1, pp. 13-26.

Singh V et al., entitled "Picomolar Transition State Analogue Inhibitors of Human 5'-Methylthioadenosine Phosphorylase and X-ray Structure with MT-Immucillin -A,"Biochemistry, 2004, vol. 43, No. 1, pp. 9-18.

Schramm V L, entitled "Enzymatic Transition States and Transition State Analog Design," Annu. Rev. Biochem. 1998, 67:693-720.

USPTO Office Action dated May 2, 2012 in connection with U.S. Appl. No. 12/311,091.

Singh V et al., entitled Structure and Inhibition of a Quorum Sensing Target from *Streptococcus pneumoniae,* Biochemistry, Oct. 31, 2006; 45(43): 12929-12941.

Singh V et al., entitled "Transition state structure of 5'-methylthioadenosine/S-adenosylhomocysteine nucleosidase from *Escherichia coli* and its similarity to transition state analogues," Biochemistry, Sep. 6, 2005;44(35):11647-59.

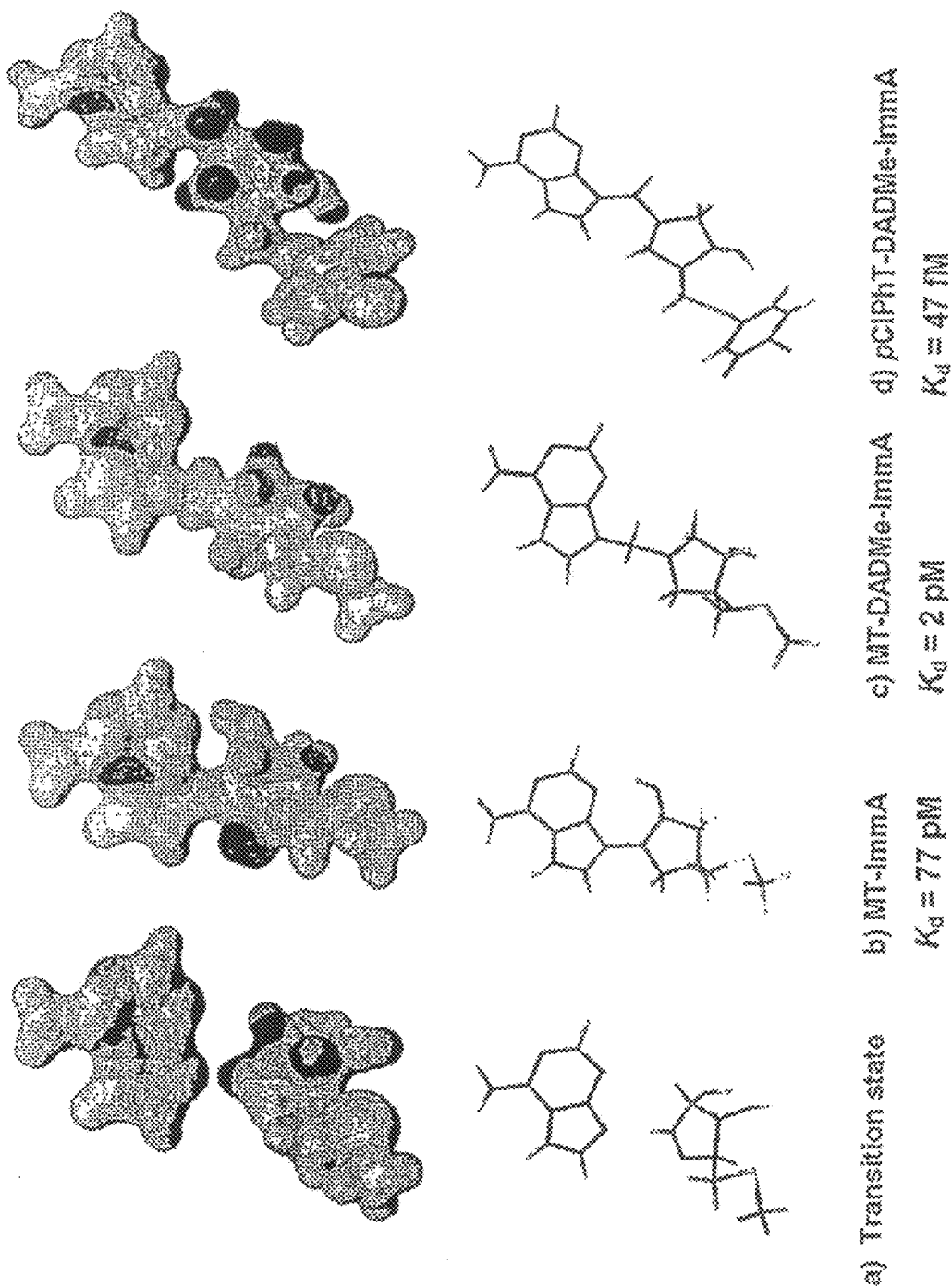
FIG. 6 (A-D)

FIG. 6 (continued)
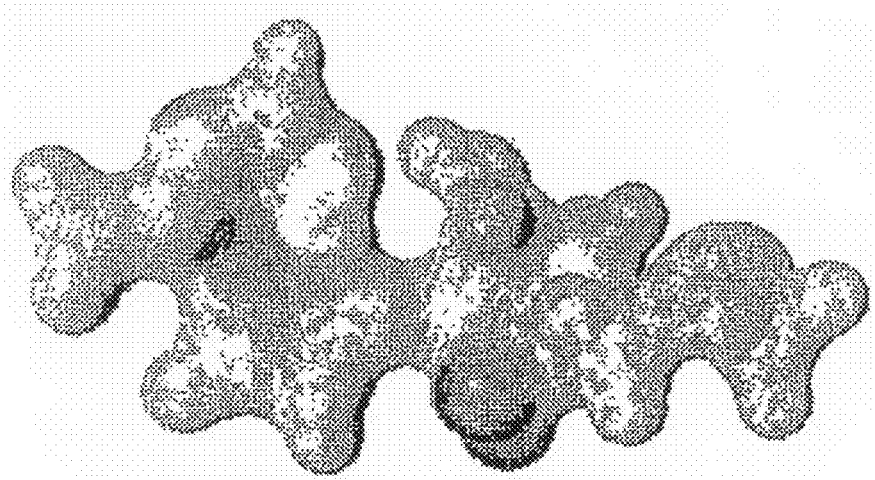
Transition state analogue
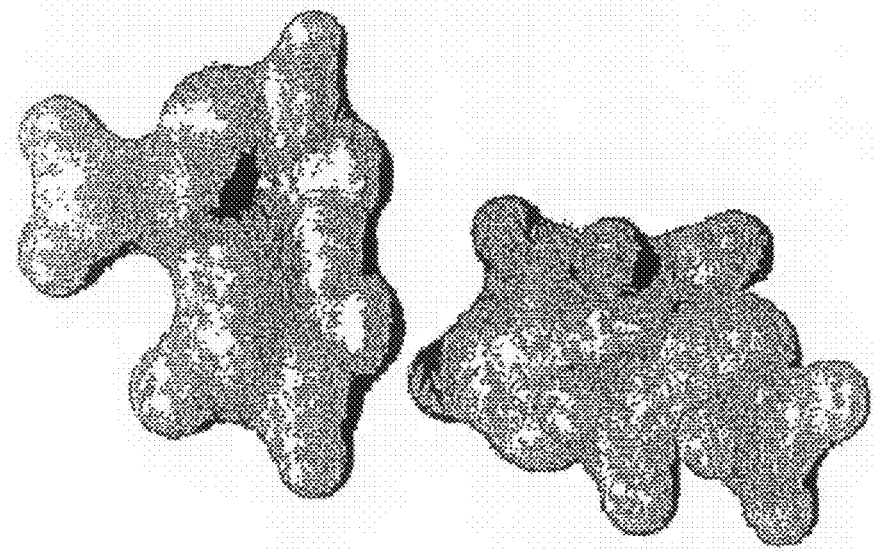
MTAN transition state FIG. 9
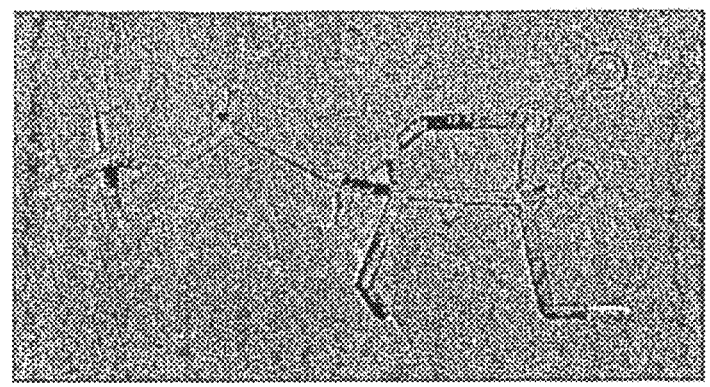
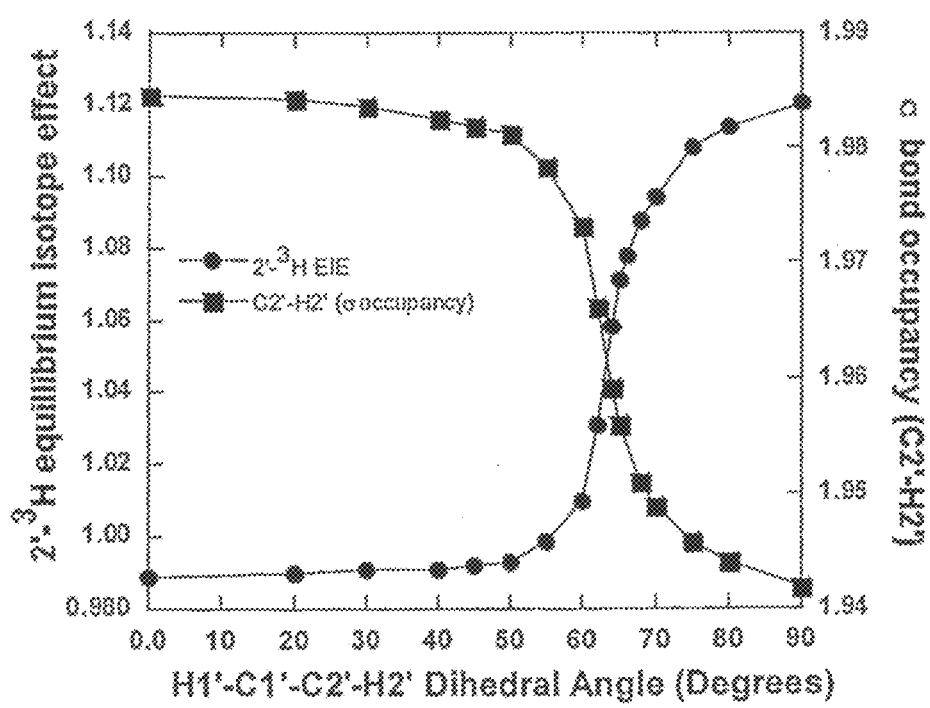

FIG. 10
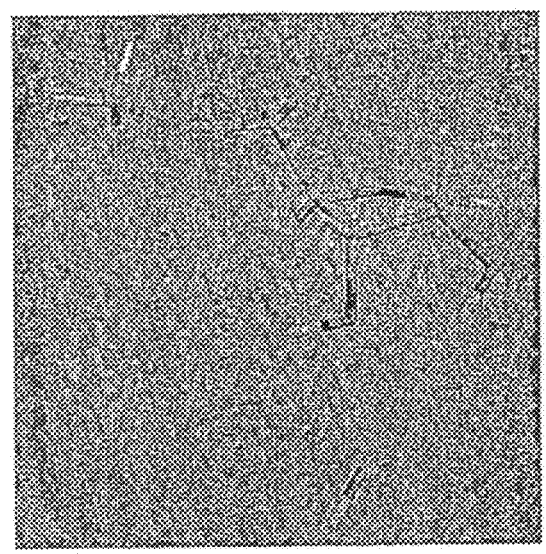
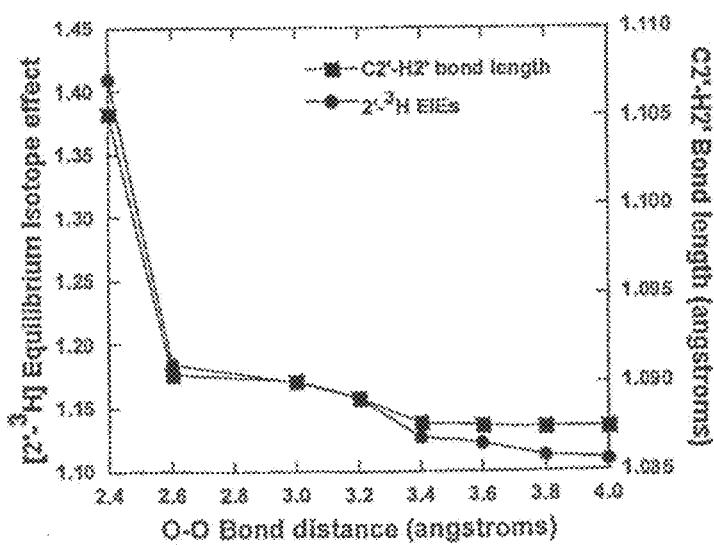

FIG. 12
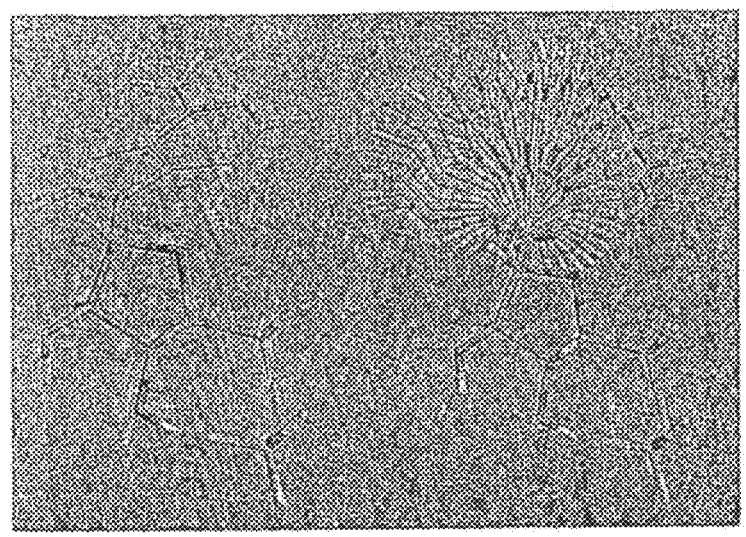
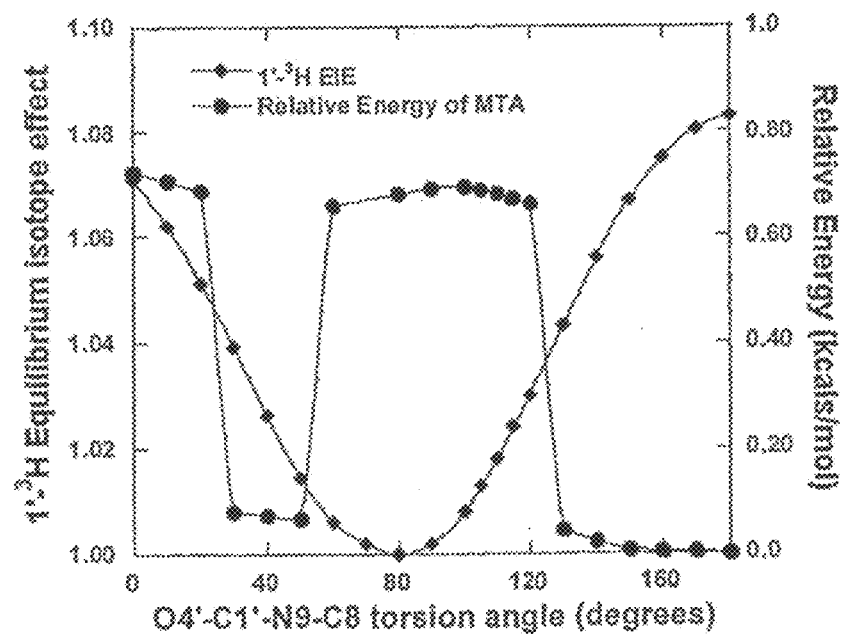

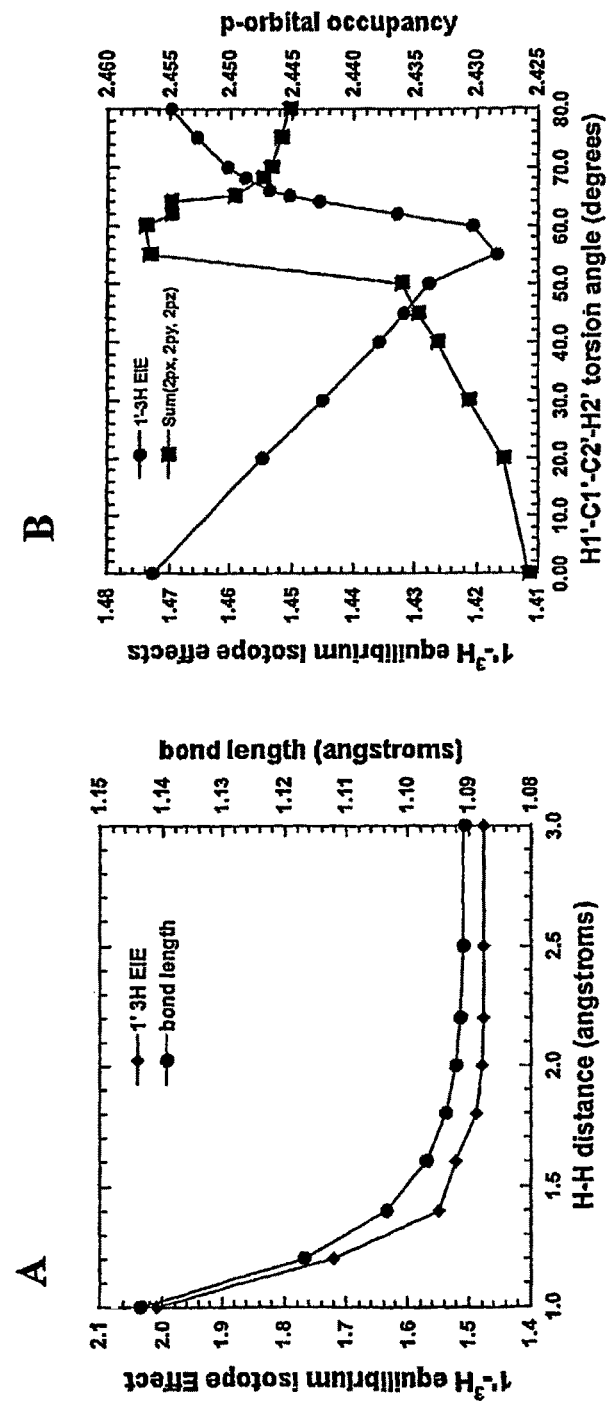
FIG. 13 (A-B)

FIG. 13 (C-D)
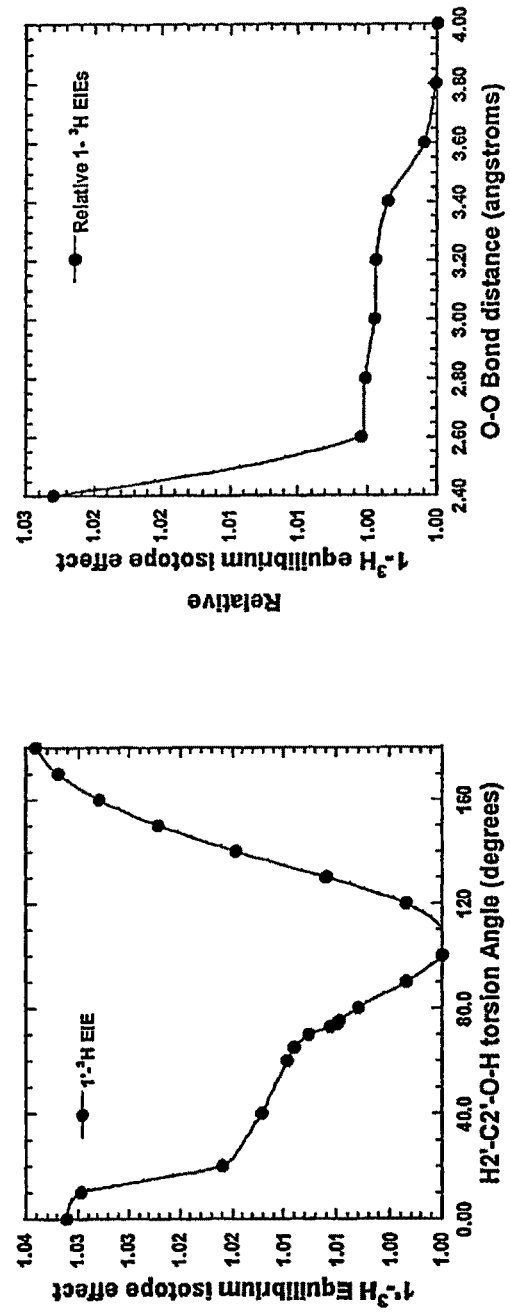

FIG. 14
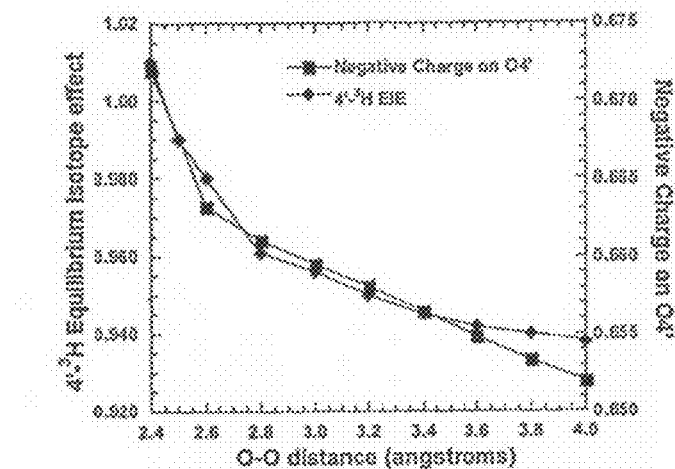
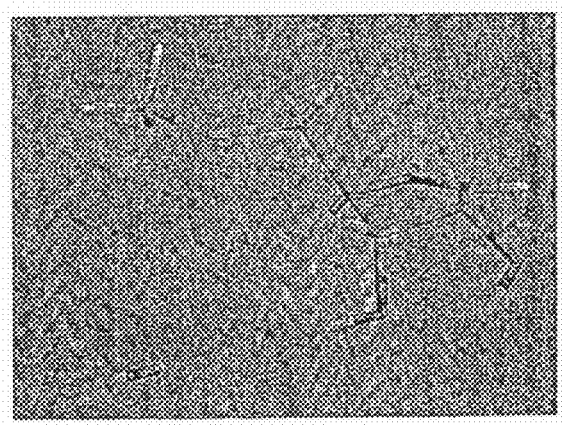
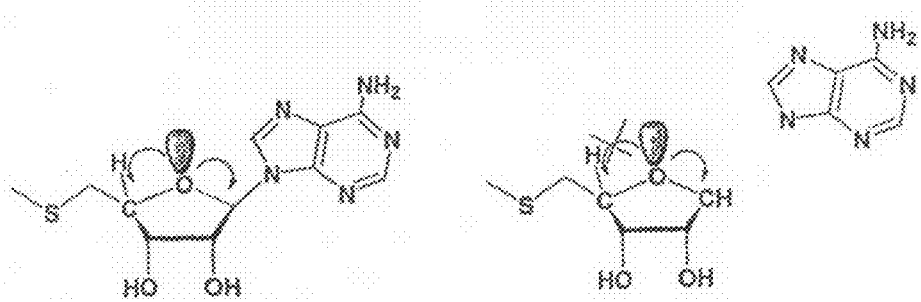
Substrate          Transition State FIG. 15
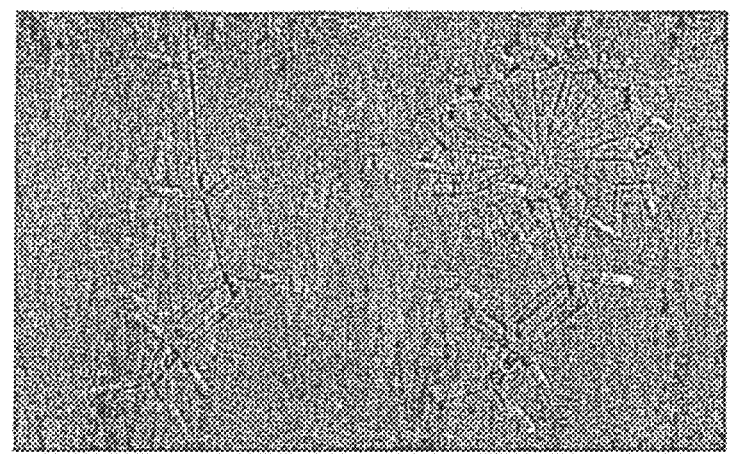
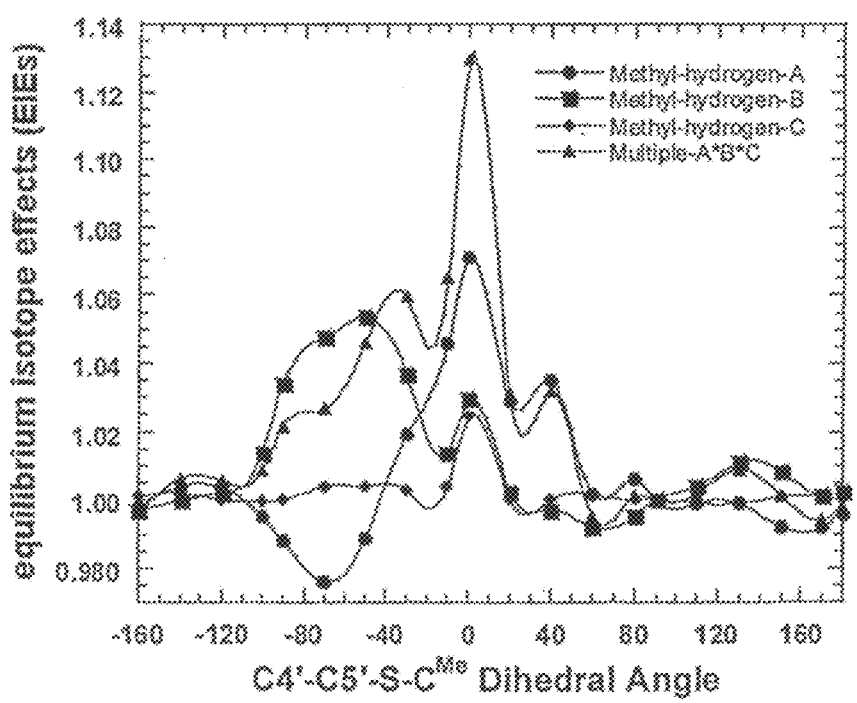

FIG. 19
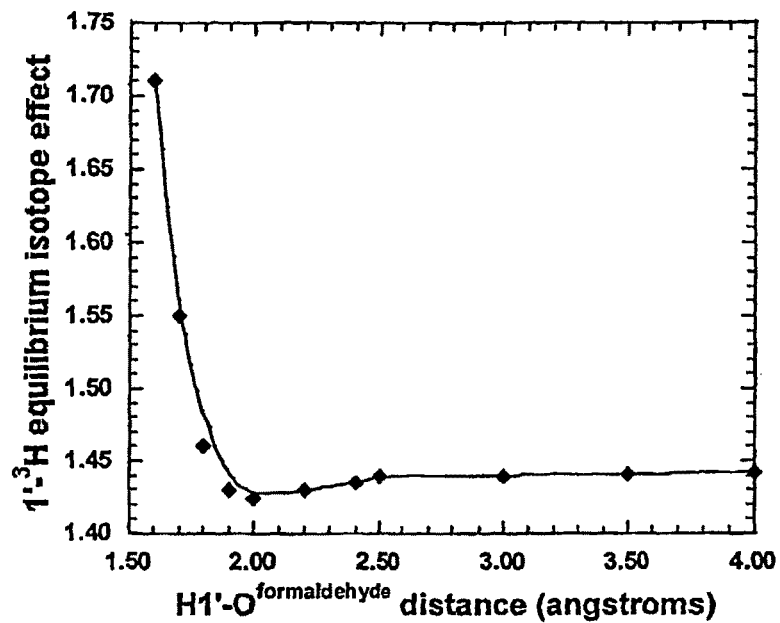
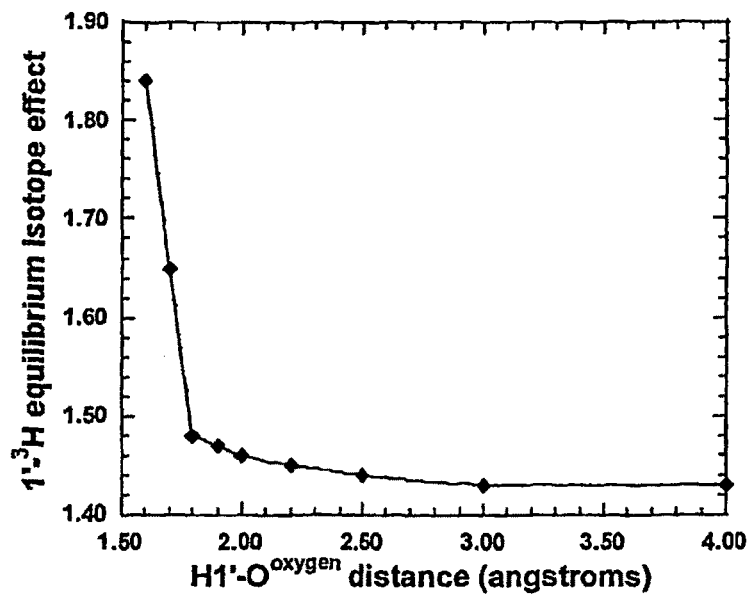

FIG. 21
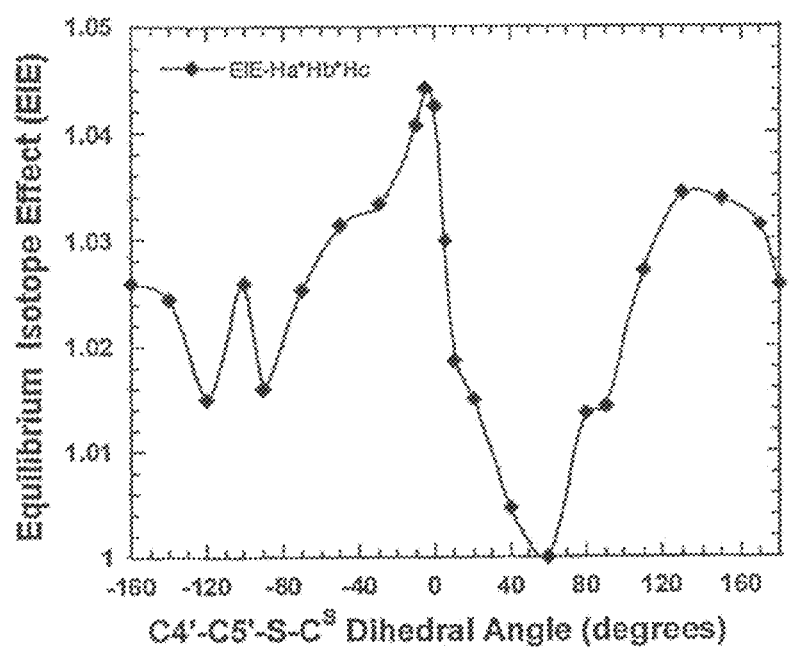
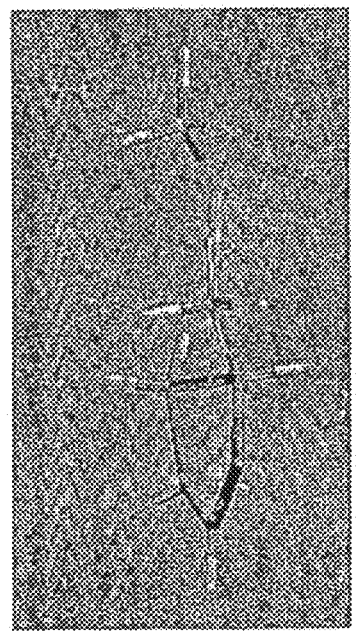

TRANSITION STATE STRUCTURE OF 5'-METHYLTHIOADENOSINE/S-ADENOSYLHOMOCYSTEINE NUCLEOSIDASES

CROSS-REFERENCE TO RELATED APPLICATION

This application is a national stage entry under 35 U.S.C. §371 of PCT International Patent Application No. PCT/US2006/029289, filed on Jul. 26, 2006, which claims priority to U.S. Provisional Patent Application No. 60/702,893, filed on Jul. 27, 2005, the contents of which are hereby incorporated by reference.

STATEMENT OF GOVERNMENT SUPPORT

This invention was made with government support under Grant No. GM41916 awarded by The National Institutes of Health. The government has certain rights in the invention.

BACKGROUND OF THE INVENTION (1) Field of the Invention

The present invention generally relates to enzyme inhibitors. More specifically, the invention relates to methods of designing transition state inhibitors of a 5'-methylthioadenosine/S-adenosylhomocysteine nucleosidase (2) Description of the Related Art References cited Allart, B., Gatel, M., Guillerm, D., and Guillerm, G. (1998) The catalytic mechanism of adenosylhomocysteine/methylthioadenosine nucleosidase from *Escherichia coli*—chemical evidence for a transition state with a substantial oxocarbenium character. *Eur. J. Biochem.* 256, 155-162.

Anet, F. A. L.; Basus, V. J.; Hewett, A. P. W.; Saunders, M. (1980) *J. Am. Chem. Soc.* 102, 3945-3946.

Anisimov, V., and Paneth, P. (1999) ISOEFF98. A program for studies of isotope effects using Hessian modifications, *J. Math. Chem.* 26, 75-86.

Bagdassarian, C. K., Schramm, V. L., and Schwartz, S. D. (1996) Molecular electrostatic potential analysis for enzymatic substrates, competitive inhibitors and transition-state inhibitors, *J. Am. Chem. Soc.* 118, 8825-8836.

Becke, D. A. (1996) Density-functional thermochemistry. IV. A new dynamical correlation functional and implications for exact-exchange mixing *J. Chem. Phys.* 104, 1040-1046.

Bennet, A. J.; Sinnot, M. L. (1986) *J. Am. Chem. Soc.* 108, 7287-7294

Berti, P. J., and Tanaka K. S. E. (2002) Transition state analysis using multiple kinetic isotope effects: Mechanisms of enzymatic and non-enzymatiC glycoside hydrolysis and transfer. *Adv. Phys. Org. Chem.* 37, 239-314.

Birck, M., and Schramm, V. L., (2004a) Nucleophilic participation in the transition state for human thymidine phosphorylase. *J. Am. Chem. Soc.* 126, 2447-2453.

Birck, M. R., and Schramm, V. L. (2004b) Binding Causes the remote [5'-$^3$H]thymidine kinetic isotope effect in human thymidine phosphorylase, *J. Am. Chem. Soc.* 126, 6882-6883.

Cadieux, N.; Bradbeer, C.; Reeger-Schneider, E.; Koster, W.; Mohanty, A. K.; Wiener, M. C.; Kadner, R. J. (2002) *J. Bacteriol.* 184, 706-717.

Carteni-Farina, M., Porcelli, M., Cacciapuoti, G., Zappia, V., Grieko, M., and Difiore P. P. (1983) *Adv. Polyamine Res.* 4, 779-792.

Cha, Y.; Murray, C. J.; Klinman, J. P. (1989) *Science* 243, 1325-1330.

Chen, X. Y., Berti, P. J., and Schramm, V. L. (2000) Ricin A-Chain: Kinetic Isotope Effects and Transition State Structures with Stem-Loop RNA, *J. Am. Chem. Soc.* 122, 1609-1617.

Chen, X., Schauder, S., Potier, N., Dorsselaer, V. A., Pelczer, I., Bassler, B. L., and Hughson, F. M. (2002) Structural identification of a bacterial quorum-sensing signal containing boron, *Nature* 415, 545-549.

Cleland, W. W. (2005) *Arch. Biochem. Biophy.* 433, 2-12.

Cornell, K. A., Swarts, W. E., Barry, R. D., and/Riscoe, M. K. (1996) Characterization of recombinant *Eschericha coli* 5'-methylthioadenosine/S-adenosylhomocysteine nucleosidase: analysis of enzymatic activity and substrate specificity, *Biochem. Biophys. Res. Commun.* 228, 724-732.

Craig, B. N.; Janssen, M. U.; Wickersham, B. M.; Rabb, D. M.; Chang, P. S.; O'Leary, D. J. (1996) *J. Org. Chem.* 61, 9610-9613.

Cramer, C. J.; Truhlar, D. J. (1999) *Chem. Rev.* 99, 2161-2200.

DeWolf, W. E., Jr., Fullin, F. A., and Schramm, V. L. (1979) The catalytic site of AMP nucleosidase. Substrate specificity and pH effects with AMP and formycin 5'-PO$_4$, *J. Biol. Chem.* 254, 10868-10875.

Dwyer, J. J.; Gittis, A. G.; Karp, D. A.; Lattman, E. E.; Spencer, D. S.; Stities, W. E.; Garcia-Moreno, B. E. (2000) *Biophysical Journal* 79, 1610-1620.

Flükiger, P., Lüthi, H. P., Portmann, S., and Weber, J. (2000) *MOLEKEL* 4.0, Swiss Center for Scientific Computing, Manno, Switzerland.

Frisch, M. J., G. W. Trucks, H. B. Schlegel, G. E. Scuseria, M. A. Robb, J. R. Cheeseman, J. A. Montgomery, Jr., T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. ada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. mDannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, C. Gonzalez, and J. A. Pople, Gaussian 03, Revision B.04, Gaussian, Inc., Pittsburgh Pa., 2003.

Gambogi, J. E.; L'Esperance, R. P.; Lehmann, K. K.; Pate, B. H.; Scoles, G. (1993) *J. Chem. Phys.* 98, 1116-1122.

Heys, J. R. (1987) *J. Chromatogr.* 407, 37-47.

Hibasami, H., Borchardt, R. T., Chen, S. Y., Coward, J. K., and Pegg A. E. (1980) Studies of inhibition of rat spermidine synthase and spermine synthase, *Biochem. J.* 187, 419-428.

Horenstein, B. A., and Schramm, V. L. (1993) Correlation of the molecular electrostatic potential surface of an enzymatic transition state with novel transition-state inhibitors, *Biochemistry* 32, 9917-9925.

Kline, P. C., and Schramm, V. L. (1993) Purine nucleoside phosphorylase. Catalytic mechanism and transition-state analysis of the arsenolysis reaction, *Biochemistry* 32, 13212-13219.

Lee, J. E., Cornell, K. A., Riscoe, M. K., and Howell, P. L. (2001) Expression, purification, crystallization and preliminary X-ray analysis of *Escherichia coli* 5'-methylthioadenosine/S-adenosylhomocysteine nucleosidase, *Acta Crystallogr. D. Biol. Cyystallogr.* 57, 150-152.

Lee, J. E., Cornell, K. A., Riscoe, M. K., and Howell, P. L. (2003) Structure of *Escherichia coli* 5'-methylthioadenosine/S-adenosylhomocystein nucleosidase inhibitor complexes provide insight into the conformational changes required for substrate binding and catalysis. *J. Biol. Chem.* 280, 8761-8770.

Lee, J. E., Singh, V., Evans, G. B., Tyler, P. C., Furneaux, R. H., Cornell, K. A., Riscoe, M. K., Schramm V. L., and Howell P. L. (2005) Structural rationale for the affinity of pico- and femtomolar transition state analogues of *E. coli* 5'-methylthioadenosine/s-adenosylhomocysteine nucleosidase, *J. Biol. Chem.* 280, 18274-18282.

Lewandowicz, A., and Schramm, V. L. (2004) Transition state analysis for human and *Plasmodium falciparum*: purine nucleoside phosphorylases, *Biochemistry* 43, 1458-1468.

Lewandowicz, A., Tyler, P. C., Evans, G. B., Furneaux, R. H., and Schramm, V. L. (2003) Achieving the ultimate physiological goal in transition state analogue inhibitors for purine nucleoside phosphorylase. *J. Biol. Chem.* 278, 31465-31468.

Johnsson, T.; Edmondson, D. E.; Klinmann, J. P. (1994) Biochemistry 33, 14871-14878.

Kicska, G. A.; Tyler, P. C.; Evans, G. B.; Furneaux, R. H.; Fedorov, A.; Lewandowicz, A.; Cahill, S. M.; Almo, S. C.; Schramm, V. L. (2002) *Biochemistry* 41, 14489-14498.

Lewis, B. E., and Schramm, V. L. (2001a) Conformational equilibrium isotope effects in glucose by $^{13}C$ NMR spectroscopy and computational studies, *J. Am. Chem. Soc.* 123, 1327-1336.

Lewis, B. E., and Schramm, V. L. (2001b) Binding equilibrium isotope effects for glucose at the catalytic domain of human brain hexokinase, *J. Am. Chem. Soc.* 125, 4785-4798.

Lewis, B. E.; Schramm, V. L. (2003a) J. Am. Chem. Soc. 125, 4785-4798.

Lewis, B. E., and Schramm, V. L. (2003b) Isotope effect-mapping of the ionization of glucose demonstrates unusual charge sharing, *J Am. Chem. Soc.* 125, 7872-7877.

Lewis, E. S. (1959) *Tetrahedron* 5, 143-148.

Lewis, E. S.; Boozer, C. E. (1952) *J. Am. Chem. Soc.* 74, 6306-6307.

Miles, R. W.; Tyler, P. C.; Furneaux, R. H.; Bagdassarian, C. K.; Schramm V. L. (1998) *Biochemistry* 37, 8615-8621.

Miller, B. G.; Wolfenden, R. (2002) *Annu. Rev. Biochem.* 71, 847-885.

Miller, C. H.; Duerre, J. A. (1968) *J. Biol. Chem.* 243, 92-97.

Miller, M. B., and Bassler, B. L. (2001) Quorum sensing in bacteria, *Annu. Rev. Microbiol.* 55, 165-199.

Miller, M. B., Skorupski, K., Lenz, D. H., Taylor, R. K., and Bassler, B. L. (2002) Parallel quorum sensing systems converge to regulate virulence in *Vibrio cholerae, Cell* 110, 303-314.

Miller, S. T., Xavier, K. B., Campagna, S. R., Taga, M. E., Semmelhack, M. F., Bassler, B. L., and Hughson, F. M. (2004) *Salmonella typhimurium* recognizes a chemically distinct form of the bacterial quorum-sensing signal AI-2. *Mol. Cell.* 15, 677-687.

Myers, R. W., and Abeles, R. H. (1989) Conversion of 5-S-ethyl-5-thio-D-ribose to ethionine in *Klebsiella pneumoniae*. Basis for the selective toxicity of 5-S-ethyl-5-thio-D-ribose, *J. Biol. Chem.* 264, 10547-10551.

Northcott, D.; Robertson, R. E. (1969) *J. Phys. Chem.* 73, 1559-1563.

Northrop, D. B. (1975) Steady-state analysis of kinetic isotope effects in enzymic reactions, *Biochemistry* 14, 2644-2651.

Northorp, D. B. (1981) The expression of isotope effects on enzyme-catalyzed reactions, *Annu. Rev. Biochem.* 50, 103-131.

Pajula, R. L., and Raina, A. (1979) Purification of spermine synthase from bovine brain by spermine-Sepharose affinity chromatography. *FEBS Lett.* 99, 153-156.

Paneth B. Applications of Heavy Atom Isotope Effects. In Synthesis and Applications of Isotopically Labeled Compounds 1997.

Parkin, D. W., Leung, H. B., and Schramm, V. L. (1984) Synthesis of nucleotides with specific radiolabels in ribose. Primary $^{14}C$ and secondary $^3H$ kinetic isotope effects on acid-catalyzed glycosidic bond hydrolysis of AMP, dAMP, and inosine, *J. Biol. Chem.* 259, 9411-9417.

Parsek, M. R., Val, D. L., Hanzelka, B. L., Cronan, J. E. Jr., and Greenberg, E. P. (1999) Acyl homoserine-lactone quorum-sensing signal generation, *Proc. Natl. Acad. Sci. USA* 96, 4360-4365.

Pegg, A. E. (1983) Inhibition of Aminopropyltransferases. *Methods Enzymol.* 94, 294-297.

Pham, T. V., Fang, Y. R., and Westaway, K. C. (1997) Transition state looseness and α-secondary kinetic isotope effects. *J. Am. Chem. Soc.* 119, 227-232.

Ragione, D.; Porcelli, F. M.; Carteni-Farina, M.; Zappia, V.; and Pegg, A. E. (1985) *Biochem. J.* 232, 335-341.

Riscoe, M. K.; Ferro, A. J.; Fitchen, J. H. (1989) *Parasitol. Today* 5, 330-333.

Rising, K. A., and Schramm V. L. (1994) Enzymatic synthesis of NAD$^+$ with the specific incorporation of atomic labels, *J. Am. Chem. Soc.* 116, 6531-6536.

Rose, I. A. (1980) The isotope trapping method: desorption rates of productive E.S complexes, *Methods Enzymol.* 64, 47-59.

Sauve, A. A., Cahill, S. M., Zech, S. G., Basso, L. A., Lewandowicz, A., Santos, D. S., Grubenmeyer, C., Evans, G. B., Furneaux. R. H., Basso, L. A., Santos, D. S., Almo, S. C., and Schramm, V. L. (2003) Ionic states of substrates and transition state analogues at the catalytic sites of N-ribosyltransferases. *Biochemistry* 42, 5694-5705.

Schauder, S., Shokat, K., Surette, M. G., and Bassler, B. L. (2001) The LuxS family of bacterial autoinducers: biosynthesis of a novel quorum-sensing signal molecule, *Mol. Microbiol.* 41, 463-476.

Schramm, V. L. (2005) Enzymatic transition states: thermodynamics, dynamics and analogue design. *Arch. Biochem. Biophys.* 433, 13-26.

Shi, W; Basso, L. A.; Santos, D. S.; Tyler, P. C.; Furneaux, R. H.; Blanchard, J. S.; Almo, A. C.; Schramm, V. L. (2001a) *Biochemistry* 40, 8204-8215.

Shi, W., Tanaka, K. S. E., Crother, T. R., Taylor, M. W., Almo, S. C., and Schramm, V. L. (2001B) Structural analysis of adenine phosphoribosyltransferase from *Saccharomyces cerevisiae, Biochemisty* 40, 10800-10809.

Shiner, V. J., Jr. (1959) *Tetrahedron* 5, 243-252.

Singh, V.; Shi, W.; Evans, G. B.; Tyler, P. C.; Furneaux, R. H.; Schramm, V. L. (2004) *Biochemistry* 43, 9-18.

Singh, V.; Lee, J. E.; Nunez, S.; Howell, L. P.; Schramm, V. L. (2005a) *Biochemistry* 44, 11647-11659.

Singh, V., Evans, G. B., Lenz, D. H., Mason, J. M., Clinch, K., Mee, S., Painter, G. F., Tyler, P., C., Furneaux, R. H., Lee, J. E., Howell, P. L., and Schramm, V. L., (2005b) Femtomolar transition state analogue inhibitors of 5'-methylthioadenosine/S-adenosylhomocysteine nucleosidase from *Escherichia coli. J. Biol. Chem.* 280, 18265-18273.

Singh, V.; Shi, W.; Almo, S. C.; Evans, G. B.; Furneaux, R. H.; Tyler, P. C.; Zheng, R.; Schramm, V. L. (2006) *Biochemistry* 2006, submitted.

Sufrin, J. R.; Meshnick, S. R.; Spiess, A. J.; Garofalo-Hanuman, J.; Pan, X, Q.; Bacchi, C. J. (1995) *Antimicrob. Agents Chemother.* 39, 2511-2515.

Sunko, D. E., Szele, I., and Hehre, W. J. (1997) Hyperconjugation and the angular dependence of .beta.-deuterium isotope effects, *J. Am. Chem. Soc.* 99, 5000-5005.

Tabor, C. W.; Tabor, H. (1983) *Methods Enzymol.* 94, 294-297

Williams-Ashman, H. G., Seidenfeld, J., and Galletti, P. (1982) Trends in the biochemical pharmacology of 5'-deoxy-5'-methylthioadenosine, *Biochem. Pharmacol.* 31, 277-288.

Winzer, K., Hardie, K. R., Burgess, N., Doherty, N., Kirke, D., Holden, M. T., Linforth, R., Cornell, K. A., Taylor, A. J., Hill, P. J., and Williams, P. (2002) LuxS: its role in central metabolism and the in vitro synthesis of 4-hydroxy-5-methyl-3(2H)-furanone, *Microbiology* 148, 909-922.

Withers, H.; Swift, H. S.; Williams P. (2001) *Curr. Opin. Microbiol.* 4, 186-193.

Wolfenden, R. (1969) Transition state analogues for enzyme catalysis. Nature 223, 704-705.

Wolfenden, R., and Snider, M. J. (2001) The depth of chemical time and the power of enzymes as catalysts, *Acc. Chem. Res.* 34, 938-945.

Xavier, K. B.; Bassler B. L. (2003) *Curr. Opin. Microbial. Rev.* 6, 191-197.

Xue, Q.; Horsewill, A. J.; Johnson, M. R.; Trommsdorff, H. P. (2004) *J. Chem. Phys.* 120, 1107-11119.

Zhou, G. C., Parikh, S. L., Tyler, P. C., Evans, G. B., Furneaux, R. H., Zubkova, O. V., Benjes, P. A., and Schramm, V. L. (2004) Inhibitors of ADP-ribosylating bacterial toxins based on oxacarbenium ion character at their transition states, *J. Am. Chem. Soc.* 126, 5690-5698.

Methylthioadenosine/S-adenosylhomocysteine nucleosidase (MTAN) plays an important role in biological processes including polyamine biosynthesis, methylation, purine salvage and quorum sensing (Hibasami et al., 1980; Carteni-Farina et al., 1983; Winzer et al., 2002; Chen et al., 2002; Williams-Ashman et al., 1982; Miller and Bassler, 2001; Miller at al., 2002). It catalyzes the physiologically irreversible hydrolytic depurination of 5'-methylthioadenosine (MTA) to generate adenine and 5-methylthioribose (FIG. 1A). Adenine is salvaged by adenine phosphoribosyltransferase and the 5-methylthioribose (MTR) can be recovered in the methionine salvage pathway (Myers and Abels, 1989). In *E. coli*, MTA is generated as a by-product of polyamine synthesis from the reaction involving transfer of the aminopropyl group from decarboxylated SAM to putresine. Spermidine synthase is reported to be sensitive to product inhibition by MTA with the inhibition constant of 50 µM for rat spermidine synthase (Pegg, 1983). Mammalian spermine synthase is more sensitive to MTA, with a $K_i$ value of 0.3 µM (Pajula and Raina, 1979). Inhibition of MTAN is therefore expected to inhibit polyamine biosynthesis and the salvage pathways for adenine and methionine. In bacteria MTA is also produced as a by-product in the synthesis of acyl homoserine lactones (AHL) from S-adenosylmethionine (SAM) and acyl-ACP in a reaction catalyzed by AHL synthase (Parsek et al., 1999). Acylhomoserine lactones are also known as autoinducers-1 (AI1) and are used by gram negative bacteria for quorum sensing (FIG. 1B). MTA has an inhibitory effect on AHL synthase (50 µM produces 67% inhibition) (Parsek et al., 1999). In addition to MTA, MTAN also catalyzes hydrolysis of S-adenosylhomocysteine (SAH) to generate adenine and S-ribosylhomocysteine (SRH). SRH is subsequently converted to a group of furanone-like molecules that are collectively known as autoinducer-2 (AI2) (one example is shown in FIG. 1B) (Schauder et al., 2001). Autoinducers (AI1 and AI2) mediate quorum sensing in bacteria to regulate processes such as biofilm formation, virulence and antibiotic resistance. Disruption of these pathways by inhibiting MTAN presents a potential target for interfering with biofilm formation and autoinducer-mediated antibiotic resistance pathways.

Transition state theory predicts that enzymes catalyze reactions by lowering the activation barrier and the catalytic acceleration imposed by the enzyme is proportional to the enzymatic stabilization of the transition state (Wolfe) den, 1969; Wolgenden and Snider, 2001). Transition state analogue inhibitors are designed from the hypothesis that chemically stable analogues that mimic geometric and molecular electrostatic features of the transition state will bind to enzyme tighter than the substrate by a factor approaching the catalytic rate acceleration imposed by the enzyme. For nucleoside hydrolases the calculation predicts a binding affinity of $10^{-19}$ to $10^{-18}$M for mimics of the transition state (DeWolf et al., 1979; Horenstein and Schramm, 1993; Cornell et al., 1996). However, it is not possible to design "perfect" transition state analogues since the actual enzymatic transition state involves non-equilibrium bond lengths and charges that cannot be accurately copied to chemically stable molecules.

Kinetic isotope effects (KIEs) using isotopically labeled substrates combined with computational chemistry are the preferred method to understand the transition states of enzymatic reactions (Lewandowicz and Schramm, 2004; Chen et al., 2000; Birck and Schramm, 2004a; Schramm, 2005). KIEs are defined as the ratio of reaction rates for normal and isotopically labeled substrate. Competitive KIEs measure the effect on $k_{cat}/K_m$ which includes all steps from free reactants to the first irreversible step of the reaction. Intrinsic isotope effects occur when the first irreversible step is bond breaking at the transition state and none of the intervening steps present a significant energetic barrier. Intrinsic KIEs report the difference between bond vibrational ground states for the reactants free in solution and at the transition state. Computational modeling of transition states is facilitated by using intrinsic KIEs as experimental boundary conditions.

Kinetic isotope effects have been used to study the transition states of N-ribosyltransferases including nucleoside hydrolase, purine nucleosidase phosphorylase (PNP), ricin-A chain and thymidine phosphorylase (Horenstein and Schramm, 1993; Lewandowicz and Schramm, 2004; Chen et al., 2000; Birck and Schramm, 2004a). Most N-ribosyltransferases (with the exception of thymidine phosphorylase) have dissociative $S_N1$ reaction mechanisms with transition states exhibiting ribooxacarbenium ion character. Transition state analogue inhibitors have been designed for some of these enzymes by incorporating properties of their transition states into chemically stable analogues. They are powerful inhibitors. One such example is Immucillin-H, a transition state analogue inhibitor of human and bovine PNPs that binds with dissociation constants of 56 pM and 23 pM, respectively. It is currently in clinical trials for T-cell leukemia under the name Fodosine[3]. Second-generation transition state analogues designed specifically to match the transition state of human PNP are tight-binding inhibitors with $K_d$ values to 7 pM and one of these is in clinical trials for psoriasis (Lewandowicz et al., 2003). See http://www.biocryst.com for clinical trial information.

SUMMARY OF THE INVENTION

Accordingly, the inventor has determined the transition state structure of 5'-methylthioadenosine/S-adenosylhomocysteine nucleosidase and has compared the transition state with known inhibitors of 5'-methylthioadenosine/S-adenosylhomocysteine nucleosidase, showing that those inhibitors resemble the charge and geometry of the transition state.

Thus, the present invention is directed to methods of designing a putative inhibitor of a 5'-methylthioadenosine/S-adenosylhomocysteine nucleosidase having 5'-methylthioadenosine and S-adenosylhomocysteine substrates. The methods comprise designing a chemically stable compound that resembles the charge and geometry of the 5'-methylthioadenosine/S-adenosylhomocysteine nucleosidase transition state. In these embodiments, the compound is the putative inhibitor.

In other embodiments, the invention is directed to methods of inhibiting a 5% methylthioadenosine/S-adenosylhomocysteine nucleosidase. The methods comprise identifying a compound that has inhibitory activity to the 5'-methylthioadenosine/S-adenosylhomocysteine nucleosidase by the above-described methods, then contacting the 5'-methylthioadenosine/S-adenosylhomocysteine nucleosidase with the compound.

BRIEF DESCRIPTION OF THE DRAWINGS

FIG. 6 is illustrations showing a comparison of molecular electrostatic potential surfaces (MEPs) for a) transition state of E. coli MTAN b) MT-ImmA, a 77 pM transition state analogue; c) MT-DADMe-ImmA, a 2 pM transition state analogue, and d) pClPhT-DADMe-InunA, a 47 fM transition state analogue. MEPs were calculated at HF/STO3G (Gaussian98/cube) for the optimized geometry at the B3LYP/6-31G(d,p) level of theory and visualized with Molekel 4.0 (34) at a density of 0.008 electron/bohr. The models shown below have the same geometry as the MEP surfaces. The values of $K_d$ are dissociation constants for the inhibitors following slow-onset inhibition or $K_i^*$ in slow-onset analysis (Singh et al., 2005).

FIG. 9 is a model and a graph of experimental results showing the calculation on the transition state of S. pneumoniae MTAN demonstrating that H1'-C1'-C2'-H2' torsion angle rotation causes significant change in 2'-$^3$H equilibrium isotope effect (EIE) and C2'-H2' a bond occupancy. The atoms of H1'-C1'-C2'-H2' torsion angle are encircled in the model for calculation. The isotope effects are calculated with respect to MTA.

FIG. 10 is a model and a graph of experimental results based on calculations showing change in 2'-$^3$H isotope effect (IE) due to polarization of 2'-hydroxyl by hydroxyl anion. The change in 2'-$^3$H IE and C2'-H2' bond length is shown in the graph. The model shows the nature of the calculation. The isotope effects are calculated with respect to MTA.

FIG. 12 is a model and a graph of experimental results showing the relative change in 1'-$^3$H EIEs and total relative energy due to rotation of O4'-C1'-N9-C8 torsion angle in MTA. The isotope effects are calculated with respect to MTA with O4"-C1'-N9-C8 torsion angle of 80°.

FIG. 13 is graphs of experimental results based on calculations showing factors affecting 1'-$^3$H EIEs. Change in 1' 3H Erns and bond length of C1'-H1' bond due to steric imposition of hydrogen molecule on C1'-H1' bond in the transition state of S. pneumoniae MTAN (similar result with oxygen and formaldehyde) are shown in Panel A. The variation in 1'-$^3$H EIEs and occupancy of p-orbital (sum of $p_x$, $p_y$, and $p_z$) of C1' with H1'-C1'-C2'-H2' torsion angle is shown in Panel B. The 1'-$^3$H EIEs in the upper panels are calculated with respect to MTA. Relative change in 1'-$^3$H Ems by H2'-C2'-O—H torsion angle rotation in the transition state (Panel C), the isotope effects are calculated with respect to H2'-C2'-O—H torsion angle of 100°. The effect of polarization of 2'-hydroxyl is on relative 1'-$^3$H EIEs is shown in Panel D. The IE are calculated with respect to $O^{2'hydroxyl}$—$O^{anion}$ distance of 4.0 Å.

FIG. 14 is a model, a graph of experimental results, and a diagram showing variation of 4'-$^3$H EIEs due to polarization 3'-OH by hydroxyl anion and the change of negative on the ring oxygen as a result. The diagram at the bottom shows the difference in the hyperconjugation pattern of the lone pair of ring oxygen (O4') in MTA and at the transition state. The 4'-$^3$H EIEs are calculated relative to MTA.

FIG. 15 is a model and a graph of experimental results showing the rotation of C4'-C5'-S—$C^{Me}$ torsion angle in tetrahydro-2-((methylthio)-methyl)furan. Data showing the tritium isotope effects of the three methyl CHs and the overall Ems are provided in the graph. The overall tritium isotope effect ($^3H_3$) for three methyl hydrogens was calculated by multiplying the individual $^3H_1$ isotope effect for methyl hydrogens. The nature of calculation is summarized in the model. The furan ring is numbered as in MTA, C4' being the carbon to which the 5'-methylthiogroup is attached through C5' and three methyl hydrogens as $H_A$, $H_B$ and $H_c$.

FIG. 19 is graphs of experimental results showing the change in 1'-$^3$H EIEs due to steric imposition of formaldehyde (A) and oxygen (B) on C1'-H1' bond.

FIG. 21 is a model, with a graph of experimental results showing the polarization of 3'-hydroxyl and 2'-$^3$H EIEs. The increase in 2'-$^3$H EIEs can be correlated to increased hyperconjugation from $n_p$ (lone pair) of O2' to σ*(C2'-H2') antibonding orbital (model). The change in [Me-$^3H_3$] isotope effect due to rotation of C4'-C5'-S—$C^s$ torsion angle in the oxacarbenium mimic of tetrahydro-2-((methylthio)methyl) furan is also shown in the model.

DETAILED DESCRIPTION OF THE INVENTION

Figure 1A:
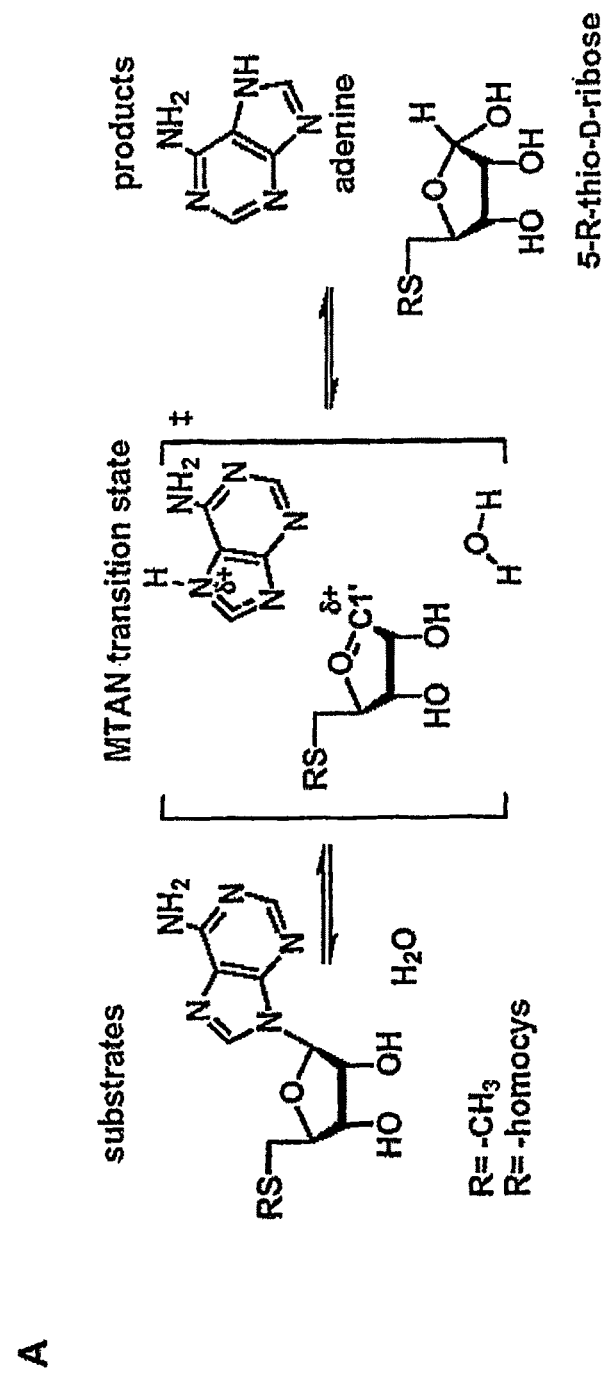
FIG. 1 is diagrams of relevant enzymatic reactions. Panel A illustrates hydrolysis of MTA by E. coli MTAN and the proposed transition state of the reaction. Panel B illustrates the synthesis and structures of bacterial quorum-sensing molecules, autoinducer-1 and autoinducer-2. Furanosyl-based autoinducer-2 molecules that do not contain boron have been described (Miller et al., 2004).
Figure 1B:
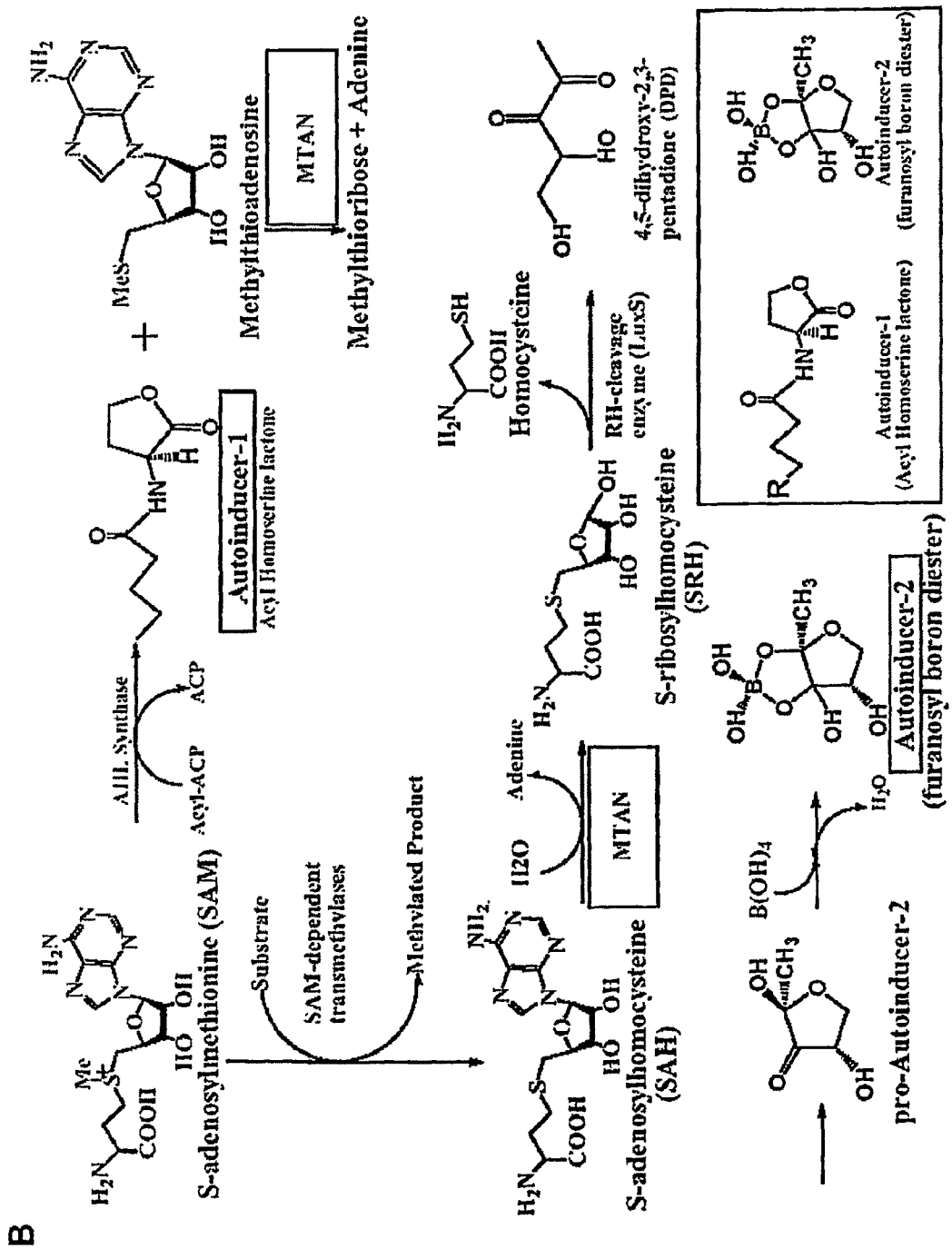

Abbreviations: MTA, 5'-methylthioadenosine; SAH, S-adenosylhomocysteine; SAM, 5-adenosylmethionine; MTR, 5-methylthioribose; MTAN, 5' methylthioadenosine/S-adenosylhomocysteine nucleosidase; MT-ImmA, (1S)-1-(9-deazaadenin-9-yl)-1,4-dideoxy-1,4-imino-5-methylthio-D-ribitol; pC1PhT-ImmA, (1S)-5-(4-chlorophenylthio)-1-(9-deazaadenin-9-yl)-1,4-dideoxy-1,4-imino-D-ribitol; MT-DADMe-ImmA, 5'-methylthio-DADMe-Immucillin-A, (3R,4S)-1-[(9-deazaadenin-9-yl)methyl]-3-hydroxy-4-(methylthiomethyl)pyrrolidine; pC1PhT-DADMe-ImmA, (3R, 4S)-4-(4-chlorophenylthiomethyl)-1-[(9-deazaadenin-9-yl] methyl)-3-hydroxypyrrolidine.

Atoms of MT-ribose are numbered primed and of adenine are numbered unprimed in MTA both in the ground state as well as at the transition state. At the transition state *S. pneumoniae* has no bond order to the adenine leaving group.

Immucillin-His (1S)-1-(9-deazahypoxanthin-9-yl) 1,4-dideoxy-1,4-imino-D-ribitol and has been shown to have a pig, of 6.9 at N4' and >10 at N7 (Sauve et al., 2003). MT-ImmA is chemically similar in the 9-deazaadenine ring and is expected to have a similar $pK_a$.

Accordingly, the inventor has determined the transition state of 5'-methylthioadenosine/S-adenosylhomocysteine nucleosidase and has compared the transition state with known inhibitors of 5'-methylthioadenosine/S-adenosylhomocysteine nucleosidase, showing that those inhibitors resemble the charge and geometry of the transition state. See Example. The inventor concludes that a compound designed to resemble the charge and geometry of the 5'-methylthioadenosine/S-adenosylhomocysteine nucleosidase transition state is likely to be an inhibitor of that enzyme.

Thus, the invention is directed to methods of designing a putative inhibitor of a 5'-methylthioadenosine/S-adenosylhomocysteine nucleosidase having 5'-methylthioadenosine and S-adenosylhomocysteine substrates. The methods comprise designing a chemically stable compound that resembles (a) the molecular electrostatic potential at the van der Walls surface computed from the wave function of the transition state and (b) the geometric atomic volume of the 5'-methylthioadenosine/S-adenosylhomocysteine nucleosidase transition state. In these embodiments, the compound is the putative inhibitor.

As used herein methylthioadenosine/S-adenosylhomocysteine nucleosidase (MTAN) is a prokaryotic enzyme that catalyzes the physiologically irreversible hydrolytic depurination of 5'-methylthioadenosine (MTA) to generate adenine and 5-methylthioribose. Methods of obtaining MTAN from bacteria are known. See, e.g., Cornell et al., 1996 and Lee et al., 2001.

The determination of the molecular electrostatic potential at the van der Walls surface computed from the wave function of the transition state and the geometric atomic volume for any chemically stable compound is within the scope of the art. See, e.g., examples.

As used herein, a compound is resembles the MTAN transition state molecular electrostatic potential at the van der Walls surface computed from the wave function of the transition state and the geometric atomic volume if that compound has an $S_e$ and $S_g \geq 0.5$, where $S_e$ and $S_g$ are determined as in Formulas (1) and (2) on page 8831 of Bagdassarian et al., 1996.

In some preferred embodiments, the compound comprises a purine moiety. In other preferred embodiments, the compound comprises a deazapurine moiety.

In additional preferred embodiments, the compound comprises a moiety resembling the molecular electrostatic potential surface of the ribosyl group at the transition state. In some of these embodiments, the compound comprises a moiety resembling methylthioribose at the transition state. In other of these embodiments, the compound comprises a moiety resembling S-homocysteinyl ribose at the transition state. Preferred examples of moieties resembling the molecular electrostatic potential surface of the ribosyl group at the transition state are substituted iminoribitols, substituted hydroxypyrrolidines, substituted pyridines or substituted imidazoles. In more preferred embodiments, the substituent is an aryl- or alkyl-substituted thiol group, most preferably a methylthiol group.

In other preferred embodiments of these methods, the compound comprises an atomic moiety inserted into the inhibitor providing a compound that mimics the C1'-N9 ribosyl bond distance of a 5'-methylthioadenosine or S-adenosylhomocysteine at the transition state. Preferably, the atomic moiety is a methylene, a substituted methylene, an ethyl, or a substituted ethyl bridge.

Preferably, the compounds designed using these methods exhibit a similarity value ($S_e$) to the transition state greater than to either substrate (see Bagdassarian et al., 1996). $S_e$ can be determined by any known method, for example as described in Bagdassarian et al., 1996.

When compounds are designed by these methods, they can then be synthesized and tested for inhibitory activity to 5'-methylthioadenosine/S-adenosylhomocysteine nucleosidase by known methods.

In these embodiments, the MTAN can be from any prokaryotic species, since the transition state is expected to be the same or very similar for any prokaryotic MTAN. Preferably, the prokaryote is a pathogen, since the inhibitors found by these methods would likely be an effective antibiotic against those pathogens. The pathogen can be a pathogen of plants, microbes, or animals, for example a vertebrate such as a mammal (e.g., a human). Nonlimiting examples of such mammalian pathogens include E. coli, a Staphylococcus sp., a Streptococcus sp., an Enterococcus sp., a Bacillus sp., Bifidobacterium bifidum, a Lactobacillus sp., Listeria monocytogenes, a Nocardia sp., Rhodococcus equi, Erysipelothrix rhusiopathiae, Corynebacterium diptheriae, Propionibacterium acnes, an Actinomyces sp., a Clostridium sp., a Mobiluncus sp., a Peptostreptococcus sp., a Neisseria ap., Moraxella catarrhalis, a Veillonella sp. Actinobacillus actinomycetemcomitans, Acinetobacter baumannii, Bordetella pertussis, a Brucella sp., a Campylobacter sp., a Capnocytophaga sp., Cardiobacterium hominis, Eikenella corrodens, Francisella tularensis, a Haemophilus sp., Helicobacter pylori, Kingella kingae, a Pasteurella, a Klebsiella sp., an Enterobacter sp., a Proteus sp., a Salmonella sp., a Shigella sp., Serratia marcescens, a Yersinia sp. an Aeromonas sp., Plesiomonas shigelloides, a Vibrio sp., an Acinetobacter sp., a Flavobacterium sp., a Pseudomonas sp., a Burkholderia sp., a Xanthomonas sp., a Bacteroides sp., a Prevotella sp., a Fusobacterium sp., Spirillum minus, a Borrelia sp., Bartonella henselae, a Chlamydia sp., a Chlamydophila sp., Coxiella burnetii, an Ehrlichia sp., an Anaplasma sp., a Legionella sp., a Leptospira sp., a Mycobacterium sp., a Rickettsia sp., an Orientia sp., and Treponema pallidum. In preferred embodiments, the mammalian pathogen is an E. coli or a Streptococcus pneumoniae.

In other embodiments, the invention is directed to methods of inhibiting a 5'-methylthioadenosine/S-adenosylhomocysteine nucleosidase. The methods comprise identifying a compound that has inhibitory activity to the 5'-methylthioadenosine/S-adenosylhomocysteine nucleosidase by the above-described methods, then contacting the 5'-methylthioadenosine/S-adenosylhomocysteine nucleosidase with the compound.

The 5'-methylthioadenosine/S-adenosylhomocysteine nucleosidase in these methods can be in vitro or, preferably in a live bacterium. The bacterium can be of any prokaryotic species. Preferably, the prokaryote is a pathogen. The pathogen can be a pathogen of plants, microbes, or animals, for example a vertebrate such as a mammal (e.g., a human). Examples of such mammalian pathogens include E. coli, a Staphylococcus sp., a Streptococcus sp., an Enterococcus sp., a Bacillus sp., Bifidobacterium bifidum, a Lactobacillus sp., Listeria monocytogenes, a Nocardia sp., Rhodococcus equi, Erysipelothrix rhusiopathiae, Corynebacterium diptheriae, Propionibacterium acnes, an Actinomyces sp., a Clostridium sp., a Mobiluncus sp., a Peptostreptococcus sp., a Neisseria ap., Moraxella catarrhalis, a Veillonella sp. Actinobacillus actinomycetemcomitans, Acinetobacter baumcmnii, Bordetella pertussis, a Brucella sp., a Campylobacter sp., a Capnocytophaga sp., Cardiobacterium hominis, Eikenella corroders, Francisella tularensis, a Haemophilus sp., Helicobacter pylori, Kingella kingae, a Pasteurella, a Klebsiella sp., an Enterobacter sp., a Proteus sp., a Salmonella sp., a Shigella sp., Serratia marcescens, a Yersinia sp. an Aeromonas sp., Plesiomonas shigelloides, a Vibrio sp., an Acinetobacter sp., a Flavobacterium sp., a Pseudomonas sp., a Burkholderia sp., a Xanthomonas sp., a Bacteroides sp., a Prevotella sp., a Fusobacterium sp., Spirallum minus, a Borrelia sp., Bartonella henselae, a Chlamydia sp., a Chlamydophila sp., Coxiella burnetii, an Ehrlichia sp., an Anaplasma sp., a Legionella sp., a Leptospira sp., a Mycobacterium sp., a Rickettsia sp., an Orientia sp., and Treponema pallidum. In preferred embodiments, the mammalian pathogen is an E. coli or a Streptococcus pneumoniae.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the example.

EXAMPLE 1

Transition State Structure of 5'-Methylthioadenosine/
S-Adenosylhomocysteine Nucleosidase from
Escherichia coli and Similarity to Transition State
Analogues Example Summary Methylthioadenosine/S-adenosylhomocysteine nucleosidase (MTAN) catalyzes reactions linked to polyamine metabolism, quorum sensing pathways, methylation reactions and adenine salvage. It is a candidate target for antimicrobial drug design. Kinetic isotope effects (KIEs) were measured on the MTAN catalyzed hydrolysis of 5'-methylthioadenosine (MTA) to solve the transition state structure. KIEs measured at pH 7.5 were near unity due to large forward commitment to catalysis. Intrinsic KIE were expressed by increasing the pH to 8.5. Intrinsic KIEs from MTAs labeled at [1'-$^3$H], [1'-$^{14}$C], [2'-$^3$H], [4'-$^3$H], [5'-$^3$H],

[9-$^{15}$N] and [Me-$^3$H$_3$] were 1.160±0.004, 1.004±0.003, 1.044±0.004, 1.015±0.002, 1.010±0.002, 1.018±0.006 and 1.051±0.002, respectively. The large [1'-$^3$H] and small [1'-$^{14}$C] KIEs indicate that the *E. coli* MTAN reaction undergoes a dissociative (D$_N$*A$_N$) (S$_N$1) mechanism with little involvement of the leaving group or participation of the attacking nucleophile at the transition state, causing the transition state to have significant ribooxacarbenium ion character. A transition state constrained to match the intrinsic KIEs was located with density functional theory (B3LYP/6-31G(d,p)). The leaving group (N9) is predicted to be 3.0 Å from the anomeric carbon. The small β-secondary [2'-$^3$H] KIE of 1.044 corresponds to a modest 3'-endo conformation for ribose and a H1'-C1'-C2'-H2' dihedral angle of 53 degrees at the transition state. Natural bond orbital analysis of the substrate and the transition state suggests that the [4'-$^3$H] KIE is due to hyperconjugation between the lonepair (n$_p$) of O3' and antibonding (σ*) orbital of C4'-H4' and the [methyl$^3$H$_3$] KIE is due to hyperconjugation between n$_p$ of sulphur and σ* of methyl C—H bonds. Transition state analogues that resemble this transition state structure are powerful inhibitors, and their molecular electrostatic potential maps closely resemble the transition state.

Introduction

In this study we investigated the transition state of *E. coli* MTAN using multiple KIEs and obtained its geometric and electrostatic properties using density functional methods. We found that the *E. coli* MTAN has a dissociative transition state with significant oxacarbenium ion character. Natural bond orbital (NBO) analysis of the substrate and the transition state was used) to help understand the observed isotope effects. The transition state structure of *E. coli* MTAN obtained here predicted that transition state analogue inhibitors resembling MTA with riboxacarbenium features in the ribosyl group and elevated pK$_a$ values in the leaving group adenine analogue would be powerful inhibitors. These analogues resemble those previously described for 5'-methylthioadenosine phosphorylase and with MTAN, and have dissociation constants that extend into the femtomolar range (Singh et al., 2005).

Materials and Methods

Enzyme preparation. MTAN from *E. coli* was obtained as described previously (17, 24). The histidine tag was removed by chymotrypsin digestion following purification. The digested protein consists of 232 amino acids belonging to *E. coli* MTAN and 10 residues from the N-terminal histidine fusion tag. The protein was analyzed for purity by SDS-PAGE gels stained with Coomassie blue and was stored at 15 mg/mL at −70° C. following flash freezing in dry ice-acetone.

Enzymes and reagents for MTA synthesis. Hexokinase, myokinase, pyruvate kinase, glucose-6-phosphate dehydrogenase, phosphoriboisomerase and phosphogluconic dehydrogenase were purchased from Sigma. Adenine phosphoribosyltransferase from yeast (APRTase) was reported previously (Shi et al., 2001), 5'-phosphoribosylpyrophosphate synthetase (PRPPase) was a gift from Dr. Paul Berti (McMaster University, Hamilton, ON) and SAM synthetase was provided by Dr. George D. Markham (Fox Chase Cancer Center, Philadelphia, Pa.). ATP, monopotassium α-ketoglutrate, glucose, β-nicotinamide adenine dinucleotide phosphate sodium salt (NADP$^+$), phosphoenolpyruvic acid cyclohexylammonium salt (PEP), glycylglycine and dithiothreitol (DTT) were purchased from Sigma.

Figure 2A:
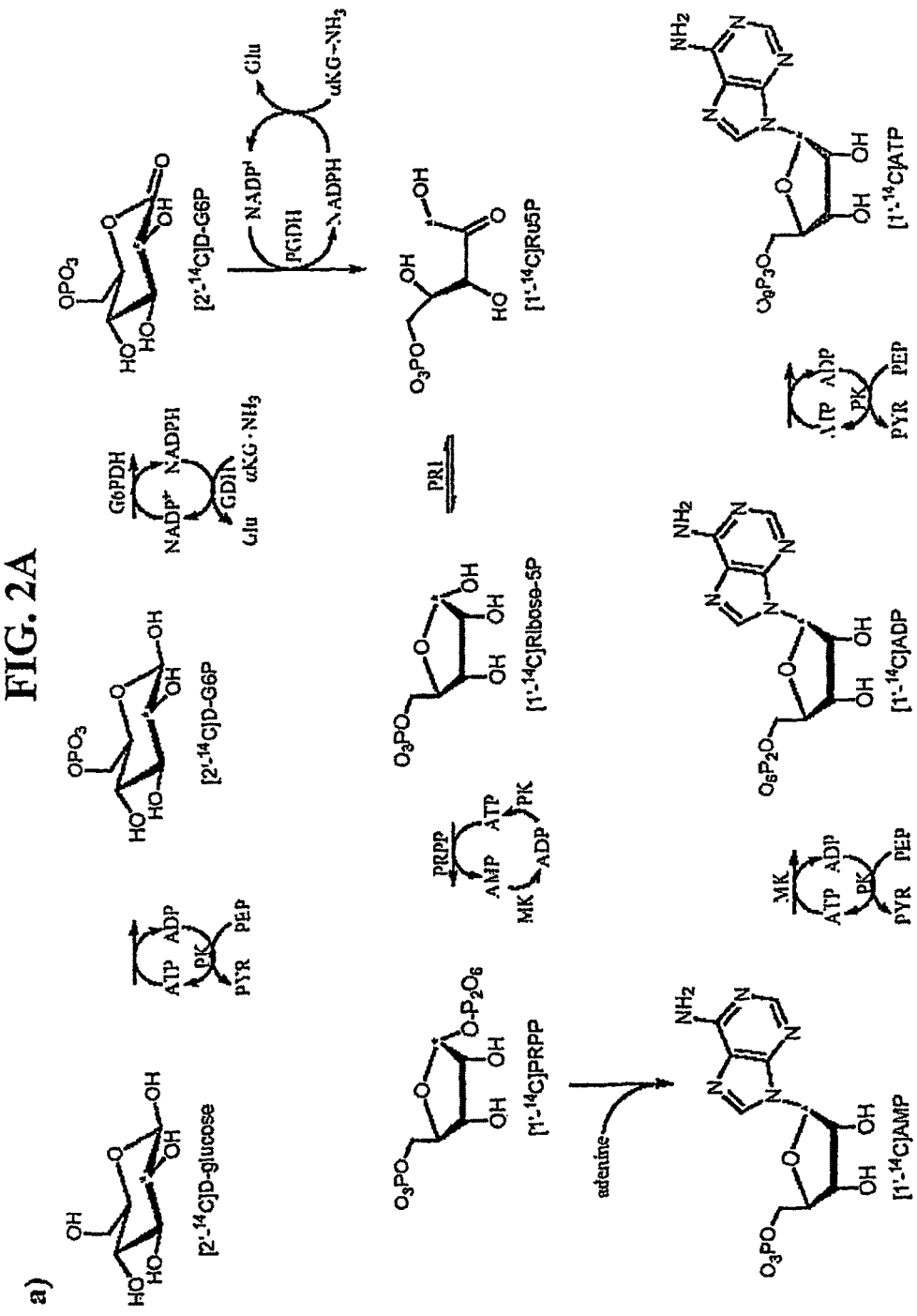
FIG. 2 is diagrams of additional relevant enzymatic reactions. Panel A shows the synthetic route for production of radiolabeled ATP from labeled glucose. Adapted from reference Lewandowicz and Schramm, 2004. This figure uses [1'-$^{14}$C]ATP as the example and indicates the position of the $^{14}$C label with an asterisk. Details are described in the Materials and Methods section. Panel B shows the synthetic route for production of radiolabeled MTA from labeled ATP. For details see the Materials and Methods section.

Synthesis of radiolabeled ATPs. [1'-$^3$H]ATP, [1'-$^{14}$C]ATP, [5'-$^{14}$C]ATP, [5'-$^3$H]ATP and [4'-$^3$H]ATP were synthesized enzymatically from [1-$^3$H]ribose, [2-$^{14}$C]glucose, [6-$^{14}$C] glucose, [6-$^3$H]glucose, and [5-$^3$H]glucose respectively (purchased from American Radiochemicals Inc) as shown in FIG.-2a (26). [2'-$^3$H]ATP was synthesized from [2-$^3$H]ribose-5-phosphate as described previously (27). [9-$^{15}$N, 5'-$^{14}$C]ATP was synthesized from [9-$^{15}$N]adenine and [6-$^{14}$C]glucose. The reaction mixture for the synthesis of radiolabeled ATPs from glucose contained 100 mM phosphate buffer pH 7.5, 50 mM glycylglycine pH 8.0, 50 mM KCl, 20 mM MgCl$_2$, 1 mM glucose, 40 mM PEP, 20 mM α-ketoglutrate, 1 mM DTT, 0.1 mM NADP$^+$, 10 mM adenine, 10-50 µCi of labeled D-glucose in a reaction volume of 1 ml. To the reaction mixture 4.0 units of myokinase, 3.0 units of pyruvate kinase, 5.0 units of phosphoriboisomerase, 1.0 unit of glucose-6-phosphate dehydrogenase and phosphogluconic acid dehydrogenase and 5 units of APRTase and PRPPase were added. The synthesis was initiated by adding 0.1 unit of hexokinase. Reaction mixtures were incubated for 12 hrs at 37° C. and the ATP purified by reverse phase HPLC on a Waters C-18 Deltapak column using methanol, ammonium acetate and water solvent with overall yields in the range of 50%-80%. Following purification the compounds were freeze dried, dissolved in water and stored at −80° C.

Figure 2B:
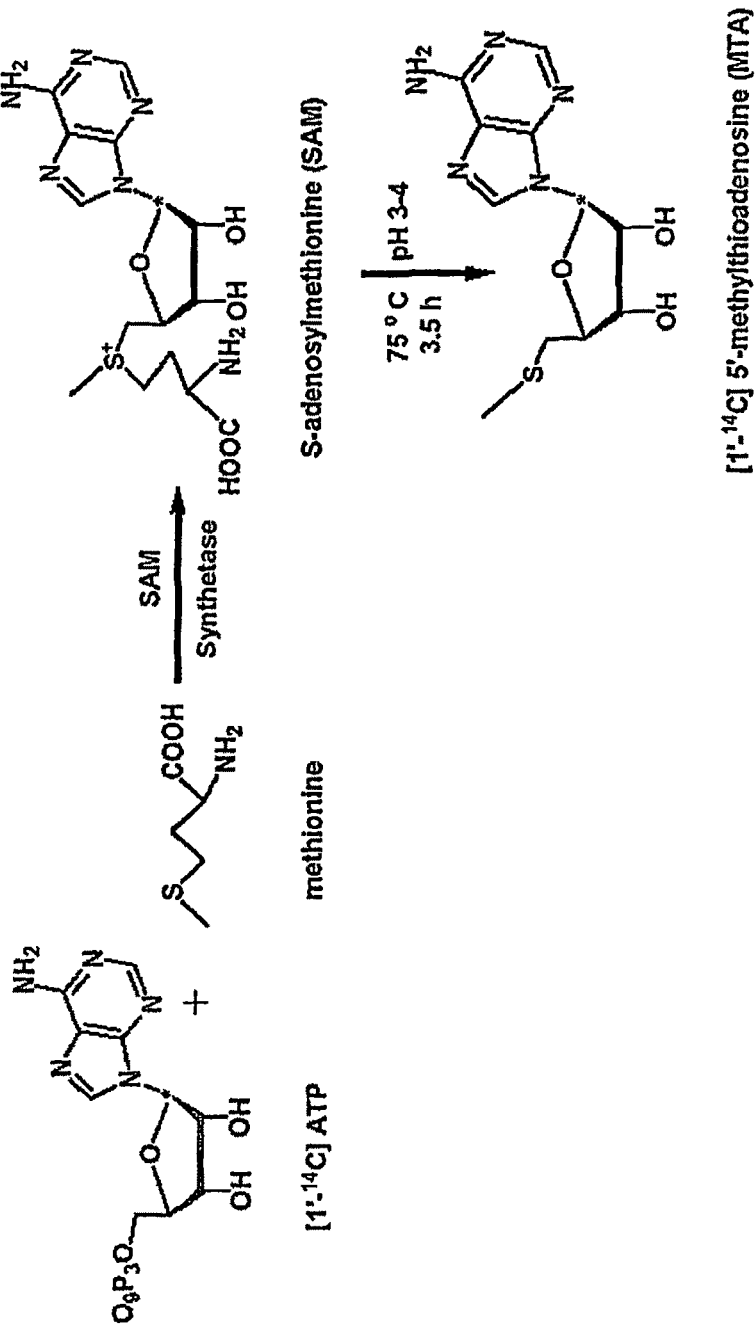

Synthesis of radiolabeled MTAs. [1'-$^3$H]MTA, [1'-$^{14}$C] MTA, [2'-$^3$H]MTA, [4'-$^3$H]MTA, [5'-$^3$H]MTA and [2, 8-$^3$H] MTA were synthesized from the corresponding ATP molecules in two steps (FIG. 2b). In the first step ATP was converted to SAM in a 1 ml reaction mixture containing 100 mM Tris pH 7.9, 50 mM KCl, 20 mM MgCl$_2$, 7% β-mercaptoethanol, 10 mM methionine, 1 U inorganic pyrophosphatase and ~0.1 U SAM synthetase. The reactions were completed in 4 h with 90 to 95% yield. SAM was subsequently converted to MTA by acid hydrolysis at 75° C. This reaction is pH sensitive and maximum yield was obtained at pH 3 to 4, obtained by adding 100 µL of 1 M citrate buffer pH 3.0 to the reaction mixture. SAM was converted to MTA with ~80% yield in 3.5 hr. MTA was purified by reverse phase HPLC first using 10% methanol (by volume) in 100 mM triethylammonium acetate (pH 5.0) as solvent and then in a second step using 50% methanol (by volume) in water as solvent. Purified MTAs were lyophilized and stored at −70° C. in 50% ethanol.

Kinetic isotope effect measurements. Competitive kinetic isotope effects (KIEs) for isotopic substitutions at various positions on the substrate were measured by comparing the relative rate of product formation from pairs of isotopically labeled substrates. Reactions contained a mixture of $^3$H and $^{14}$C labeled substrates with $^3$H:$^{14}$C in 4:1 ratio. The MTAN assay was performed in triplicates of 1 mL reactions (100 mM HEPES pH 7.5 to pH 8.5, 50 mM KCl, 250 µM MTA (including label), 0.5-1 nM MTAN) containing >10$^5$ cpm of $^{14}$C. After 20-30% completion of the reaction, 750 µL of the reaction was resolved on charcoal-Sepharose (acid-washed powdered charcoal and Sepharose in 1:4 ratio made into a slurry in 1 mM MTR and settled in Pasteur pipettes). The remainder of the reaction mixture was allowed to react to completion and then applied to the column. Columns were washed with 2 volumes of 1 mM MTR and radioactive methylthioribose was eluted with 6 volumes of 15 mM MTR containing 50% ethanol. Each 1.0 mL of eluate was mixed with 9.0 mL scintillation fluid and counted for at least 3 cycles at 10 minutes per cycle. The $^3$H to $^{14}$C ratio was determined for partial and complete reactions and the KIEs were corrected to 0% hydrolysis by the equation $$KIE = \frac{\ln(1-f)}{\ln\left[\left(1-f\frac{R_f}{R_o}\right)\right]}$$

Where f is the fraction of reaction progress and $R_f$ and $R_o$ are ratios of heavy to light isotope at partial and total completion of reaction, respectively.

Commitment to catalysis. Forward commitment to catalysis refers to partitioning of the Michaelis complex to product relative to being released unchanged into the solution ($k_{cat}/K_{off}$) (Northrop, 1975). It was measured by isotope trapping (Rose, 1980) using rapid-mix pre-steady state conditions. Enzyme (13 µL of 20 µM) in 100 mM HEPES pH 8.5 and 50 mM KCl was mixed with an equal volume containing 200 µM of [8-$^{14}$C]MTA in the same buffer. After 19 ms the mixture (the pulse solution) was diluted with 975 µL of solution containing 3 mM unlabeled MTA in 100 mM HEPES pH 8.5 and 50 mM KCl (the chase solution). Samples of 100 µL were quenched with 1N HCl at the indicated time and quantitated for product formation (reverse phase HPLC using C-18 Deltapak column by 25% methanol and 50% of 100 mM ammonium acetate pH 5.0) by scintillation counting. The forward commitment to catalysis is the fraction of bound MTA converted to product following dilution in excess MTA.

Determination of Transition State Using Hybrid Density Functional Theory (DFT). A transition state structure that reproduced the intrinsic KIE values for the hydrolysis of MTA by *E. coli* MTAN was determined in vacuo by hybrid density functional theory implemented in Gaussian03 (Frisch et al., 2003) using 5'-methylthioadenosine as substrate. The substrate and the model transition state were optimized using the three-parameter Becke (B3) exchange functional, the LYP correlation functional and the standard 6-31G(d,p) basis set. Bond frequencies were computed for optimized structures at the same level of theory with the same basis set (Becke, 1996). The methylthio group of MTA was frozen in the substrate and the transition state by constraining the C4'-C4'-C5'-S dihedral angle to 173.5 and 166 degrees respectively. These dihedral angles were obtained from the crystal structure of 5'-methylthiotubericidin (MTT, a substrate analogue) and of MT-DADMe-ImmA (a transition state analogue inhibitor) with *E. coli* MTAN (Lee et al., 2005).

Kinetic isotope effects were calculated at 298 K from the computed frequencies with Isoeff 98 on the basis of equations described earlier (Anisimov and Paneth, 1999). The transition state was optimized iteratively with additional constraints until the isotope effects calculated for the transition state matched the experimental intrinsic KIEs. The constraints were released prior to frequency calculations. The Natural Bond Orbital (NBO) analysis was performed on the optimized structures by using the POP=NBO option in Gaussian03.

Calculations of Molecular Electrostatic Potential Surface. Molecular electrostatic potential (MEP) surfaces were calculated by the CUBE subprogram of Gaussian03. The formatted checkpoint files used in the CUBE subprogram were generated by geometry optimization at B3LYP level of theory and 6-31G(d,p) basis set. The MEP surfaces were visualized using Molekel 4.0 package (34) at a density of 0.008 electron/bohr (Bagdassarian et al., 1996).

Results and Discussion

Effect of pH on Kinetic Isotope Effects. *E. coli* MTAN catalyzes the physiologically irreversible N-ribosyl hydrolysis of 5'-methylthioadenosine to adenine and 5-methylthioribose with a $k_{cat}$ of 20 s$^{-1}$ at pH 7.5. The kinetic isotope effects measured at pH 7.5 were all near unity. This pattern is consistent with the suppression of isotope effects by kinetic factors and is a common problem in the determination of enzymatic transition states from KIE (Northrup, 1975; Berti and Tanaka, 2002; Northrup, 1981). Suppression of KIE due to large forward commitment is expected with tight-binding substrates and the 0.43 µM $K_m$ for MTA suggested this to be the mode of KIE suppression. KIEs can also be suppressed by reverse commitments in chemically reversible reactions but the hydrolytic MTAN reaction is irreversible under the conditions used here, thus reverse commitment is considered unlikely. Forward commitment was reduced by varying the pH used in the KIE measurements. The KIE for [1'-$^3$H]MTA increased from 1.020 to 1.160 as the pH was increased from 5.5 to 8.5 but was not further altered by going to pH 9.5, suggesting that the KIE at pH 8.5 is approaching intrinsic values. The KIEs for other positions were subsequently measured at pH 8.5. At pH 8.5, the $k_{cat}$ is reduced 14-fold and the $K_m$ is increased to 2.0±0.5 µM. Elevated pH decreases $k_{cat}/K_m$ by a factor of 65, consistent with a change from near-full to near-zero commitment.

Commitment Correction and Intrinsic KIEs. Competitive KIEs measured experimentally give the apparent isotope effect on $k_{cat}/K_m$, which includes contributions from the non-chemical steps. Intrinsic isotope effects are obtained from the apparent isotope effects after correcting them for the forward and the reverse commitment using the expression derived by Northorp (1981):

$$^T(V/K) = \frac{^Tk + C_f + C_r{}^TK_{eq}}{1 + C_f + C_r}$$

Where $^T(V/K)$ is an observed tritium isotope effect, $C_f$ is the forward commitment for catalysis, $C_1$ is reverse commitment to catalysis, $^TK_{eq}$ is the equilibrium isotope effect, and $^Tk$ is the intrinsic isotope effect. The hydrolytic reaction catalyzed by *E. coli* MTAN is irreversible under initial rate conditions, therefore the above expression can be reduced to;

$$^T(V/K) = \frac{^Tk + C_f}{1 + C_f}$$

Figure 3:
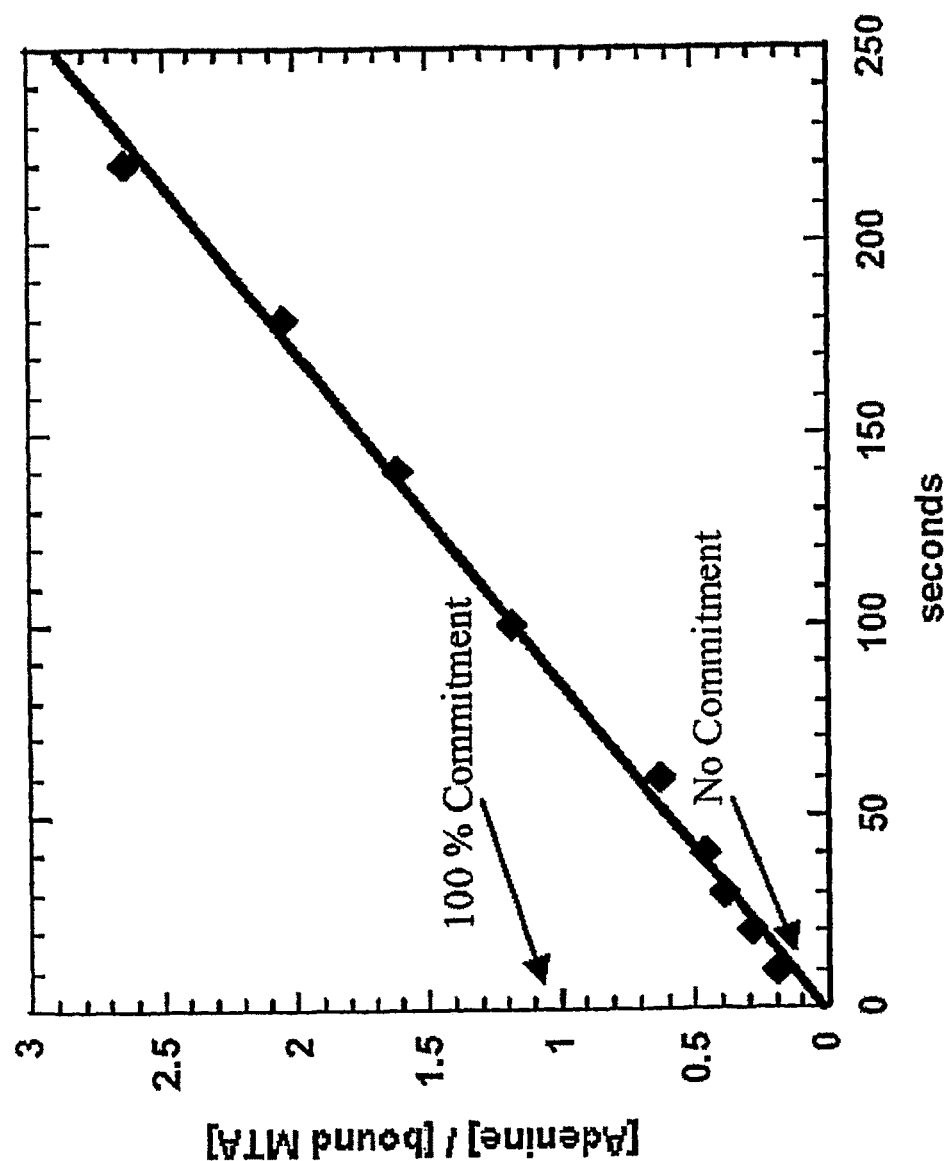
FIG. 3 is a graph of experimental results showing the commitment to catalysis for the MTAN-MTA complex at pH 8.5. The complex of MTAN and $^{14}$C-MTA was diluted with a large excess of unlabeled MTA at 19 msec. Subsequent reaction partitions bound $^{14}$C-MTA to product (forward commitment) or permits release into free, unbound MTA. Zero commitment extrapolates through the origin while full (100%) commitment would intersect at 1.0 on the ordinate as indicated by the arrow. The forward commitment was calculated by plotting the amount of labeled adenine formed following addition of chase solution divided by amount of labeled MTA on the active site before dilution with chase solution and extrapolating this ratio back to zero time. The line is drawn from an ordinary least square fit of the data, y errors only. The intercept value is 0.020±0.0027.
Figure 4:
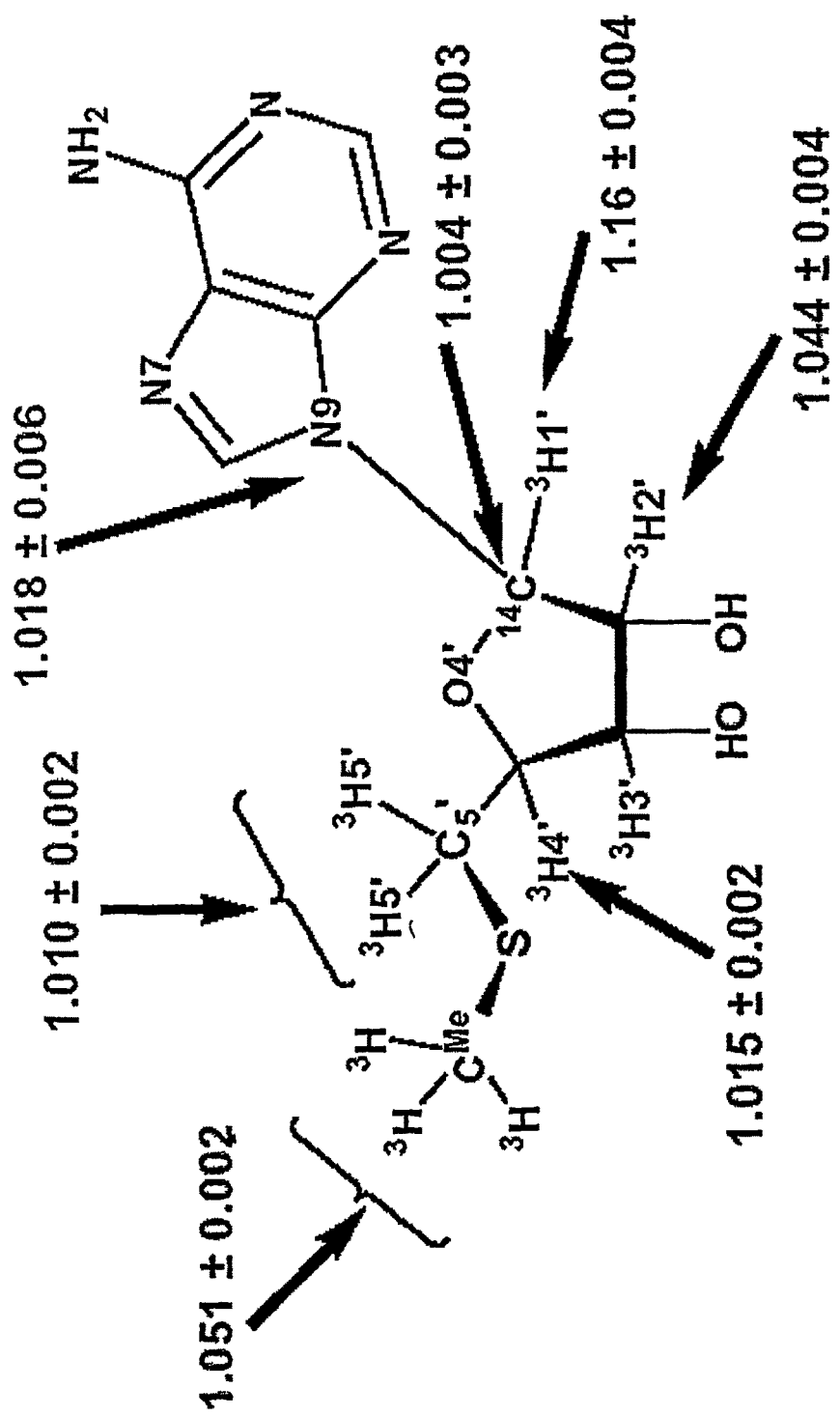
FIG. 4 is a diagram of intrinsic kinetic isotope effects measured for the hydrolysis of MTA by E. coli MTAN. The KIE for [5'-$^{14}$C] MTA was assumed to be unity and was used as a control for all the other KIE experiments.

Forward commitment measures the effective partitioning of the Michaelis complex to product relative to being released as unchanged substrate ($k_{cat}/k_{off}$). It was measured at pH 8.5 using the isotope trapping method as developed by Rose (1980). The external forward commitment factor of 0.020±0.027 for *E. coli* MTAN establishes that binding of MTA at pH 8.5 is freely reversible and the isotope effects are within experimental error of their intrinsic values (FIG. 3). Thermodynamically it suggests that at pH 8.5 the ΔG barrier for the binding of substrate to the enzyme is small relative to ΔG for the chemical step. The $^TK_{eq}$ for the MTAN reaction is assumed to be near unity since the anomeric carbon is sp$^3$-hybridized in both reactant and product. Thus, the experimental KIEs at pH 8.5 are within experimental errors of intrinsic values (Table 1).

TABLE 1

Kinetic Isotope Effects Measured at pH 8.5
for Hydrolysis of MTA by E. coli MTAN.

| Substrates | Type of KIE | Intrinsic KIE[a] |
|---|---|---|
| [1'-$^3$H] and [5'-$^{14}$C] MTA | α-secondary | 1.160 ± 0.004 |
| [1'-$^{14}$C] and [5'-$^3$H] MTA | primary | 0.994 ± 0.004 |
| | | 1.004 ± 0.003[b] |
| [2'-$^3$H] and [5'-$^{14}$C] MTA | β-secondary | 1.044 ± 0.004 |
| [9-$^{15}$N/5'-$^{14}$C]/[5-$^3$H]MTA | primary | 1.008 ± 0.002 |
| | | 1.018 ± 0.006[c] |
| [4'-$^3$H] and [5'-$^{14}$C] MTA | γ-secondary | 1.015 ± 0.002 |
| [5'-$^3$H] and [5'-$^{14}$C] MTA | δ-secondary | 1.010 ± 0.002 |
| [Me—$^3$H] and [5'-$^{14}$C] MTA | remote | 1.051 ± 0.002 |

[a]KIE's are corrected to 0% substrate depletion. Since commitment factors are small (FIG. 3), observed values are intrinsic KIEs except for the [1'-$^{14}$C] and [9-$^{15}$N] primary effects.
[b]The 1'-$^{14}$C KIE was corrected for the 5'-$^3$H KIE according to expression KIE = KIE$_{observed}$ × 5'-$^3$H KIE.
[c]The 9-$^{15}$N KIE was corrected for 5'-$^3$H KIE according to expression KIE = KIE$_{observed}$ × 5'-$^3$H KIE.

Correction to Remote Label KIEs. The isotope effect at 5'-$^{14}$C was assumed to be unity because it is three bonds distant from the reaction center and $^{14}$C does not report isotope effects for geometric changes, unlike remote tritium labels (Lewis and Schramm, 2001a, b; 2003). For measuring 1'-$^{14}$C and 9-$^{15}$N KIEs, [5'-$^3$H]MTA was used as the remote label. The 1'-$^{14}$C and 9-$^{15}$N KIEs were corrected for the remote label KIE. The isotope effects at 4'-$^3$H and 5'-$^3$H were significant, even though these atoms are three and four bonds away from the reaction center. Remote isotope effects have been observed for isotopic substitution at these positions in other N-ribosyltransferases; for example in bovine PNP, remote isotope effects of 1.024 and 1.06 have been observed for [4'-$^3$H] and [5'-$^3$H]inosine, respectively. The [4'-$^3$H] and [5'-$^3$H] KIE for E. coli MTAN were smaller, 1.015 and 1.010, respectively (Table 1).

Computational Modeling of the Transition State of E. coli MTAN. The intrinsic KIEs provide boundary conditions for the computational modeling of the transition state of E. coli MTAN. The [9-$^{15}$N] KIE of 1.018 along with [1'-$^3$H] KIE of 1.160 suggests that the transition state has a small bond order to the leaving group and little participation of the attacking nucleophile. The water nucleophile was therefore not included in the calculation of the transition state. The transition state was modeled using B3LYP level of theory and 6-31 G(d,p) basis set. The methylthio group of MTA is far from the site of nucleophilic substitution and its conformation does not influence the magnitude of primary and secondary KIEs near C1' and has no influence on the chemistry or the conformation of the oxacarbenium ion or the leaving group. Therefore, during calculations to locate the transition state the methylthio group was constrained using the dihedral angle from the crystal structure of E. coli MTAN with a transition state analogue (MT-DADMe-ImmA), a close approximation of its transition state conformation (Singh et al., 2005; Lee et al., 2005). The applied constraints on the transition state structure were iteratively optimized until the calculated KIEs closely matched the experimental KIEs. Properties of the transition state are discussed below together with a discussion of individual isotope effects.

The transition state refers to a saddle point on a potential energy surface that is characterized by a single imaginary frequency ($v^{\ddagger}$) in which one of the restoring vibrational modes is converted to a translation mode along the reaction coordinate (the imaginary $v^{\ddagger}$). The initial ab initio transition state had an imaginary frequency of 397 i cm$^{-1}$. However, when the transition state geometry was constrained to fit the intrinsic KIEs, two additional imaginary frequencies of approximately 178 i cm$^{-1}$ and 54 i cm$^{-1}$ were obtained for the transition state. (The enzymatic transition state is obtained by matching the calculated KIEs to intrinsic KIEs. In calculations for dissociative $S_N1$ transition states, multiple negative frequencies appear when constraints are applied to in vacuo ab initio transition states to match experimental KIEs.) The smaller negative frequency 54 i cm$^{-1}$ corresponds to motion along the reaction coordinate, whereas the larger negative frequency of 178 i cm$^{-1}$ arises due to constraints applied to the 5' end of MTA. This frequency (178 i cm$^{-1}$) does not affect the KIEs at the reaction center, as confirmed by additional computed equilibrium isotope effects (Ems) on the closely related intermediate structure. The transition state of E. coli MTAN is the in vacuo model for which the calculated KIEs match the experimental KIEs. The properties of the transition state are listed in Table 2 and are discussed in the context of individual kinetic isotope effects.

1'-$^{14}$C Isotope Effects. The α-primary 1'-$^{14}$C KIE is useful in determining the mechanism of nucleophilic substitution reactions ($S_N1$ vs $S_N2$) and is sensitive to the motion along the reaction coordinate. For a fully dissociative $S_N1$ transition state, 1'-$^{14}$C KIE is close to unity. For a slightly associative $S_N1$ transition state it is in the range of 1.01 to 1.03 and it is 1.080 to 1.13 for associative $S_N2$ transition states (Berti and Tanaka, 2002). Many N-ribosyltransferases have 1'-$^{14}$C KIE between 1.00 and 1.03 and thus have dissociative $S_N1$ mechanisms with significant ribooxacarbenium character. An exception is the arsenolysis reaction of thymidine phosphorylase which has a 1'-$^{14}$C KIE of 1.13 implying an associative $S_N2$ mechanism and a neutral transition state (Birck and Schramm, 2004a). The primary 1'-$^{14}$C isotope effect of 1.004 for E. coli MTAN suggests a dissociative $D_N*A_N$ mechanism, like other N-ribosyltransferases, with the transition state exhibiting significant cationic character with low Pauling bond order to the leaving group and insignificant bond order to the attacking nucleophile. The small primary 1'-$^{14}$C KIE is consistent with a change in hybridization at the anomeric carbon as it changes from sp$^3$ hybridized carbon in the substrate towards an sp$^2$ hybridized planar configuration of a fully dissociative transition state. The 1'-$^{14}$C KEE of 1.004 together with the 9-$^{15}$N KIE of 1.018 suggests that at the transition state anomeric carbon has minimal bond order to the adenine leaving group (N9). The transition state consistent with the intrinsic KIEs predicted N9 to be 3.0 Å away from the anomeric carbon (C1'). The nucleophile was found to be >3.5 Å from the anomeric carbon since including it at this distance altered the calculated KM beyond the errors of the experimental KIEs. The natural bond orbital analysis of the transition state and the substrate reveals that the anomeric carbon is sp$^{2.30}$ hybridized at the transition state relative to sp$^{2.83}$ in the substrate (Table 2). These changes cause increased cationic character at the transition state (positive charge on O4' and C1' increases by +0.20 and +0.25 respectively) relative to the reactant state. This sharing of charge is characteristic of ribooxacarbenium ions (Berti and Tanaka, 2002). The change in hybridization creates a partially empty 2pz orbital on the anomeric carbon that hyperconjugates with the C2'-H2' and stabilizes the transition state by partially neutralizing the positive charge on the anomeric carbon.

TABLE 2

Geometric and Electronic Changes in Conversion of Substrate (GS) to
the Transition State (TS) for *E. coli* MTAN (B3LYP/6-31G(d, p))

| Bond Type | Bond Length GS | Bond Length TS | Bond Order Change[a] $\Delta(\sigma - \sigma^*)$ | Hyperconjugation (kcal/mol)[b] Substrate $\sigma\rightarrow$ | $\rightarrow\sigma^*$ | TS $\sigma\rightarrow$ | $\rightarrow\sigma^*$ | $\Delta\Sigma$(TS − GS) | Orbital Changes[c] GS hybrid | Carbon cont.(%) | TS hybrid | Carbon cont.(%) |
|---|---|---|---|---|---|---|---|---|---|---|---|---|
| C1'—H1' | 1.0935 | 1.0864 | −0.01501 | 9.05 | 8.61 | 8.16 | 8.22 | −1.28 | sp$^{2.75}$ | 63.33 | sp$^{1.81}$ | 64.13 |
| C2'—H2' | 1.0934 | 1.0960 | +0.00216 | 4.84 | 12.56 | 7.93[d] | 9.36 | −0.11 | sp$^{2.56}$ | 63.53 | sp$^{2.40}$ | 65.30 |
| C4'—H4' | 1.0984 | 1.0927 | −0.00865 | 8.85 | 12.50[e] | 10.06 | 6.74 | 3.60 | sp$^{3.02}$ | 62.15 | sp$^{3.00}$ | 64.65 |
| C1'—N9 | 1.4627 | 3.0000 | | 7.35 | 26.36 | | | | sp$^{3.26}$ | 35.80 | | |
| C5'—H5'(R) | 1.0940 | 1.0947 | +0.00429 | 4.88 | 4.43 | 3.87 | 7.29[g] | 1.85 | sp$^{3.07}$ | 63.50 | sp$^{2.87}$ | 63.92 |
| C5'—H5'(S) | 1.0942 | 1.0921 | −0.00246 | 3.78 | 5.33[h] | 4.21 | 4.60 | −0.30 | sp$^{2.93}$ | 63.53 | sp$^{2.78}$ | 64.16 |
| C$^S$—H(A) | 1.0919 | 1.0915 | +0.00254 | 2.41 | 1.14 | 0.75 | 3.98[i] | 1.18 | sp$^{2.96}$ | 63.13 | sp$^{2.75}$ | 63.18 |
| C$^S$—H(B) | 1.0927 | 1.0913 | −0.00113 | 0.00 | 3.99 | 0.00 | 4.00[i] | 0.01 | sp$^{2.82}$ | 62.79 | sp$^{2.75}$ | 63.24 |
| C$^S$—H(C) | 1.0914 | 1.0915 | −0.00226 | 0.68 | 4.69[j] | 2.53 | 1.03 | −1.81 | sp$^{2.76}$ | 62.69 | sp$^{2.92}$ | 63.88 |
| C3'—H3' | 1.0978 | 1.0934 | −0.01269 | 7.46 | 2.26 | 4.06 | 6.95[k] | 1.29 | sp$^{2.78}$ | 62.87 | sp$^{2.64}$ | 63.95 |

[a]Calculated by subtracting the number of electrons occupying the σ* orbital from the number occupying the σ orbital and listed as the change between substrate and transition state (TS) (Substrate-TS).
[b]Sum of second order perturbation contributions calculated by NBO analysis with a cutoff = 0.5 kcal/mol.
[c]Hybridization of the carbon atom and contribution of the carbon atom to the bond as percent of bond contribution. Lp1 is the sp-type lone pair; and Lp2 is p-type lone pair:
[d]Lp2(C1'); [f]Lp(O3'); [g]Lp2(S); [i]Lp2(S); [k]Lp2(O3') are better acceptors in the transition state while [e]Lp2(O4'); [h]Lp2(S); [j]Lp2(S) are better acceptors in the substrate.

1'-$^3$H Isotope Effects. A large 1'-$^3$H KIE α-secondary hydrogen kinetic isotope effect is indicative of a dissociative S$_N$1 transition state with oxacarbenium character whereas a small 1'-$^3$H KIE indicates a neutral S$_N$2 transition state with significant participation of the nucleophile (Berti and Tanaka, 2002; Pham et al., 1997). The intrinsic 1'-$^3$H KIE of 1.16 measured for *E. coli* MTAN is consistent with a dissociative transition state with oxacarbenium ion character. The magnitude of the 1'-$^3$H KIE contains contributions from two competing factors, the out-of-plane bending mode of the C1'-H1' due to increased steric freedom at the transition state relative to substrate and a decrease in "vibrational looseness" of the C1'-H1' stretching mode at the transition state. The predominant contribution to the observed normal KIE comes from the increased out-of-plane bending motion of the C1'-H1' sigma bond due to reduced steric crowding at the transition state relative to substrate (Pham et al., 1997). The normal isotope effect caused by increased out-of-plane bending motion is opposed by the decrease in the stretching mode for C1'-H1' due to change in hybridization of the anomeric carbon from Sp$^{2.83}$ in the substrate to sp$^{2.3}$ at the transition state or the increased s-character at the transition state (Table 2). The increased s-character of the anomeric carbon in C1'-H1' sigma bond opposes the observed normal KIE. Although both factors contribute to the magnitude of this KIE, the relative variation in the observed 1'-$^3$H KIE for different enzymes is dominated by variation in the out-of-plane bending motion at the transition state. This mode is highly sensitive to C1'-N9 distance and to nucleophilic participation (distance) at the transition state. The contribution of out-of-plane bending modes to intrinsic 1'-$^3$H KIE outweighs the stretching effects, which are less sensitive to atomic distances in the reaction coordinate.

Many N-ribosyltransferases have S$_N$1 transition states that are characterized by large 1'-$^3$H KIE. Human and *Plasmodium falciparum* PNPs both demonstrate well-developed ribooxacarbenium ions at the transition state and have 1'-$^3$H KIEs of 1.184 and 1.116 respectively, for inosine as substrate (Table 3) (Lewandowicz and Schramm, 2004). Ricin A-chain with a stem-loop RNA substrate also has a carbocation ribosyl transition state characterized by an intrinsic 1'-$^3$H KIE of 1.163 (Chen et al., 2000). The computational modeling of 1'-$^3$H KIE to obtain an exact match with experimental values is difficult because of ill-defined differences between in vacuo calculations and unknown protein atomic distances at the transition state. The computed isotope effect for 1'-$^3$H MTA for the *E. coli* MTAN transition state at 298K in vacuum using the B3LYP/6-31G(d,p) level of theory is 1.38, more than double the measured intrinsic 1'-$^3$H KIE of 1.160. Catalytic site interactions at the transition state are proposed to dampen the out-of-plane bending motions of CH bonds causing suppression of their intrinsic KIEs. These effects are not reproduced in the in vacuo calculations. This effect is well-known for α-secondary isotope effects (Pham et al., 1997) and the structure of the transition state does not depend on the matching of this value. Although the large 1'-$^3$H KIE is consistent with a ribooxacarbenium ion at the transition state, the disagreement with in vacuo ab initio calculations tells us that the transition state is a relatively crowded environment relative to vacuum. We also know this from structural studies with transition state analogues, but these lack information on the dynamic excursions of the transition state (Schramm, 2005). The relatively suppressed 1'-$^3$H KIE observed here suggests a dynamically constrained environment during the short time ($\sim 10^{-13}$ sec) the reactant spends at the transition state.

TABLE 3

Comparison of Intrinsic KIEs for *E. coli* MTAN with Other N-ribosyltransferases.

| | | Intrinsic KIEs | | | | |
|---|---|---|---|---|---|---|
| Position | Type of KIE | *E.coli* MTAN | RNA-ricin-A chain[a] | bovine PNP[b] | human PNP[c] | P.f. PNP[c] |
| [1'-$^3$H] | α-secondary | 1.160 ± 0.004 | 1.163 ± 0.009 | 1.141 ± 0.004 | 1.184 ± 0.004 | 1.116 ± 0.007 |
| [1'-$^{14}$C] | primary | 1.004 ± 0.003 | 0.993 ± 0.004 | 1.026 ± 0.006 | 1.002 ± 0.006 | 0.996 ± 0.006 |
| [2'-$^3$H] | β-secondary | 1.044 ± 0.004 | 1.012 ± 0.004 | 1.152 ± 0.003 | 1.031 ± 0.004 | 1.036 ± 0.003 |

TABLE 3-continued

Comparison of Intrinsic KIEs for *E. coli* MTAN with Other N-ribosyltransferases.

| | | Intrinsic KIEs | | | | |
|---|---|---|---|---|---|---|
| Position | Type of KIE | *E.coli* MTAN | RNA-ricin-A chain[a] | bovine PNP[b] | human PNP[c] | P.f. PNP[c] |
| [9-$^{15}$N] | primary | 1.018 ± 0.006 | 1.012 ± 0.004 | 1.010 ± 0.005 | 1.029 ± 0.006 | 1.019 ± 0.005 |
| [4'-$^{3}$H] | γ-secondary | 1.015 ± 0.002 | 0.992 ± 0.004 | 1.008 ± 0.004 | 1.024 ± 0.003 | 1.009 ± 0.002 |
| [5'-$^{3}$H] | δ-secondary | 1.010 ± 0.002 | 0.996 ± 0.003 | 1.033 ± 0.005 | 1.062 ± 0.002 | 1.064 ± 0.003 |
| [Me—$^{3}$H] | remote | 1.051 ± 0.002 | NA | NA | NA | NA |

[a]Taken from Chen et al., 2000.
[b]Taken from reference Kline and Schramm, 1993.
[c]Taken from reference Lewandowicz and Schramm, 2004.
P.f. refers to *Plasmodium falciparum* PNP.

2'-$^{3}$H Isotope Effects. The magnitude of the β-secondary 2'-$^{3}$H KIE reports on the geometry of ribose at the transition state and is proportional to the vibrational looseness of the C2'-H2' sigma bond. Hyperconjugative transfer of electrons from the C2'-H2' sigma bond to the partially empty 2p$_z$ orbital of C1' is responsible for these bond changes (Sunko et al., 1997). Two factors influence the interaction, 1) the degree of overlap of the C2'-H2' sigma bond with the empty 2p$_z$ orbital and 2) the cos$^2$θ function of this overlap and the emptiness of 2p$_z$ which is proportional to the C1-N9 bond length. For a completely dissociated ribooxacarbenium ion at the transition state the maximum 2'-$^{3}$H KIE of 1.12 was calculated for a 2p$_z$-C1'-C2'-H2' dihedral angle of 0 degrees and it decreased with the increase in the electron population of the 2p$_z$ orbital or the sp$^3$ character of C1'. The small 1.044 KIE observed for [2'-$^{3}$H]MTA suggests only modest orbital overlap with 2p$_z$ and is similar to that found for human and *P. falciparum* PNPs at 1.031 and 1.036, respectively (Table 3) (Lewandowicz and Schramm, 2004). The relatively small [2'-$^{3}$H] KIE indicates that the ribosyl group adopts a 3-endo configuration at the transition state. The transition state of *E. coli* MTAN corresponds to a H1'-C1'-C2'-H2' dihedral angle of 53° and the sugar has a small 3-endo pucker corresponding to a O4'-C1'-C2'-C3' dihedral angle of –10°.

Primary [9-$^{15}$N] Isotope Effect. The 9-$^{15}$N KIE reports on the rehybridization of adenine N9 at the transition state as the result of loss of C1-N9 bond order. In addition, enzymatic groups that interact with the adenine ring can alter ring conjugative bonding. The maximum theoretical KIE value predicted for full loss of a covalent bond to N9 is 1.04. The intrinsic KIE of 1.018 suggests significant loss of bond order to N9 at the transition state combined with altered bond conjugation. The computational model of the transition state that best matches the full family of KIEs gives a calculated 9-$^{15}$N KIE of 1.021 and is within the error limit of the experimental value (Table 4). A natural bond order analysis of the transition state and the substrate indicates that the N9 is sp$^{1.89}$ hybridized at the transition state compared to sp$^{2.29}$ in the substrate; therefore significant re-hybridization occurs at the transition state. The crystal structure of *E. coli* MTAN in complex with a transition state analogue shows that the Oδ2 of Asp 197 and main chain carbonyl oxygen of Ile152 are hydrogen bonded to N7 and N6 of adenine, respectively (Lee et al., 2005). The H-bonding of N7 to Asp197 is favored by an increased pK$_a$ of N7 at the transition state due to flow of electrons from the ribosyl group into adenine following the cleavage of the N-glycosidic bond. The N7 protonated (neutral) adenine at the transition state forms a better leaving group than adenine anion, facilitating glycosidic bond cleavage. These interactions alter the conjugative system of the adenine ring and influence the hybridization of N9 and the 9-$^{15}$N KIE.

TABLE 4

Isotope Effects for the Transition State of *E. coli* MTAN Calculated at B3LYP/6-31G(d, p) and Comparison to Intrinsic KIE at pH 8.5.

| Position | Type of KIE | Intrinsic KIE | Calculated KIE |
|---|---|---|---|
| [1'-$^{14}$C] | primary | 1.004 | 1.004 |
| [2'-$^{3}$H] | β-secondary | 1.044 | 1.043 |
| [9-$^{15}$N] | primary | 1.018 | 1.021 |
| [1'-$^{3}$H] | α-secondary | 1.160 | 1.38 |
| [4'-$^{3}$H] | γ-secondary | 1.015 | 0.956 |
| [5'-$^{3}$H$_2$] | δ-secondary | 1.010 | 1.01 (proR) |
| | | | 0.99 (proS) |
| [Me—$^{3}$H$_3$] | remote | 1.051 | 1.069 |

Remote [4'-$^{3}$H] KIE. The C4'-H4' sigma bond is three bonds distant from the reaction center and it was expected that substitution of hydrogen with tritium at this position would not give a significant KIE. A modest KIE of 1.015 was measured experimentally for 4'-$^{3}$H MTA. However, the computed transition state that best matched the other KIEs predicted a large inverse isotope effect of 0.957 for 4'-$^{3}$H MTA. Analysis of the natural bond orbitals of the substrate and transition state predicted a large electron delocalization energy (6.59 kcal/mol) in the substrate for hyperconjugation from the lone pair (n$_p$) of O4' to the C4'-H4' anti-bonding orbital. No hyperconjugation was observed in the transition state for this interaction (less than <0.5 kcal/mol). Greater hyperconjugation between n$_p$ of O4' and σ* of C4'-H4' in the substrate relative to the transition state is translated into vibrational looseness to the C4'-H4' covalent bond in the substrate, giving the inverse calculated KIE in the modeled transition state. At the transition state the n$_p$ of O4' is delocalized towards the anomeric carbon both by hyperconjugation to the cationic C1' and overlap with the partially empty 2p$_z$ orbital of C1'. Calculations on 2-propanol, a secondary alcohol resembling a generic hydroxyl group in ribose, help explain the normal 4'-$^{3}$H KIE measured with MTAN. Ionization of the isopropanol hydroxyl gives a large (1.36) isotope effect on the equilibrium of ionization for the central CH bond (Lewis and Schramm, 2003). Hydroxyl deprotonation increases the ability of oxygen lone pairs to hyperconjugate into the antibonding (σ*) orbital of the geminal CH bond as well as to the vicinal antiperiplanar methyl CH bonds, although to lesser extent. This lowers the bond order of the geminal CH bond as well as the methyl CH bonds giving a significant isotope effect on the equilibrium of ionization. The crystal structure of *E. coli* MTAN with MT-ImmA, a transition state analogue inhibitor, shows that 3'-hydroxyl of ribose forms a 2.7 Å hydrogen bond with Glu174 and a similar H-bond with the catalytic site water (Lee et al., 2005). If hydrogen bonding partially deprotonates the 3'-hydroxyl group at the transition state to moderately increase electron delocalization from $n_p$ of O3' to σ* of vicinal C4'-H4', the interaction readily explains the modest KIE of 1.015 at $^3$H4' measured experimentally. Additional evidence for the importance of this 3'-OH interaction comes from the observation that 2'-deoxy-MTA is a good substrate, but 3'-deoxy-MTA is not (49) and that a Glu174Ala mutation abolishes catalytic activity (Lee, J. E., Luong, W., Huang, D. J. T, Cornell, K. A., Riscoe, M. K. and Howell, P. L. unpublished observations).

[5'-$^3$H] KIE. No significant KIE is predicated for a position removed by four bonds from the site of reaction and indeed a modest remote KIE of 1.010 was measured for 5'-$^3$H MTA. The magnitude of the 5'-$^3$H KIE for *E. coli* MTAN is small compared to KIE of some N-ribosyl transferases such as purine nucleoside phosphorylase and thymidine phosphorylase (Table 3). For human and bovine PNP the intrinsic KIE for [5'-$^3$H]inosine were 1.062 and 1.064 (Lewandowicz and Schramm, 2004), respectively, whereas for thymidine phosphorylase it was 1.061 for [5'-$^3$H]thymidine (Birck and Schramm, 2004a). In thymidine phosphorylase the entire [5'-$^3$H]isotope effect is at the step of substrate binding and is due to dihedral freezing of the 5'-hydroxyl (Birck and Schramm, 2004b). For PNPs with $S_N1$ transition states similar to *E. coli* MTAN, it is proposed that hydrogen bonding of the 5'-hydroxyl to histidine in the active site distorts the geometry of 5'-hydrogens at the transition state relative to the ground state giving rise to the observed KIE (Lewandowicz and Schramm, 2004). A 5'-methylthio group of MTA is different from the hydroxymethyl of inosine in hydrophobicity and lack of hydrogen bond potential. The 5'-$^3$H$_2$ KIE (the product of 5'-pro-R and 5'-pro-S hydrogen isotope effects) of 1.00 was computed using density functional methods (B3LYP/6-31G (d,p)). The 5'-pro-R and 5'-pro-S hydrogens behave differently to give isotope effects of 1.010 and 0.99 respectively. The normal isotope effect for the 5'-pro-R hydrogen is due to hyperconjugation between lone pair of sulphur and its antibonding sigma orbital. For the 5'-proS hydrogen the calculated inverse isotope effect is due to hyperconjugation from the sigma bond of the C5'-5' proS hydrogen to the antibonding orbital of C4'-C5'. KIE by definition refers to changes between reactant and transition state. Conformational freedom of the substrate in solution leads to cancellation of hyperconjugations due to averaging whereas the 5' region at the transition state is immobile for the short time span of the transition state. Dihedral freezing upon binding and during the transition state coupled with hyperconjugation effects described above are sufficient to explain the observed 5'-$^3$H KIE.

Remote Me-$^3$H KIEs. The methylthio group of 5'-methylthioadenosine is fixed in the active site of *E. coli* MTAN by hydrophobic interaction with non-polar residues including Met9, Ile50, Val102, Phe105 and Phe207 (Lee et al., 2005). In solution MTA will sample all C4'-C5'-S—$C^{Me}$ dihedral angle conformations since calculations suggest that the energetic barrier for full rotation of C4'-C5'-S—$C^{Me}$ is less than 0.7 kcal/mol. An isotope effect of 1.051 was measured for methyl-$^3$H$_3$ MTA. C—H bonds of the methyl group are 6 bonds removed from the N-ribosidic bond and a KIE at this position would be dictated by local effects rather than communication of electron structure from the transition state. The methyl isotope effect is likely to be an equilibrium isotope effect from binding of MTA to the enzyme and the subsequent restriction of C4'-C5'-S—$C^{Me}$ dihedral angle rotation and alteration of C—H vibrational modes. The thiol of the methylthio group contains lone pair electrons. When a CH bond is adjacent to a heteroatom with a lone pair, hyperconjugation with the antibonding orbital of the CH bond can decrease its bond order to give a normal isotope effect depending on the angle by which the CH bond subtends the lone pair electrons (Lewis and Schramm, 2001a, b). A natural bond orbital analysis of the transition state with fixed methyl group geometry suggests that the $n_p$ of sulphur hyperconjugates with the antibonding orbitals of three methyl CH bonds with the stabilization energy of 3.98, 4.00 and 1.03 kcal/mol, dependent on CH bond angles with respect to the lone pair on sulphur. The isotope effect calculated for three methyl CH bonds is 1.021, 1.031 and 1.016, to give an overall isotope effect of 1.069, similar to the isotope effect measured experimentally. The small difference in the calculated KIE can easily arise from uncertainty in accurately predicting the solution and enzymatic conformations of the methylthio group.

Figure 5:
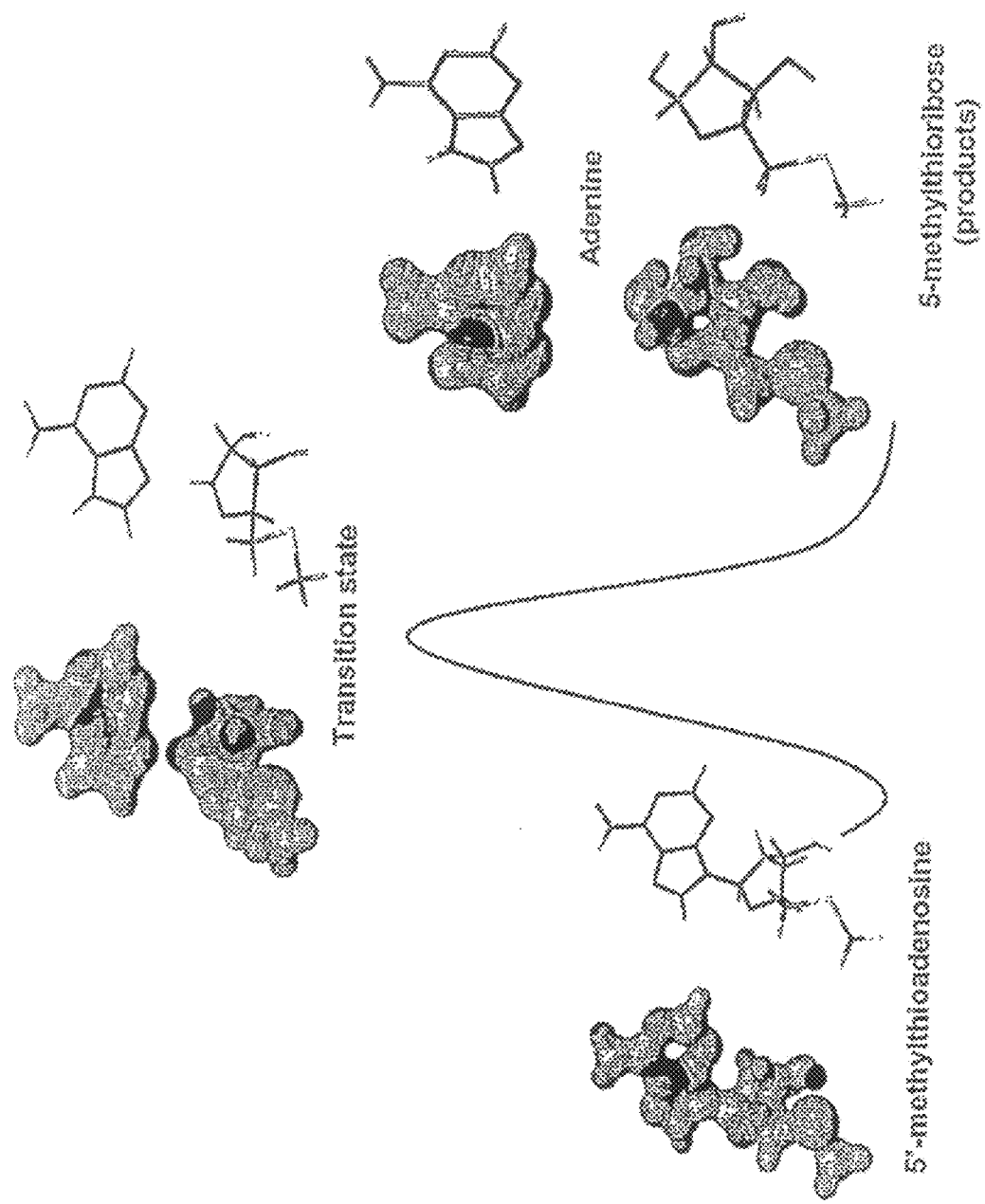
FIG. 5 is an illustration of a reaction coordinate showing the molecular electrostatic surface potential of 5'-methylthioadenosine (a substrate), the transition state and adenine with 5-methylthioribose (products). MEPs were calculated at HF/STO3G (Gaussian 98/cube) for the geometry optimized at the B3LYP/6-31G(d,p) level of theory and visualized with Molekel 4.0 (Flukiger et al., 2000) at a density of 0.008 electron/bohr. The stick models shown below on the right have same geometry as the MEP surfaces.

Molecular Electrostatic Potential Surface Analysis. The electrostatic potential surface of a molecule is the difference in the interaction energy of a point probe of unit charge between the nucleus and the electrons at a defined distance from the nucleus and therefore, is sensitive to the distribution of electrons on a molecule (Bagdassarian et al., 1996). The electrostatic potential of a substrate changes as it moves along the reaction coordinate, and each position on the reaction coordinate has its own characteristic distribution of electrons and thus a unique molecular electrostatic potential surface (MEP). The MEP surface is a defining attribute of the transition state along with bond distances and charges. The change in MEPs for substrate, transition state and products, reveals that the leaving group has higher electron density at the transition state and in the product as compared to the substrate due to flow of electrons from ribose during the conversion of substrate to transition state or products, as expected for $S_N1$ reactions (FIG. 5).

Stable Transition State Analogues of the Dissociative Oxacarbenium Ion Transition State of *E. coli* MTAN. At the transition state of MTAN the C1'-N9 glycosidic bond of MTA is 3.0 Å, a loss of 0.96 of the bond order relative to reactant (Table 2). This imparts an increased cationic character to C1' (the net charge on C1' increases from +0.25 to +0.50) and increased delocalization of electrons from the lone pairs of ring oxygen towards the reaction center. The charge on O4' increases from −0.59 in the reactant to −0.39 at the transition state. The O4'-C1' bond thus has partial double bond character and the C1' becomes more planar. Dissociation of the glycosidic bond at the transition state causes an increased $pK_a$ of N7, and N7 is protonated at the transition state to form a favorable hydrogen bond with Asp197. The transition state analogue inhibitors were designed to contain a cationic ribosyl analogue and an elevated $pK_a$ at N7. Replacing N9 of adenine with carbon (9-deazaadenine) creates a stable C—C glycosidic bond and alters the conjugative pattern to increase the $pK_a$ of N7 to >10 (Sauve et al., 2003). The MEP surface of the transition state was used to create similar inhibitors. MT-ImmA, MT-DADMe-ImmA, and pClPhT-DADMe-ImmA are all similar to the transition state (FIG. 6). The binding affinity of transition state analogue inhibitors is related to how closely their electrostatics matches that of the transition state. The MEPs of MT-DADMe-ImmA and pC1PhT-DADMe-ImmA are better matches to the MEP of the transition state than MT-ImmA, consistent with their increased binding affinity to *E. coli* MTAN (FIG. 6, Singh et al., 2005).

The first generation of transition state analogue inhibitors, Immucillins, incorporated the features of early ribooxacarbenium ion transition states. The N4' in Immucillins has as a $pK_a$ of 6.9 and is known to be cationic at the catalytic sites of N-ribosyltransferases (Sauve et al., 2003). Methylthio-Immucillin-A in the Immucillin series resembles MTA at an early transition state. It is a tight-binding slow onset inhibitor with an overall dissociation constant of 77 pM. The second generation transition state analogue inhibitors "DADMe-Immucillins" were designed to match the geometry and molecular electrostatic features of fully-dissociated ribooxacarbenium ion transition states (Lewandowicz et al., 2003). They include a pyrrolidine moiety as the ribooxacarbenium mimic and a methylene bridge between the ribooxacarebenium ion mimic and the 9-deazaadenine to provide geometric approximation for the fully-dissociative transition state of *E. coli* MTAN. MT-DADMe-ImmA is a transition state mimic because it incorporates the methylthio group, the cationic mimic of the ribooxacarbenium ion, a methylene bridge to give a 2.5 Å distance to approximate the 3 Å N-ribosidic bond of the transition state, and the elevated $pK_a$ at N7. It is a slow-onset inhibitor with an equilibrium dissociation constant of 2 pM (FIG. 6). The tightest inhibitor in the DADMe-Immucillin-A series was pC1PhT-DADMe-ImmA. It has a dissociation constant of 47 fM inhibitor and binds 91 million times tighter than the substrate S-adenosylhomocysteine ($K_m$ of 4.3 µM) and is one of the most powerful non-covalent inhibitors ever reported (Singh et al., 2003). The binding affinity of pC1PhT-DADMe-ImmA is within a factor of 1000 of the predicted binding affinity of the transition state calculated based on the $k_{cat}$ of the enzyme relative to chemical solvolysis.

Binding of Femtomolar Transition State Analogue Inhibitors. Defining features of the transition state include the cationic character of the sugar, increased $pK_a$ of N7, and the 3 Å distance between the ribooxacarbenium ion and N9 of adenine. Although the 4'-iminoribitol group of MT-ImmA is cationic ($pK_a$=6.9) to mimic the ribooxycarbenium ion nature of the transition state, the C1-C9 distance is only 1.5 Å in MT-ImmA, short of the 3 Å C1'-N9 bond in the transition state. In the crystal structure, the protonated 4'-iminoribitol group of MT-ImmA can be seen to attract the nucleophilic water towards the 4'-iminoribitol group (~3.1 Å). In structures with neutral substrate analogues of MTA, such as methylthiotubercidin (7-deaza MTA), the O4' ribosyl atom does not interact with the nucleophilic water, and is separated by ~3.6 Å in the crystal structure (Lee et al., 2003). It has been proposed that the nucleophilic water is deprotonated at the active site to form a strong electrostatic ion pair interaction with the cationic 4'-iminoribitol group. For DADMe-Immucillins the same features of the transition state account for their tight binding but they are better geometric and electrostatic mimics. The $pK_a$ of the 1'-pyrrolidine nitrogen is ~8.5 in similar compounds and are therefore cationic at neutral pH (Zhou et al., 2004). The presence of the cationic N1' atom and the deletion of the O2' hydroxyl, allows a better capture of the transition state features by allowing the nucleophilic water to move to within ~2.6 Å of the 1'-pyrrolidine nitrogen. The stronger electrostatic interaction between the pyrrolidine cation and the water nucleophile is proposed to be an important feature for action as transition state mimics (Lee et al., 2005).

Conclusions

Kinetic isotope effects and density functional calculations establish the transition state of *E. coli* MTAN to be highly dissociative with very low bond order to the leaving group, no significant bond order to the attacking water nucleophile and the ribosyl moiety to have significant oxacarbenium ion character. Transition state models and natural bond orbital analysis provide explanations for remote isotope effects, more than three bonds from the site of chemistry. The transition state structure obtained here provides a blueprint for the design of powerful transition state analogue inhibitors for *E. coli* MTAN. Molecular electrostatic potential maps of the transition state structure are compared to those for transition state analogue inhibitors. Increasing similarity between the experimentally determined transition state structure and inhibitors causes increased binding affinity. Understanding the transition state structure of *E. coli* MTAN provides additional support to the hypothesis that knowledge of transition state chemistry can be readily applied to the design of powerful transition state analogue inhibitors.

EXAMPLE 2

Transition State Analysis of *S. pneumoniae* 5'-Methylthioadenosine Nucleosidase Example Summary Kinetic isotope effects (KIEs) and computer modeling are used to approximate the transition state of *S. pneumoniae* 5'-methylthioadenosine/S-adenosylhomocysteine nucleosidase (MTAN). Experimental KIEs were measured and corrected for a small forward commitment factor. Intrinsic KIEs were obtained for [1'-$^3$H], [1'-$^{14}$C], [2'-$^3$H], [4'-$^3$H], [5'-$^3$H$_2$], [9-$^{15}$N] and [Me-$^3$H$_3$] MTAs. The intrinsic KIEs suggest an $S_N1$ transition state with no covalent participation of the adenine or the water nucleophile. The transition state was modeled as a stable ribooxacarbenium ion intermediate and was constrained to fit the intrinsic KIEs. The isotope effects predicted a 3-endo conformation for the ribosyl oxacarbenium-ion corresponding to H1'-C1'-C2'-H2' torsional angle of 70°. Ab initio Hartree-Fock and DFT calculations were performed to study the effect of polarization of ribosyl hydroxyls, torsional angles and the effect of base orientation on isotope effects. Calculations suggest that the 4'-$^3$H KIE arises from hyperconjugation between the lonepair ($n_p$) of O4' and the σ* (C4'-H4') antibonding orbital due to polarization of the 3'-hydroxyl by Glu174. A [methyl-$^3$H] KIE is due to hyperconjugation between $n_p$ of sulphur and σ* of methyl C—H bonds. van der Waal contacts increase the 1'-$^3$H KIE due to induced dipole-dipole interactions. The 1'-$^3$H KIE is also influenced by the torsion angles of adjacent atoms and by polarization of the 2'-hydroxyl. Changing the virtual solvent (dielectric constants) does not influence the isotope effects. Unlike other N-ribosyltransferases, N7 is not protonated at the transition state of *S. pneumoniae* MTAN. This feature differentiates the *S. pneumoniae* and *E. coli* transition states and explains the $10^3$-fold decrease in the catalytic efficiency for *S. pneumoniae* MTAN.

Kinetic isotope effects (KIEs) have been useful in the study of kinetics (Cleland, 2005; Bennet and Sinnot, 1986; Paneth, 1997), chemical equilibra (Anet at al., 1980; Lewis and Schramm, 2001), transition states (Craig et al., 1996; Singh et al., 2005a; Birck and Schramm, 2004; Lewandowicz, 2004), vibrational mode relaxations (Gambogi et al., 1993), tunneling (Cha et al., 1989; Johnsson et al., 1994; Xue et al., 2004), hyperconjugations (Lewis, 1959; Shiner, 1959) and ionization (Northcott and Robertson, 1969; Heys, 1987; Lewis and Boozer, 1952). KIEs are particularly useful for studying transition states (TS) of enzymatic reactions. Multiple KIEs provide a boundary condition for the quantum chemistry calculations of a transition state. Iteratively applied constraints are then used to match the theoretical KIEs to the experimental ones. Transition state analogues capture catalytic forces imposed by enzymes and are powerful inhibitors (Wolfenden, 1969; Wolfenden and Snider, 2001; Miller and Wolfenden, 2002). Knowledge of enzymatic transition states has lead to the design of some of the tightest binding non-covalent inhibitors known, with dissociation constants in the femtomolar range and some of which are in clinical trials (Singh et al., 2005b; Miles et al., 1998; Kicska et al., 2003; see http://www.biocryst.com).

Isotope effects (IEs) arise from altered bond vibrational environments. Binding isotope effects (BLEs) report equilibrium bond changes, for example, on formation of a Michaelis complex. Competitive KIEs or isotope effects on (V/K) are the isotope effect associated with the first irreversible step in enzyme catalyzed reactions and they approximate intrinsic KIEs when the first irreversible step is the chemical step. Partially irreversible steps between the substrate and the transition state can suppress intrinsic KIEs, but suppressed isotope effects can be corrected by isotope partition methods (Rose, 1980). Intrinsic KIEs are directly associated with changes in the normal modes between reactants and the transition states.

Figure 7:
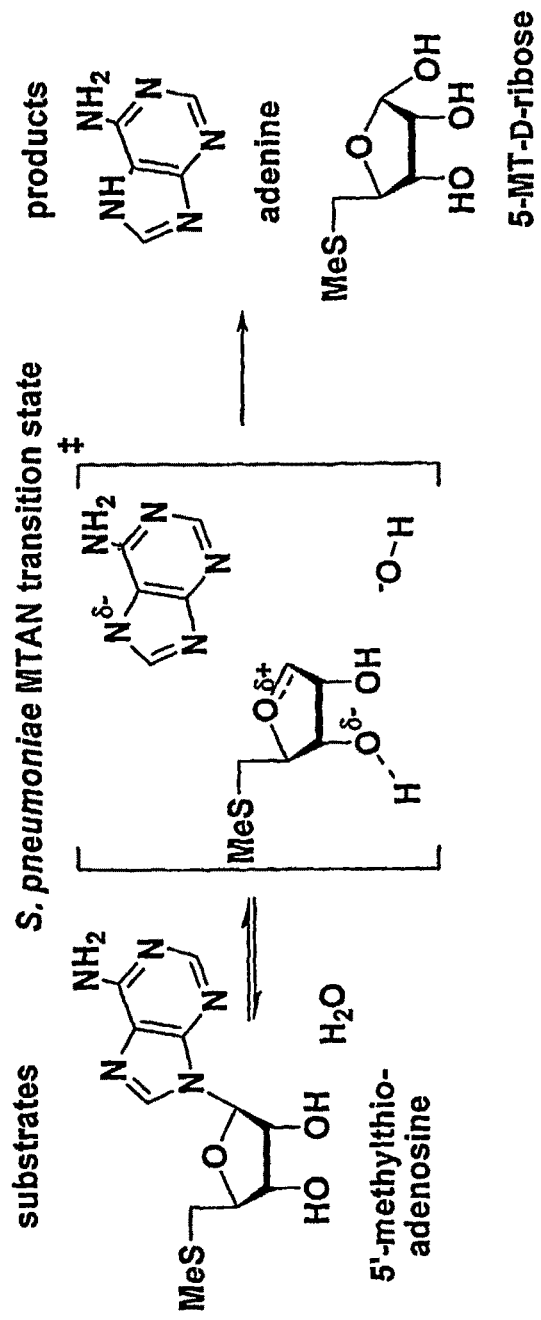
FIG. 7 is a diagram showing the hydrolysis of MTA by S. pneumoniae MTAN and the proposed transition state of the reaction.

In this study multiple isotopomers of MTA were used to study the transition state of 5% methylthioadenosine/S-adenosylhomocysteine (MTAN) of S. pneumoniae, a bacterial enzyme involved in polyamine biosynthesis, quorum sensing, purine and methionine salvage (Schauder et al., 2001; Ragione et al., 1985; Miller and Duerre, 1968; Tabor and Tabor, 1983; Xavier and Bassler, 2003; Parsek et al., 1999; Withers et al., 2001; Miller et al., 2002). It catalyzes the physiologically irreversible hydrolytic cleavage of the N-glycosidic bonds of 5% methylthioadenosine (MTA) or 5"-S-adenosylhomocysteine to 5"-methylthioribose, S-ribosylhomocysteine and adenine (FIG. 7). Adenine is salvaged by adenine phosphoribosyltransferase (APRTase) and methylthioribose is converted to methionine in multiple steps (Myers and Abeles, 1989). MTAN has been proposed to be a target for the design of antimicrobial agents because of its involvement in the synthesis of autoinducers2 (AI2). AI2s are quorum sensing molecules formed from S-ribosylhomocysteine and used by bacteria to signal biofilm formation, causing prolonged chronic infections. Mutational studies in Haemophilus influenzae, Streptococcus pneumoniae, Streptococcus pyogenes, and Enterococcus faecalis have suggested that mutations to the pfs gene (pfs gene encodes for MTAN) may reduce pathogenicity and the enzyme has been targeted for the design of antimicrobial agents (Cadieux et al., 2002; Riscoe et al., 1989; Sufrin et al., 1005).

The transition state of E. coli MTAN has a dissociative $S_N1$ transition state with full cleavage of the N-glycosidic bond and no participation of the attacking nucleophile. The adenine leaving group is activated by N7 protonation, a recurring theme in the acid-catalyzed cleavage of purine nucleosides. Other purine N-ribosyl transferases place an aspartate residue close of N7 (Asp197 for MTANs [Singh et al., 2005b], Asp220 in MTAP [Singh et al., 2004] and Asp198 in PNP [Shi et al., 2001a]), which are proposed to protonate N7 at the transition states. Protonation of N7 makes the purine group electron deficient, weakening the N-ribosidic bond, and facilitates the reaction by forming neutral adenine as the leaving group.

In this study the transition state of S. pnewnoniae MTAN is explored using $^3H$, $^{14}C$ and $^{15}N$ KIEs and model the transition state as an intermediate using high level density functional theory. The origin of remote KIEs, the effect of 2'- and 3'-hydroxyl ionizations, and the effects of altered torsion angles are investigated. The difficulty of explaining the large 1'-$^3H$ isotope effect (IE) observed in computational modeling of the dissociative $S_N1$ transition states is addressed. Leaving group activation and hyperconjugation effects are explored to explain local and remote isotope effects.

Material and Methods

Expression of S. pneumoniae MTAN. Expression of S. pneumoniae MTAN in E. coli has been described (Singh et al., 2006). Briefly, the gene for S. pneumoniae MTAN was obtained by PCR amplification from genomic DNA and cloned into the pET23a(+) plasmid (Novagen). The MTAN gene was expressed in E. coli strain BL21 (DE3) at 37° C. in the presence of 50 μg/mL carbenicillin for 4 hours after induction with IPTG. The expressed protein was purified on $Ni^{2+}$-NTA His-Bind affinity columns and eluted with imidazole. Active fractions were further purified on a Superdex 200 gel filtration column. The purified protein was concentrated to 15 mg/mL and stored at −70° C.

Enzymes and reagents for ATP synthesis. The reagents and the enzymes used in the synthesis of ATPs from glucose have been described previously (Singh et al., 2005a; Shi et al., 2001b; Parkin et al., 1984; Rising and Schramm, 1994).

Enzymes and reagents for MTA synthesis. Hexokinase from Saccharomyces, myokinase from chicken muscle, pyruvate kinase, glucose-6-phosphate dehydrogenase (G6PDH), phosphoriboisomerase and phosphogluconic dehydrogenase were purchased from Sigma. Adenine phosphoribosyltransferase (APRTase) from yeast (APRTase) was reported previously (Parkin et al., 2006), 5'-phosphoribosylpyrophosphate synthetase (PRPPase) was a generous gift from Paul Berti (McMaster University, Hamilton, ON) and SAM synthetase was gifted to us by George D. Markham (Fox Chase Cancer center Institute, Philadelphia, Pa.). ATP, monopotassium α-ketoglutrate, glucose, β-nicotinamide adenine dinucleotide phosphate sodium salt ($NADP^+$), phosphoenolpyruvic acid cyclohexylammonium salt (PEP), glycylglycine and $_{DL}$-dithiothreitol (DTT) were purchased from Sigma.

Synthesis of radiolabeled MTAs. Isotopically labeled [1'-$^3H$] MTA, [1'-$^{24}C$] MTA, [2'-$^3H$] MTA, [3'-$^3H$] MTA, [4'-$^3H$] MTA, [5'-$^3H_2$] MTA and [Methyl-$^3H_3$] MTA were synthesized from the corresponding ATP molecules in two steps using a procedure described elsewhere (Singh et al., 2005a).

Kinetic isotope effect measurements. Competitive kinetic isotope effects (KIEs) were measured by comparing the products formed from pairs of isotopically labeled substrates, as described previously (Singh et al., 2005a). The KIEs were corrected to 0% hydrolysis by the equation $$KIE = \frac{\ln(1-f)}{\ln\left[(1-f)\frac{R_f}{R_o}\right]}$$

Where f is the fraction of reaction progress and $R_f$ and $R_o$ are ratios of heavy to light isotope at partial and total completion of reaction, respectively.

Figure 8:
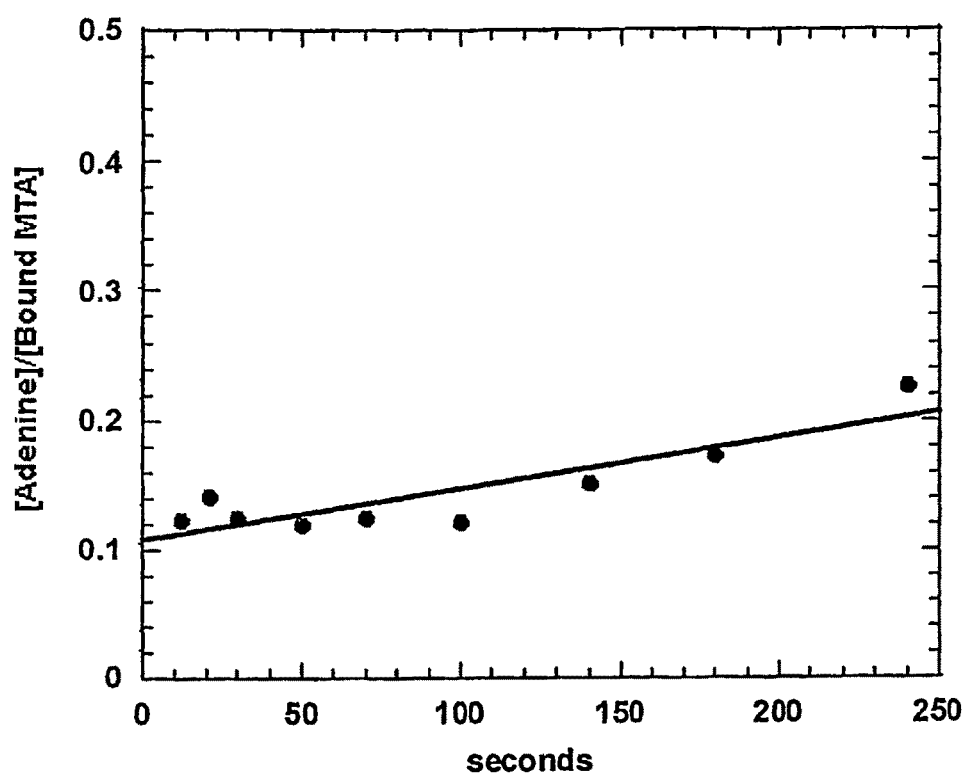
FIG. 8 is a graph of experimental results showing the forward commitment to catalysis for the MTAN-MTA complex. The complex of S. pneumoniae MTAN and $^{14}$C-MTA was diluted with a large excess of unlabeled MTA at 3 sec. Subsequent reaction partitions bound $^{14}$C-MTA to product (forward commitment) or permits release into free, unbound MTA. Zero commitment extrapolates through the origin while full (100%) commitment would intersect at 1.0 on the ordinate as indicated by the arrow. The forward commitment was calculated by plotting the amount of labeled adenine formed following addition of chase solution divided by amount of labeled MTA on the active site before dilution with chase solution and extrapolating this ratio back to zero time. The line is drawn from an ordinary least square fit of the data, y errors only. The intercept value is 0.108±0.006.
Figure 11:
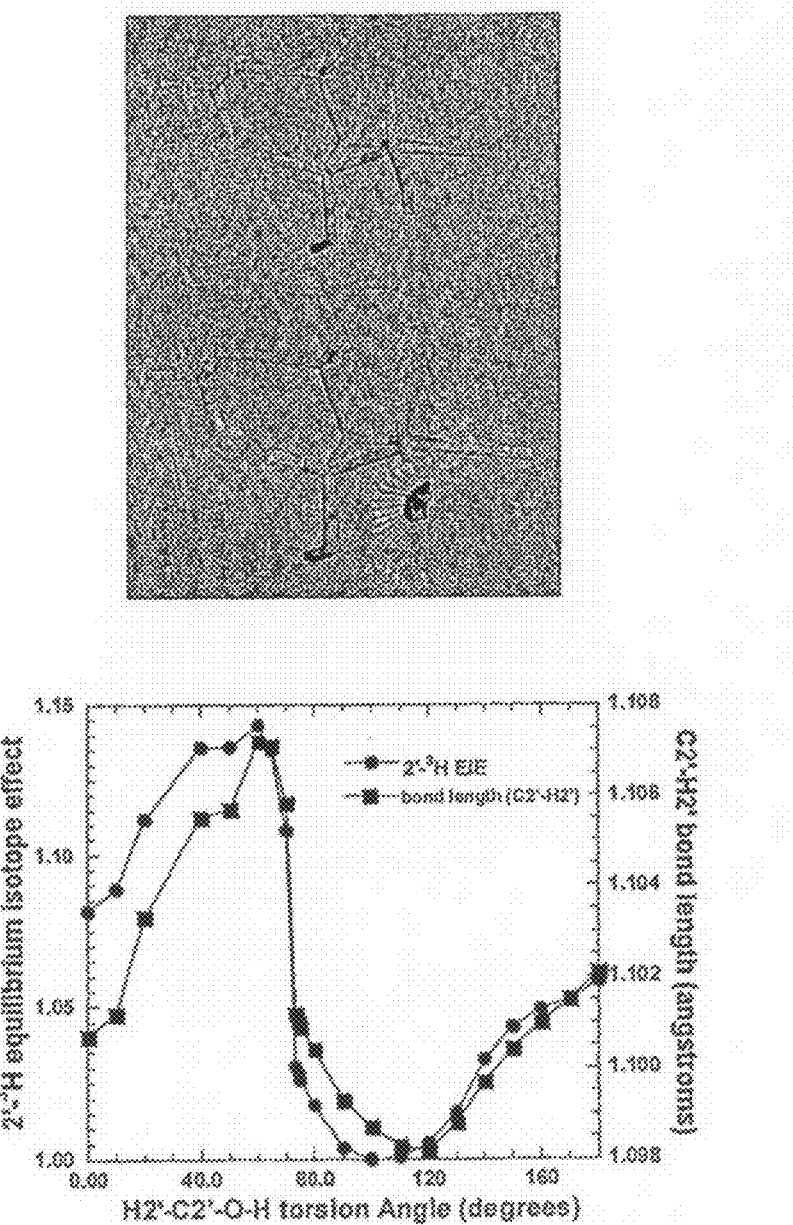
FIG. 11 is a model and a graph of experimental results showing the relative change in 2'-$^3$H isotope effects (Ms) and C2'-H2' bond length due to rotation of H2'-C2'-O—H torsion angle. The isotope effects are calculated with respect to the H2'-C2'-O—H torsion angle of 90°.
Figure 16:
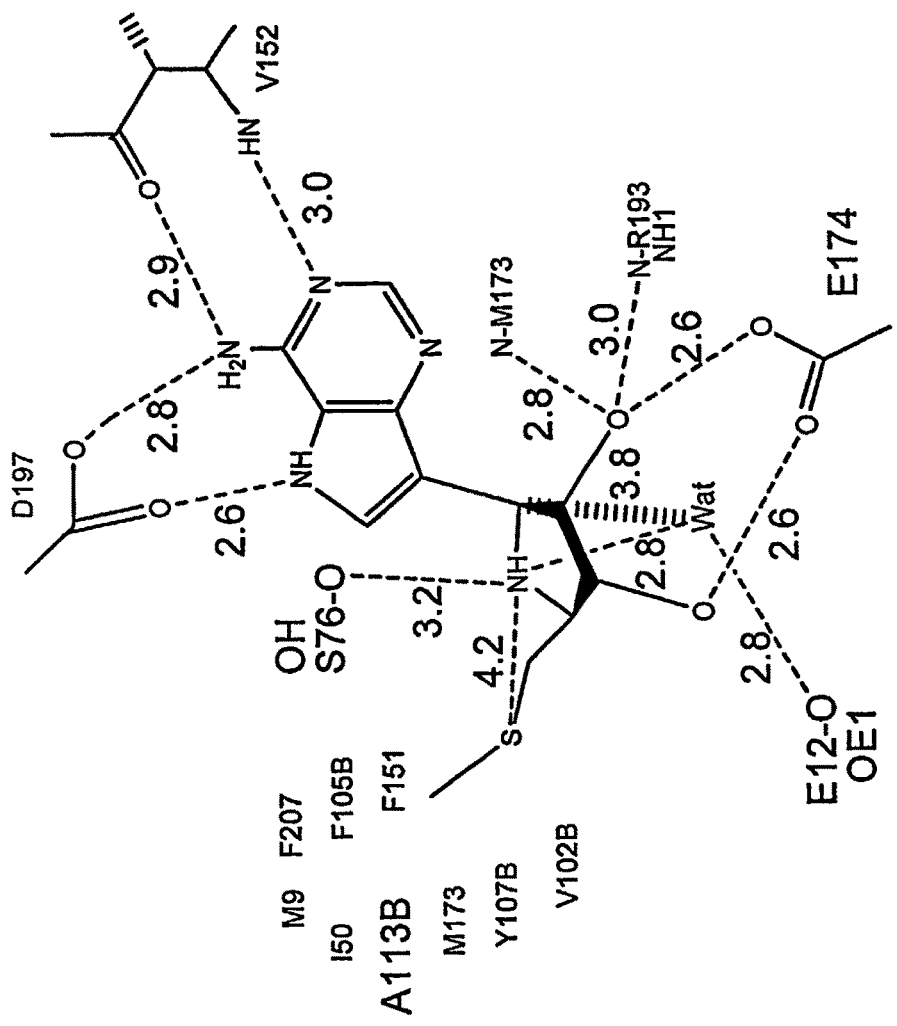
FIG. 16 is a diagram showing the contacts made by MT-ImmA, a transition state analogue with the residues in the active site of *S. pneumoniae* MTAN (adapted from Shi et al., 2001a).

Commitment to catalysis. The forward commitment to catalysis for S. pneumoniae MTAN was measured by the isotope-trapping pulse-chase method (Rose, 1980). The pulse solution (100 mM HEPES pH 7.5, 50 mM KCl, 170 μM of [$8^{24}C$] MTA) was mixed with enzyme (17 μM) to give a 100 μl reaction mixture. After 3 s (0.6 of one catalytic turnover at $k_{cat}$ of 12 $min^{-1}$) the solution was diluted with 900 μL of solution containing 2.7 mM unlabeled MTA in 100 mM HEPES pH 8.5 and 50 mM KCl (the chase solution). Samples of 100 μL were quenched with 1N HCl starting at 10 s up to 120 s (FIG. 8). The adenine product was isolated by reverse phase HPLC using C-18 Deltapak column by 25% methanol in 50 mM ammonium acetate pH 5.0 and quantitated by scintillation counting. The forward commitment to catalysis is (bound MTA that is converted to product) divided by (labeled substrate bound to the enzyme).

Computation of transition states. The in vacuo determination of the transition state for hydrolysis of MTA used hybrid density functional methods implemented in Gaussian03 (Frisch, 2003). The transition state was modeled as a ribooxacarbenium ion using one-parameter Becke (B1) exchange functional, the LYP correlation functional and standard 6-31G* basis set (Becke, 1996). The same level of theory and basis set were used for optimization of substrate and products as well as for the computation of bond frequencies. The 5'-methylthio group was constrained during calculations by fixing the O4'-C4'-C5'-S and C4'-C5'-S—$C^5$ dihedral angles. The properties of the leaving group at the transition state were modeled separately.

EIEs were calculated from the computed frequencies using ISOEFF 98 software (Anisimopv and Paneth, 1999). All calculated 3N-6 vibrational modes were used to calculate the isotope effects, but only those that exhibit shifts due to isotopic substitution contribute to the isotope effect. The isotope effects were calculated at the temperature of 298 K.

After each cycle of optimization, calculation of bond frequencies and isotope effects, geometric constraints applied to substrate and the transition state were optimized iteratively until the calculated equilibrium isotope effects for the transition state intermediate matched the experimental intrinsic KIEs. Constrained molecules impose energetically unfavorable positions relative to vacuum conditions for transition state searches. These reflect the forces imposed by the enzymatic environment. Clearly, this approach yields an approximation of the transition state, as do all computational methods.

Natural Bond Orbital (NBO) calculations. The natural bond orbital (NBO) calculations were performed on optimized structures by including the pop=(nbo, full) keyword in the route section of input files.

Calculations of molecular electrostatic potential surface. The molecular electrostatic potential (MEP) surfaces were calculated by the CUBE subprogram of Gaussian03. The formatted checkpoint files used in the CUBE subprogram were generated by full or constrained geometry optimization at B1LYP level of theory and 6-31G* basis set. Substrate, the transition state treated as an intermediate and the transition state analogues MEP surfaces were visualized using Molekel 4.0 (Fltikiger et al., 2000) at a density of 0.008 electron/bohr (Bagdassarian et al., 1996).

Semiempirical, Ab initio and DFT calculations. The calculations described below were performed at density function level of theory using B1LYP/6-31G* unless otherwise indicated. The output of NBO calculations was used to obtain the relative energy of hyperconjugation, sigma and sigma* orbital occupancy, charge and bond order.

A. 5-Methylthioribooxacarbenium ion. MTA at the transition state produced by *S. pneumoniae* MTAN was used to simulate the effect of the H1'-C1'-C2'-H2' dihedral angle on the 2'-$^3$H EIE. Remote geometry (O4'-C4'-C4'-S and C4'-C5'-S—$C^{Me}$ torsion angles) was constrained to ensure reasonable analogy between structures as the dihedral angle was varied. Isotope effects were computed for each torsion angle.

B. 5'-Meththioribooxacarbenium 2'-hydroxyl polarization. The effect of 2% hydroxyl polarization on 1'-$^3$H, 2'-$^3$H and 3'-$^3$H EIEs was explored by the computational methods described above. The H1'-C1'-C2'-H2' torsion angle was fixed at 70°, where it generates a 2'-$^3$H EIE similar to the intrinsic 2'-$^3$H KIE. A hydroxyl anion was stepped closer to the 2'-OH to change the O—O bond distance in steps of 0.2 Å, each time performing an energy optimization. Interaction energy and isotope effect were determined for each distance. Remote geometry was constrained at the dihedral angles described above. A similar calculation explored the effect of polarization of the 3'-hydroxyl on the 4'-$^3$H EIE. In these calculations the hydroxyl anion was positioned such that the $O_{sugar}$—$H_{sugar}$—$O_{hydroxyl}$—$H_{hydroxyl}$ torsion angle was 180°.

C. tetrahydro-2-((methylthio)-methyl)furan. This model molecule was used to study the effect of rotation of C4'-C5'-S—$C^{Me}$ torsion angle on the isotope effects of the methyl hydrogens. A 360° scan of the C4-C5-S—$C^{Me}$ torsion angle was performed. Isotope effects and NBO analyses were computed at each step. The O4'-C4'-C5'-S torsion angle was constrained to fix the 5'-methylthio relative to the furan ring and O4'-C1'-C2'-C3' was constrained to prevent alteration in the ring pucker.

D. Solvation modeling. Solvation effects were examined by the Self Consistent Reaction Field (SCRF) method (Cramer and Truhlar, 1999) using the polarization continuum model implemented in Gaussin03 (Frisch, 2003). The homogenous dielectric environment is simulated by a virtual solvent characterized by the effective dielectric constant, $\in_{eff}$. Substrate was optimized in the dielectric environment of water with dielectric constant of 78.8, whereas the transition state was optimized in the presence of solvent with dielectric constants ranging from 4.9 of chloroform (similar to a dielectric constant of 4 assumed for the catalytic site) to that of 78.8 for water.

F. Effect of base orientation on 1'-$^3$H EIE. The 1'-$^3$H conformational equilibrium isotope effect was explored by examining the effect of the O4'-C1'-N9-C8 dihedral angle rotation in MTA on the 1'-$^3$H EIE. The calculations were performed at the Hartree-Fock level of theory (HF/6-31G*). The output was used to evaluate the relative change in 1'-$^3$H EIE with respect to orientation of base and the bond frequencies used in the calculation of isotope effects were not scaled. The ribose ring pucker and the 5'-methylthio group were constrained using the torsional angles described above.

G. $^{15}$N isotope effects and adenine protonation. Isotope effects ($^{15}$N9, $^{15}$N7, $^{15}$N1., and $^{15}$N3) were calculated for adenine mono-protonated at N1, N3, N7 or N9 as well as for the unprotonated adenine.

Results

Experimental Kinetic Isotope Effects. Kinetic isotope effects were measured for the *S. pneumoniae* MTAN-catalyzed hydrolysis of MTA to adenine and 5-methylthioribose using substrate competition experiments. The observed isotope effects give (V/K) isotope effects that include contribution from forward commitment factors. The hydrolytic reaction catalyzed by *S. pneumoniae* MTAN is physiologically irreversible; therefore reverse commitment is unlikely. Observed KIEs that include contribution from the forward commitment are listed in Table 5. These KIEs report vibrational changes between MTA free in solution and at the transition state. Irreversible steps before the chemical step obscure the intrinsic KIEs. Since the measured KIEs are in the range observed for intrinsic KIEs for other N-ribosyl transferases, forward commitment factor are modest.

TABLE 5

Kinetic Isotope Effects (KIEs) measured at pH 7.5 for
hydrolysis of MTA catalyzed by S. pneumoniae MTAN

| Substrate | Type of KIE | Experimental KIE[a] | Intrinsic KIEs |
|---|---|---|---|
| [1'-$^3$H] and [5'-$^{14}$C] MTA | α-secondary | 1.210 ± 0.002 | 1.230 ± 0.002 |
| [1'-$^{14}$C] and [5'-$^3$H] MTA | primary | 1.000 ± 0.005[a] | 1.000 ± 0.005 |
| [2'-$^3$H] and [5'-$^{14}$C] MTA | β-secondary | 1.085 ± 0.002 | 1.094 ± 0.002 |
| [9-$^{15}$N/5'-$^{14}$C]/[5'-$^3$H]MTA | primary | 1.033 ± 0.004[b] | 1.036 ± 0.004 |
| [4'-$^3$H] and [5'-$^{14}$C] MTA | γ-secondary | 1.011 ± 0.005 | 1.012 ± 0.005 |
| [5'-$^3$H] and [5'-$^{14}$C] MTA | δ-secondary | 1.017 ± 0.002 | 1.019 ± 0.002 |
| [Me—$^3$H] and [5'-$^{14}$C] MTA | remote | 1.050 ± 0.002 | 1.055 ± 0.002 |

Experimental KIEs are corrected to 0% substrate depletion.
[a]The 1'-$^{14}$C KIE was corrected for 5'-$^3$H KIE according to expression KIE = KIE$_{observed}$ × 5'-$^3$H KIE.
[b]The 9-$^{15}$N KIE was corrected for 5'-$^3$H KIE according to expression KIE = KIE$_{observed}$ × 5'-$^3$H KIE.

KIEs were 1.21 for [1'-$^3$H], 1.085 for [2'-$^3$H], and 1.033 for [$^{15}$N9]. These large isotope effects are indicative of a small commitment factor and substantial vibrational changes experienced by atoms close to the reaction center at the transition state compare to unbound substrate in solution (Lewis and Schramm, 2003). Surprisingly, a large intrinsic KIE of 1.050 was observed for the [Methyl-$^3$H$_3$] of the methylthio group, even though it is four bonds from the reaction center.

Commitment Correction and Intrinsic KIEs. Forward commitment for S. pneumoniae MTAN was measured at pH 7.5 using the isotope trapping method (Rose, 1980). The external forward commitment factor of 0.108±0.006 for S. pneumoniae MTAN establishes that binding of MTA to the enzyme at pH 7.5 is partially committed (FIG. 8). The $^T$K$_{eq}$ for the MTAN reaction is assumed to be near unity since the anomeric carbon is sp$^3$-hybridized in both reactant and product. The intrinsic isotope effects for reversible reaction are related to isotope effect on $^T$(V/K) by the expression $$^T(V/K) = \frac{^Tk + C_f + C_r{}^TK_{eq}}{1 + C_f + C_r}$$

Where $^T$(V/K) is an observed tritium isotope effect, $C_f$ is the forward commitment for catalysis, $C_r$ is the reverse commitment to catalysis, $^T$K$_{eq}$ is the equilibrium isotope effect, and $^T$k is the intrinsic isotope effect (Northrop, 1975). The reaction catalyzed by S. pneumoniae MTAN is irreversible under initial rate conditions therefore the above expression can be reduced to;

$$^T(V/K) = \frac{^Tk + C_f}{1 + C_f}.$$

Intrinsic isotope effects can be obtained from the observed isotope effects (Table 5).

Correction for Remote Label KIEs. In experiments measuring the tritium KIEs, [5'-$^{14}$C] MTA was used as a remote label for lighter isotopes. The isotope effect at 5'-$^{14}$C was assumed to be unity because it is three bonds distant from the reaction center and $^{14}$C does not report isotope effects for geometric changes, unlike remote tritium labels.[8,9] For measuring 1'-$^{14}$C and 9-$^{15}$N KIEs, [5'-$^3$H$_2$] MTA was used as remote label. The KIE for 1'-$^{14}$C and 9-$^{15}$N were corrected for the remote label KIE as significant remote KIEs are obtained with 5'-$^3$H$_2$ and 4'-$^3$H, even though these atoms are four and three bonds away from the reaction center.

Computational Modeling of the Transition State for S. pneumoniae MTAN. The initial ab initio transition state of S. pneumoniae MTAN was modeled by including the leaving group and the nucleophile and had a single imaginary frequency of 397 i cm$^{-1}$, corresponding to the decomposition mode. The transition state structure corresponding to this imaginary frequency had an S$_N$2-like conformation with significant bonds to both the leaving group and the nucleophile. This transition state predicted a large isotope effect for [1'-$^{14}$C] MTA, characteristic of S$_N$2 transition states. The 1'-$^{14}$C KIE of unity for S. pneumoniae MTAN establishes a transition state closely related to an isolated ribooxacarbenium-ion. Subsequent transition state calculations did not include the leaving group or the nucleophile.

Intrinsic KIEs of 1.036 for [9-$^{15}$N] MTA, 1.00 for [1'-$^{14}$C] MTA and a large α-secondary intrinsic KM of 1.23 for [1'-$^3$H]MTA suggest a fully-dissociative S$_N$1 transition state for S. pneumoniae MTAN. The α-primary KM of unity for [1'-$^{14}$C] MTA indicates insignificant bond order to the leaving group and the attacking water nucleophile and little reaction coordinate motion. Fully-dissociative S$_N$1 transition states can be modeled as oxacarbenium ion intermediates (Lewandowicz and Schramm, 2004). The transition state was modeled using B1LYP level of theory and 6-31G(d) basis set implemented in Gaussian03. During the calculations the 5'-methylthio group was constrained using the torsion angle from the crystal structure of S. pneumoniae MTAN with a transition state analogue (MT-ImmA) (Lee et al., 2005). The H1'-C1'-C2'-H2', O4'-C4'-C5'-S and C4'-C5'-S—C$^S$ torsion angles were iteratively optimized until the calculated EIEs closely approximated the intrinsic KIEs. The leaving group adenine at the transition state was modeled separately (discussed below in context with $^{15}$N9). The effect of basis set and the level of theory on the calculated isotope effects are shown in Table 6 and properties of the transition state are listed in Table 7.

TABLE 6

Effect of theory and basis set on calculated equilibrium isotope effects (EIEs) for the transition state of *S. pneumoniae* MTAN.

|  |  |  | Gas Phase | | | | | | |
|---|---|---|---|---|---|---|---|---|---|
|  |  |  | Hartree-Fock | | | B1LYP | | B3LYP | |
| Label | Expt[a] | PM3 | 3-21G | 6-31G(d) | 6-31G(d, p) | 6-31G(d) | 6-31G(d, p) | 6-31G(d) | 6-31G(d, p) |
| [1'-$^3$H] | 1.23 | 1.17 | 1.510 | 1.47 | 1.48 | 1.46 | 1.45 | 1.42 | 1.44 |
| [1'-$^{14}$C] | 1.00 | 1.006 | 1.011 | 1.007 | 1.007 | 1.00 | 1.000 | 1.00 | 1.00 |
| [2'-$^3$H] | 1.094 | 1.210 | 1.053 | 1.082 | 1.089 | 1.094 | 1.108 | 1.085 | 1.10 |
| [4'-$^3$H] | 1.012 | 1.070 | 1.017 | 0.960 | 0.961 | 0.950 | 0.950 | 0.950 | 0.930 |
| [9-$^{15}$N] | 1.036 | 1.021 | 1.035 | 1.031 | 1.024 | 1.035 | 1.030 | 1.028 | 1.028 |
| [5'-$^3$H] | 1.019[b] | 1.009[c] | 1.031[c] | 0.989[c] | 0.985[c] | 1.002[c] | 1.00[c] | 0.992 | 0.990[c] |
| -pro(R) |  | 0.996 | 1.047 | 1.014 | 1.012 | 1.022 | 1.020 | 1.021 | 1.019 |
| -pro(S) |  | 1.013 | 0.985 | 0.976 | 0.974 | 0.980 | 0.980 | 0.972 | 0.972 |
| [Me—$^3$H] | 1.055[d] | 1.053[e] | 1.079[e] | 1.050[e] | 1.067[e] | 1.045[e] | 1.035[e] | 1.017[e] | 1.034[e] |
| $^1$A |  | 0.980 | 1.015 | 0.975 | 0.994 | 0.990 | 0.99 | 0.980 | 0.990 |
| $^2$B |  | 1.016 | 1.041 | 1.017 | 1.014 | 1.011 | 1.01 | 1.010 | 1.010 |
| $^3$C |  | 1.057 | 1.022 | 1.059 | 1.059 | 1.044 | 1.035 | 1.028 | 1.034 |

Equilibrium isotope effects (EIEs) calculated for the transition state of *S. pneumoniae* MTAN are shown at various levels of theories and the basis set.
[a]Experimental intrinsic KIEs,
[b]Intrinsic [5'-$^3$H$_2$] KIE,
[c]Overall calculated 5'-$^3$H isotope effect obtained by multiplying 5'-proR and 5'-proS $^3$H isotope effects,
[d][Me—$^3$H$_3$] Intrinsic KIE,
[e]Overall calculated [Me—$^3$H] KIE from three methyl hydrogens, .
[1,2,3]Three methyl hydrogens. Frequencies were scaled prior to the calculation of isotope effects.

TABLE 7

Geometric and electronic changes in representative models of the substrate and the transition state calculated using B1LYP/6-31G* (SP_MTAN).

| Bond | | | Bond Order | Hyperconjugation (kcals/mol)[b] | | | | | Orbital Changes[c] | | | |
|---|---|---|---|---|---|---|---|---|---|---|---|---|
|  |  |  | Change[a] | Substrate | | TS | | |  | GS | Carbon | TS | Carbon |
| Type | Bond Length | | | | | | | | | | | | |
| cont.(%) | GS | TS | Δ(σ – σ*) | σ→ | →σ* | σ→ | →σ* | ΔΣ(TS – GS) | hybrid | cont.(%) | hybrid | cont(%) |
| C1'—H1' | 1.0938 | 1.0905 | −0.01410 | 10.87 | 8.26 | 8.42 | 8.70 | −1.28 | sp$^{2.82}$ | 62.80 | sp$^{1.84}$ | 63.70 |
| C2'—H2' | 1.0964 | 1.1003 | +0.02739 | 5.47 | 11.54 | 14.16[d] | 8.51 | −0.11 | sp$^{2.69}$ | 62.18 | sp$^{2.89}$ | 64.59 |
| C4'—H4' | 1.0980 | 1.0883 | −0.01407 | 8.85 | 12.50[e] | 8.81 | 5.59 | 3.60 | sp$^{3.01}$ | 61.81 | sp$^{2.68}$ | 64.63 |
| C1'—N9 | 1.4564 | NA | NA | 9.02 | 27.41 | NA | NA | NA | sp$^{3.26}$ | 35.72 | NA | NA |
| C5'—H5'(R) | 1.0931 | 1.0947 | −0.01750 | 5.18 | 4.27 | 3.87 | 6.60[g] | 4.39 | sp$^{3.04}$ | 63.81 | sp$^{3.13}$ | 63.64 |
| C5'—H5'(S) | 1.0935 | 1.0915 | −0.00092 | 3.62 | 5.21[h] | 4.29 | 3.77 | −0.30 | sp$^{2.92}$ | 63.13 | sp$^{2.79}$ | 64.57 |
| C$^S$—H(A) | 1.0920 | 1.0902 | +0.00181 | 2.45 | 1.21 | 0.74 | 2.76[i] | 1.18 | sp$^{2.96}$ | 62.78 | sp$^{2.76}$ | 63.74 |
| C$^S$—H(B) | 1.0926 | 1.0913 | −0.00629 | 0.00 | 4.20 | 0.58 | 1.20[i] | 0.01 | sp$^{2.82}$ | 62.48 | sp$^{2.84}$ | 62.31 |
| C$^S$—H(C) | 1.0918 | 1.0902 | −0.00360 | 0.70 | 4.70[j] | 1.32 | 2.60[i] | −1.81 | sp$^{2.78}$ | 62.36 | sp$^{2.78}$ | 63.25 |
| C3'—H3' | 1.0936 | 1.0892 | −0.00699 | 7.92 | 10.95 | 5.38 | 9.15[k] | 1.29 | sp$^{2.72}$ | 63.13 | sp$^{2.51}$ | 64.41 |

[a]Calculated by subtracting the number of electrons occupying the σ* orbital from the number occupying the σ orbital and listed as change between Substrate and Transition state (TS) (Substrate-TS).
[b]Sum of second order perturbation contributions calculated by NBO analysis. Cutoff = 0.5 kcals/mol.
[c]Hybridization of the carbon atom and contribution of the carbon atom to the bond in percent. GS = ground state of substrate, TS = transition state. Lp1 is the sp-type lone pair; and Lp2 is p-type lone pair:
[d]Lp2(C1'); [j]Lp(O3'); [g]Lp2(S); [i]Lp2(S); [k]Lp2(O3') are better acceptors in the transition state; While [e]Lp2(O4'); [h]Lp2(S); [j]Lp2(S) are better acceptors in the substrate.

The H1'-C1'-C2'-H2' dihedral angle and the 2'-$^3$H EIE. The β-secondary 2'-$^3$H isotope effect arises from the positive hyperconjugation of σ (C2'-H2') bonding electrons to the partially empty p-orbital on the adjacent anomeric carbon in reactions involving carbocation-like transition states. The 2'-$^3$H EIEs correlates inversely with the occupancy of σ (C2'-H2') orbital on the anomeric carbon (FIG. 9). The isotope effect is small inverse (~1%) between 0° and 45°, and increases steeply between 50° and 80° to a maximum value of 1.12 at a H1'-C1'-C2'-H2' torsional angle of 90°, suggesting maximum overlap of σ (C2'-H2') bonding orbitals with the p-orbital on the anomeric carbon.

Polarization of the 2'-hydroxyl. Polarization of an OH bond generates an isotope effect on geminal CH bonds (Lewis and Schramm, 2003a, b). However, the effect of polarizing the OH bond adjacent to a carbocation has not been reported. The crystal structure of MT-ImmA, a proposed transition state analogue inhibitor, with *S. pneumoniae* MTAN suggests that the side chain of Glu 174 forms a hydrogen bond to the 2'-OH (O—O distance 2.7 Å) and possibly polarizes the bond.[42] The effect of 2'-OH polarization on the KIE was examined by moving a hydroxyl anion toward the 2'-OH from 4.0 Å to 2.4 Å in steps of 0.2 Å. Polarization of the 2'-OH sigma bond causes the 2'-$^3$H IE to increase from 1.10 to 1.18 as the hydroxyl is stepped from 4.0 Å to 2.6 Å (FIG. 10). The 2'-$^3$H IE increases sharply from 1.18 to 1.40 as the Off nucleophile is moved from 2.6 Å to 2.4 Å. The increase in 2'-$^3$H IE with the polarization of 2'-OH expectedly correlates with the increase in C2'-H2' bond length. The observed increase in C2'-H2' bond length and the 2'-$^3$H IE is most likely due to increased hyperconjugation from an enlarged sp-type lone pair at the 2'-oxygen due to polarization of the OH bond. The change in 2'-$^3$H IE due to polarization is mainly in the decreased stretching frequency of C2'-H2' since bending frequencies remain relatively unchanged during the process (data not shown).

Ionization of glucose hydroxyls has been shown to cause significant isotope effects at geminal and adjacent CH centers (Lewis and Schramm, 2003b). It was therefore expected that the ionization of the 2'-OH would cause an isotope effect at 1'-$^3$H and at 3'-$^3$H. The effect on 1'-$^3$H is discussed under the 1'-$^3$H IE section. The calculated 3'-$^3$H IE increases to 1.060 upon ionization of the 2'-hydroxyl. Model calculations with isopropanol predict that the $^3$H isotope effect on vicinal CH bonds is approximately $\frac{1}{3}^{rd}$ of that to the geminal CH bonds (Lewis and Schramm, 2003a), similar to that found here.

Figure 17:
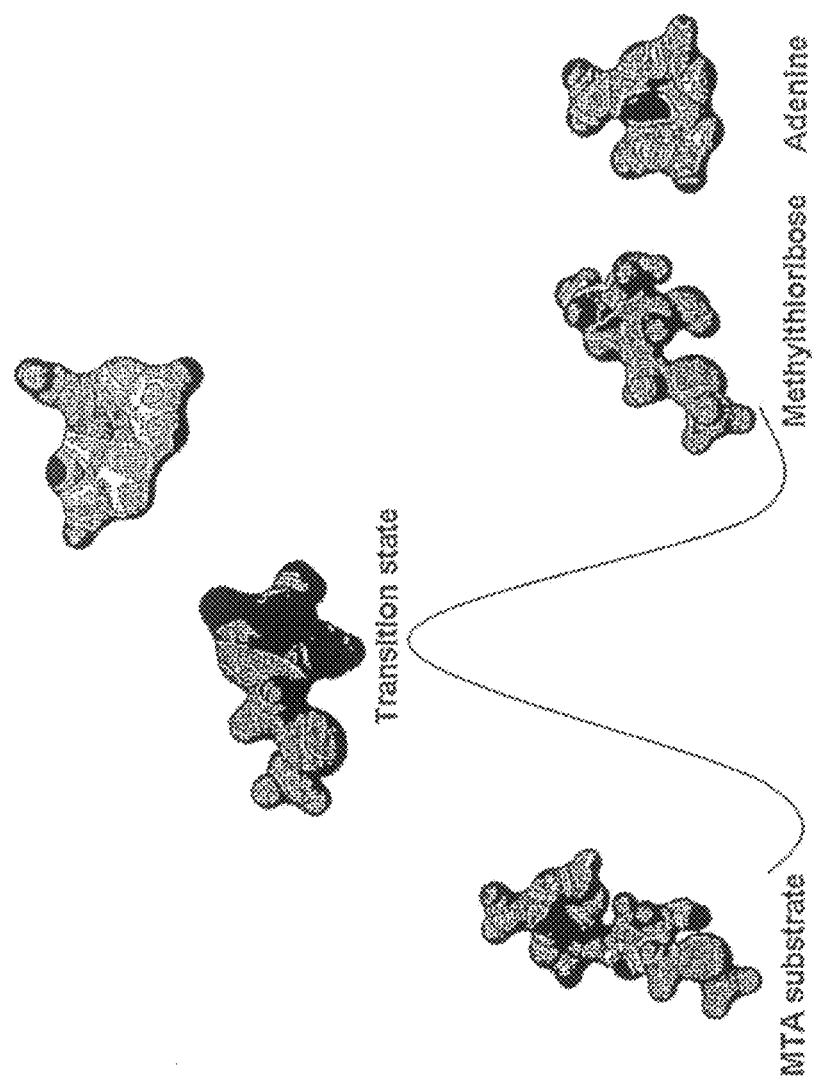
FIG. 17 is a model of a reaction coordinate showing the molecular electrostatic surface potential of 5'-methylthioadenosine (a substrate), the transition state and adenine with 5-methylthioribose (products). MEPs were calculated at HF/STO3G (Gaussian 98/cube) for the geometry optimized at the B3LYP/6-31G(d,p) level of theory and visualized with Molekel 4.0 (34) at a density of 0.008 electron/bohr. The models shown below on the right have same geometry as the MEP surfaces.

Rotation of the H2'-C2'-O—H and H3'-C3'-O—H torsion angles and the 2'-$^3$H IE. Variation of the 2'-$^3$H EIE in the transition state of *S. pneumoniae* MTAN due to rotation of H2'-C2'-O—H torsion angle is shown in FIG. 17. The isotope effects were normalized with respect to the H2'-C2'-O—H torsion angle of 100°. The H1'-C1'-C2'-H2', O4'-C4'-C5'-S and C4'-C5'-S—$C^S$ torsion angles were constrained to restrict the effect to the H2'-C2'-O—H torsion angle. At a H2'-C2'-O—H torsion angle of 70° a maximum isotope effect of 1.145 was observed for 2'-$^3$H. The variation in 2'-$^3$H EIE due to changes in the H2'-C2'-O—H torsion angle arises from the alignment of unhybridized p-type lone pair of the oxygen with the σ* (C2'-H2') antibonding orbital (data not shown).

Figure 18:
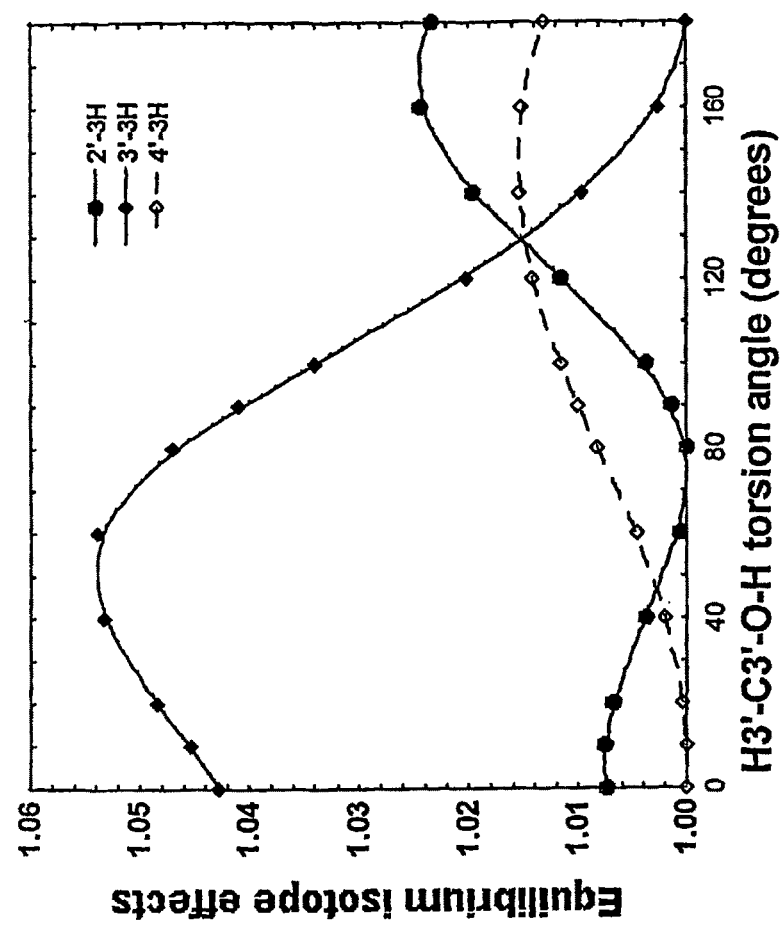
FIG. 18 is a graph of experimental results showing the rotation of the H3'-C3'-O—H torsion angle in the transition state of *S. pneumoniae* MTAN and 2'-$^3$H, 3'-$^3$H and 4'-$^3$H EIEs.

The rotation of the H3'-C3'-O—H torsion angle causes up to a 2% change in 2'-$^3$H IE, with the maximum isotope effect induced at the torsion angle of 160° (FIG. 18). The 2'-$^3$H EIEs are normalized using the 2'-$^3$H EIE calculated at the H3'-C3'-O—H of 80°, 3'-$^3$H EIEs are normalized with respect to 180° and 4'-$^3$H EIEs with respect to 0°. At these torsional angles these isotope effects are lowest. The calculation is performed using the transition state of *S. pneumoniae* MTAN. Following torsional angles were constrained during the calculations;
H 1'-C
O4'-C4'-C5'-S
C4'-C5'-S—$C^S$ Modeling of 1'-$^3$H. The in vacuo models of transition states of enzymatic reactions that proceed via dissociative $S_N1$ transition states predict a larger value of 1'-$^3$H IE than the experimental intrinsic value. For example, *E. coli* MTAN gave a 1'-$^3$H intrinsic KIE of 1.16 compared to the calculated ME of 1.38 (Singh et al., 2005a). Similarly, human and *Plasmodium falciparum* PNPs had intrinsic KIEs of 1.16 and 1.18, whereas as the calculated KIEs predicted a value of ~1.50 (Lewandowicz and Schramm, 2004). The rationale usually invoked to explain these large calculated isotope effects is that the interactions of C1'-H1' with the catalytic site (or solvent) residues at the transition state dampens the out-of-plane bending motions (the major source of 1'-$^3$H KIE), causing the suppression of the 1'-$^3$H KIE. The absence of these effects in the in vacuo calculations gives a large value for the 1'-$^3$H IE. In the following discussion we explore various factors, including the proposed dampening out-of-plane bending motions by van der Waal interactions, that may influence the 1'-$^3$H IE:

a. Effect of the O4'-C1'-N9-C8 torsion angle. MTA has energetically preferred conformations for rotation around the N-glycosidic bond; a possible contribution to the 1'-$^3$H IE. Rotation of O4'-C1'-N9-C8 on 1'-$^3$H IE was studied in MTA using the dihedral angle of 80° as the reference for calculating isotope effects. At an O4'-C1'-N9-C8 dihedral angle of 80° the C1'-H1' bond is the shortest and the 1'-$^3$H IE effects for all the other angles are normal with respect to the 80° torsion angle (FIG. 12). At the O4'-C1'-N9-C8 torsion angle of 180°, adenine is syn to 5'-methylthioribose and at 0° it is in the anti conformation. Adenine prefers anticlinical and antiperiplanar conformations between 130°-180° as well syn-conformations between 30° and 60°, but the barrier for rotation around O4"-C1'-N9-C8 torsional angle is not large (~0.7 kcals/mol). The 1'-$^3$H IE increases with the change in dihedral angle on either side of 80° and is largest (1.084) at 180°/anti conformation. The syn/0° conformation for adenine also gave a large normal isotope effect of 1.07. Thus, orientation of adenine, when immobilized by the enzyme, could change the calculated 1'-$^3$H IE by as much as 1.08.

b. Effect of changing the dielectric constant. The dielectric constant (∈) experienced by reactant is significantly different when bound to enzyme relative to solvent. Proteins in solution can have localized microenvironments of high ∈, including the active sites of enzymes which are expected to have many polar groups (Dwyer et al., 2000). A range of dielectric constants from 4.9 to 78.8 was explored as a possible source of isotope effects. Changing the dielectric field has no influence on the 1'-$^3$H isotope effect (Table 8). Isotope effects at all positions remain relatively unchanged as the ∈ is increased. Secondary isotope effects are vibrational effects and are sensitive to distribution of electron density and behavior of electron density under external field depends on the geometrical structure of the molecule. The structure of the transition state remains relatively unchanged upon increasing the ∈.

TABLE 8

Effect of Virtual Solvent on Isotope effects

| Dielectric constant | Equilibrium Isotope effects (EIEs) | | | | |
|---|---|---|---|---|---|
| | 1'-$^3$H | 1'-$^{14}$C | 2'-$^3$H | 4'-$^3$H | 5'-$^{14}$C |
| 4.90 | 1.415 | 1.003 | 1.122 | 0.984 | 1.006 |
| 10.36 | 1.415 | 1.003 | 1.124 | 0.984 | 1.006 |
| 20.70 | 1.416 | 1.003 | 1.125 | 0.984 | 1.006 |
| 32.63 | 1.416 | 1.003 | 1.126 | 0.984 | 1.006 |
| 38.20 | 1.416 | 1.003 | 1.126 | 0.984 | 1.006 |
| 46.70 | 1.416 | 1.003 | 1.125 | 0.983 | 1.006 |
| 78.70 | 1.416 | 1.003 | 1.126 | 0.984 | 1.006 |

The isotope effects were calculated with respect to MTA in water (∈=78.8).

c. van der Waal Interactions. The active sites of enzymes are proposed to be more constrained at the transition state than in the ground state. Thus, van der Waal clashes of C1'-H1' with residues in the active site might dampen the out-of-plane bending motion of C1'-H1' bond and reduce 1'-$^3$H ME. This proposal was evaluated using a minimal model of the *S. pneumoniae* MTAN transition state and a hydrogen molecule. The effect on 1'-$^3$H IE was studied by impinging a hydrogen molecule on C1'-H1' by bringing it (axially along the horizontal axis) from a distance of 3.0 Å to 1.2 Å. The 1'-$^3$H IE increased as the hydrogen approaches close to the van der Waal radii of H1' (FIG. 13A). The 1'-$^3$H IE increased from 1.48 to 1.70 as the H1'-H$^{hydrogen}$ distance was reduced from 1.8 Å to 1.2 Å (van der Waal radius of the hydrogen atom is 1.2 Å). The bond length of C1'-H1' also increased progressively with the reduction in H1'-H$^{hydrogen}$ distance and has the same general shape as the 1'-$^3$H IE. The incoming hydrogen molecule induces a dipole in H1' and the resulting induced dipole-dipole interaction weakened the C1'-H1' bond, reduced stretching force constants and increased the 1'-$^3$H IEs. This minimal model demonstrates that horizontal approach of a molecule to the van der Waal radii of H1' would increase the 1'-$^3$H IE. Similar results were obtained using oxygen or formaldehyde instead of hydrogen (FIG. 19). Therefore, van der Waal interactions with the transition state are unlikely to decrease the 1'-$^3$H IE by dampening the out-of-plane bending motion of C1'-H1'.

e. Varied H1'-C1'-C2'-H2' and H2'-C2'-O—H torsion angles polarization of the 2'-OH and 1'-$^3$H isotope effect. Rotation of the H1'-C1'-C2'-H2' and H2'-C2'-O—H torsion angles have a significant effect on the α-secondary 1'-$^3$H IE. Orientation of the H1'-C1'-C2'-H2' torsion angle can contribute a maximum of 1.05 to the 1'-$^3$H IE (FIG. 13B, C), whereas the H2'-C2'-O—H torsion angle can contribute a maximum of 1.04. The 1'-$^3$H IEs of 1.04 and 1.03 were observed for H2'-C2'-O—H torsion angle of 180° and 0°, respectively.

Polarization of the 2'-hydroxyl also influences the 1'-$^3$H IE. A maximum change of 1.028 was observed for complete ionization of 2'-hydroxyl (FIG. 13D).

Protonation of adenine nitrogens and $^{15}$N EIEs. *S. pneumoniae* MTAN has a fully-dissociated transition state. Dissociation of the N-glycosidic bond in MTA causes increased electron density in adenine, increasing the p$K_a$ of adenine nitrogens. In most purine N-ribosyl transferases, protonation of the purine at N7 is proposed as a part of the transition state structure. Here $^{15}$N EIEs are explored for monoprotonated adenine at N1, N3, N7 or N9 and for the unprotonated adenine relative to unprotonated MTA (Table 9). Monoprotonation at N1 gives an inverse $^{15}$N1 IE of 0.987 and the isotope effects for $^{15}$N3 and $^{15}$N7 were close to unity but an IE of 1.028 at $^{15}$N9. The large normal isotope effect at N9 occurs because dissociation of the C1'-N9 bond causes increased vibrational freedom at N9. Protonation at N3 also gave IEs of unity for $^{15}$N3, $^{15}$N7 and $^1$N1, but a large normal isotope effect of 1.028 for $^{15}$N9, similar to N1 protonation. A small decrease in the $^{15}$N9 IE, from 1.028 to 1.025, was observed with N7 protonation. Protonation of N9 results in substantial decrease in the $^{15}$N9 isotope effect; from 1.028 to 1.010. The decrease is due to partial compensation of the lost C1' N9 mode with the H—N9 mode. Significant changes in $^{15}$N IEs were also observed for unprotonated adenine. Conversion of MTA to anionic adenine gave $^{15}$N1 and $^{15}$N7 IE of 1.010 and 1.018, respectively whereas the isotope effect for $^{15}$N9 increased to 1.036, close to the theoretical maximum of 1.040 for $^{15}$N. The large $^{15}$N9 IE is due to the increased vibrational freedom following dissociation of N-glycosidic bond and due to the absence of compensatory increase in bond order in the absence of conjugated ring system. Disruption of conjugation in unprotonated adenine causes decrease in vibrational modes due to decrease in bond order to N9. Total bond length to N9 (C4-N9 and C8-N9) increased from 2.688 Å in protonated adenine to 2.714 Å in unprotonated adenine. Small normal $^{15}$N1 and $^{15}$N7 IEs were also observed in unprotonated adenine.

TABLE 9

Effect of Adenine protonation on N1, N3, N7, N9 KIEs.

| Site of Protonation on Adenine | Calculated Kinetic Isotope Effects | | | |
|---|---|---|---|---|
| | N1 | N3 | N7 | N9 |
| N1 | 0.987 | 0.999 | 1.003 | 1.028 |
| N3 | 0.999 | 0.999 | 1.003 | 1.028 |
| N7 | 0.998 | 0.999 | 1.002 | 1.025 |
| N9 | 1.000 | 1.000 | 1.000 | 1.010 |
| Unprotonated | 1.010 | 1.002 | 1.018 | 1.035 |

The isotope effects are calculated with respect to MTA. The table reports the $^{15}$N isotope effects at four adenine nitrogens due to protonation of N1, N3, N7 or N9 and also for unprotonated adenine.

Polarization of the 3'-hydroxyl and the 4'-$^3$H EIE. Crystal structures of *E. coli* and *S. pneumoniae* MTAN with MT-ImmA, a transition state analogue inhibitor of MTAN, indicate that the 3'-hydroxyl of MT-ImmA is strongly hydrogen bonded to Glu174; suggesting partial or full polarization of the 3'-OH at the transition state. Polarization of the 2'-OH causes significant changes in the properties of the neighboring C2'-H2', C1'-H1', and C3'-H3' bonds. However the effect on the C4'-H4' bond is minimal. Polarization of the 3"-OH is expected to influence the 4'-$^3$H and 2'-$^3$H IEs. A hydroxyl anion was used to polarize the 3'-OH bond in the transition state of *S. pneumoniae* MTAN (FIG. 14). The 4'-$^3$H IE increased steadily from 0.94 to 1.016 as the hydroxyl nucleophile is stepped from 4.0 Å to 2.4 Å. Unlike the 2'-hydroxyl polarization, no sudden increase in isotope effect was observed between 2.5 Å and 2.4 Å (FIG. 14). Complete ionization of the 3'-OH gives a maximum isotope effect of 1.015 for 4'-$^3$H, an increase from 0.935 to 1.015. Although the 4'-$^3$H IE increased steadily, no increase in hyperconjugation between the lone pairs of O3 and the σ* (C4'-H4') antibonding orbital was observed, suggesting an indirect mechanism of electron transfer. The change in 4'-$^3$H IE correlates strongly with the increase in negative charge on ring oxygen (O4') (FIG. 14). Ionization of 3'-hydroxyl results in delocalization of electrons that are shared unequally by more electronegative or electron deficient atoms in the ribose ring. Unequal charge sharing due to ionization of a hydroxyl has been observed in glucose (Lewis and Schramm, 2003b). These inductive electronic effects can result in increased hyperconjugation to the adjacent σ* (C4'-H4') antibonding orbital, causing the 4'-$^3$H IE and the 2'-$^3$H IE to increase. The size of these remote IEs, calculated in vacuo, will be influenced by the nature of the contacts at the catalytic site. However they provide a useful indication of the origins of the intrinsic IEs.

Effect of the C4'-C5'-S—C$^{Me}$ torsion angle rotation on [Me-$^3$H$_3$] KIEs. The 5'-methylthio group of MTA is free to rotate about the C5'-S bond, altering the C4"-C5"-S—C$^{Me}$ torsional angle. This torsion angle is fixed near −82.7° and −87.7°, respectively in the active sites of *S. pneumoniae* (Singh et al., 2006) and *E. coli* MTAN (Dwyer et al., 2000) with MT-ImmA. Freezing of this torsion angle upon binding to enzyme could give the 1.055 isotope effect observed from the methyl hydrogens. Rotation of the C4"-C5"-S—C$^{Me}$ torsional angle was explored as a possible source of the isotope effect (FIG. 15).

Figure 20:
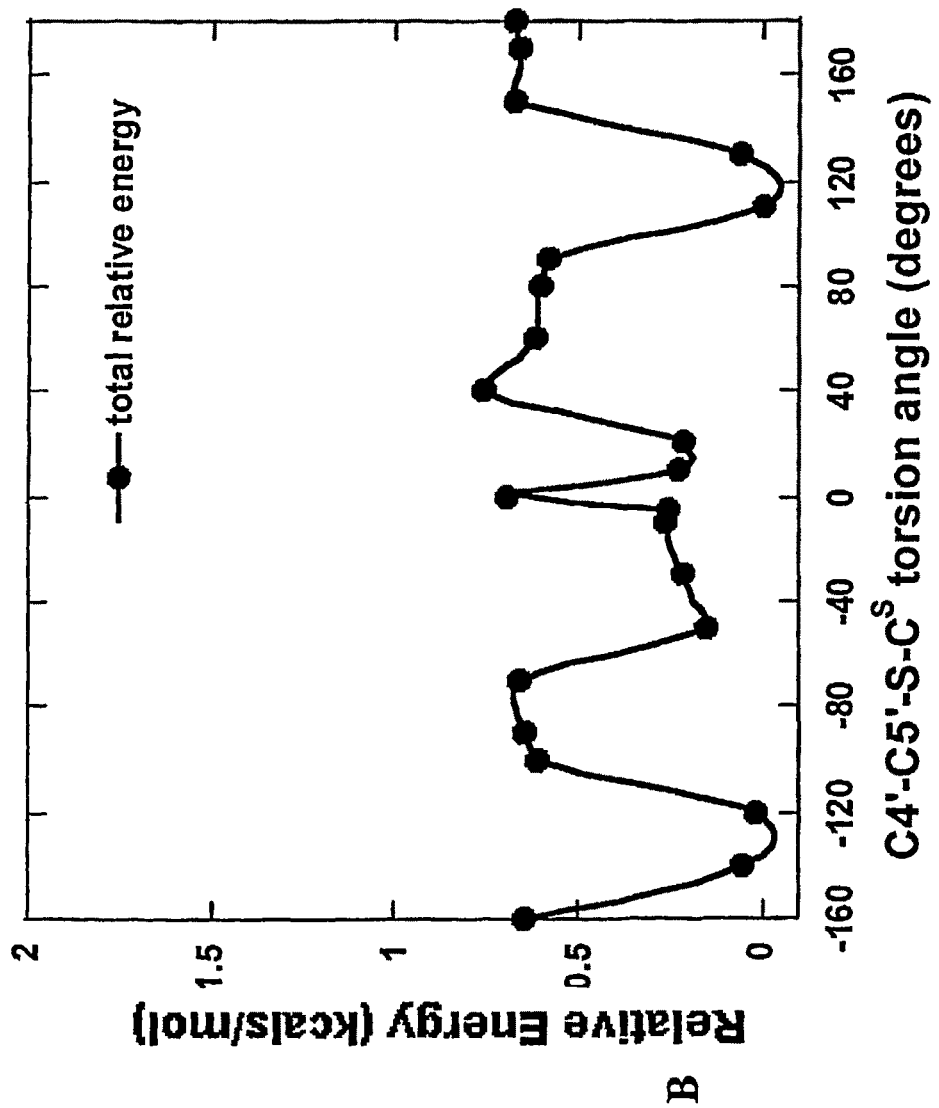
FIG. 20 is a graph of experimental results showing the change in total relative energy of tetrahydro-2-((methylthio)methyl)furan due to the rotation of C4'-C5'-S—$C^S$ torsion angle.
Figure 22:
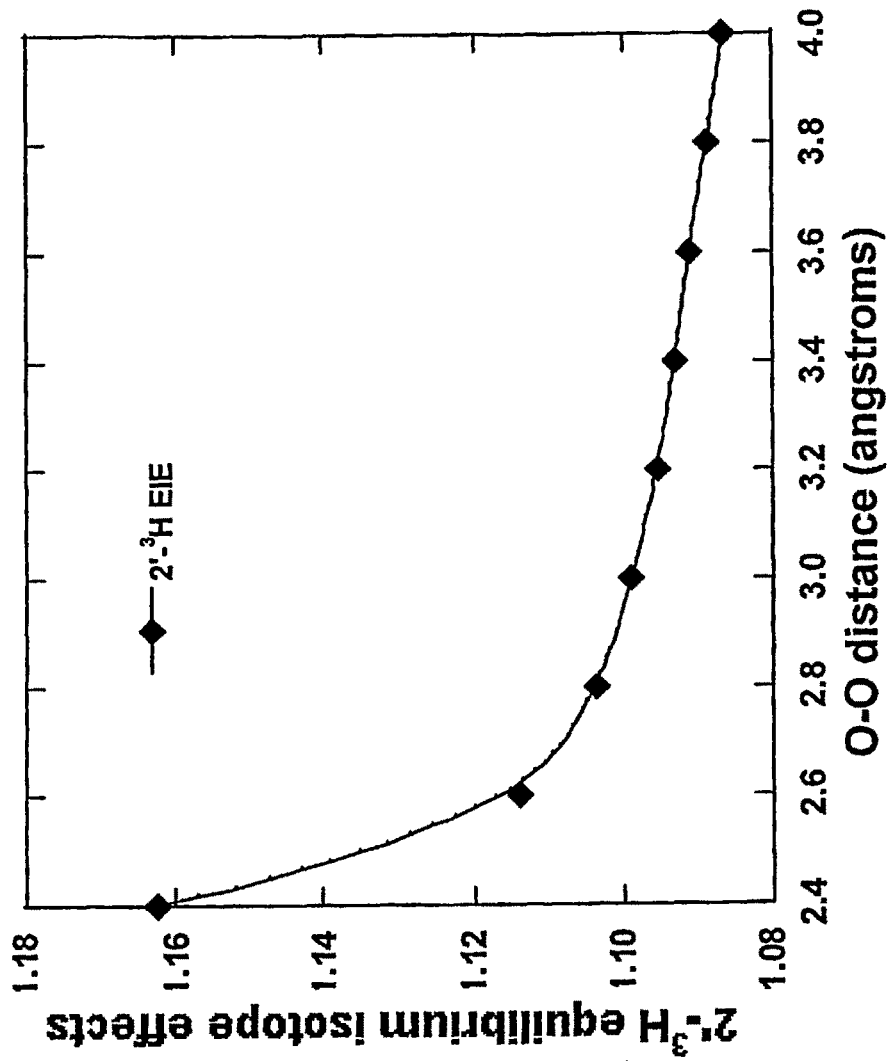
FIG. 22 is a graph of experimental results showing the polarization of 3'-OH and 2'-$^3$H Isotope effects (KIEs).

Tetrahydro-2-((methylthio)methyl)furan provided a minimal model for rotation of the C4'-C5'-S—C$^{Me}$ bond. The C—H bonds of the methyl group were not constrained during the calculation. Puckering of the furan ring was fixed during the calculation by constraining the O4'-C1'-C2'-C3' torsion angle to 27°, while the C4'-C5"-S—C$^{Me}$ torsional angle was stepped through 360° in 20° increments (FIG. 15). A C4'-C5'-S—C$^{Me}$ torsional angle of 0° gave the shortest overall average bond length and was used as the reference state. The methyl hydrogens show distinct angular variation of their isotope effects. Angular variation of the isotope effects is due to variation of negative hyperconjugation (n$_p$(S) to σ*(CH) antibonding orbital) upon rotation of the C4"-C5"-S—C$^{Me}$ bond. Three energetic minima are found at −120°, between −40° to +20° and at +120°, although the barrier for rotation is relatively small at 0.76 kcal/mol (FIG. 20).

Variation of isotope effects at methyl hydrogens in the cationic transition state was investigated by repeating the calculation with deprotonated tetrahydro-2-((methylthio)methyl)furan at C4, the atom corresponding to C1' in MTA.

Deprotonation at C4 reduced the maximum isotope effect from 1.13 to 1.044 (FIG. 21). The observed decrease is mainly due to reduction in the negative hyperconjugation of the lone pair of sulphur. Following torsion angles were kept frozen during the calculation:

O4'-C4'-C5'-S
H1'-C1'-C2"-H2'(pro)

Deprotonation at C1' decreases the maximum [Me-$^3H_3$] isotope effect from 1.13 to 1.044. It is not clear how the effect is propagated across six bonds. However, it seems that deprotonation at C1' reduces the ability of sulphur to hyperconjugate, away from cationic center, with σ* ($C^{Me}H$) antibonding orbitals.

Discussion

Transition state of S. pneumoniae MTAN and 1'-$^{14}$C isotope effect. The α-primary 1'-$^{14}$C KIE is the most diagnostic isotope effect for nucleophilic substitution reactions (Berti and Tanaka, 2002). It is sensitive to the bond orders of leaving group and the attacking nucleophile at the transition state. Associative $S_N2$ transition states have an α-primary 1'-$^{14}$C KIE of 1.080 to 1.13, whereas isotope effects of 1.03 to 1.08 correspond to small residual bond orders in $S_N1$ transition states and fully dissociative $S_N1$ transition states are characterized by 1'-$^{14}$C KIEs close to unity. Most N-ribosyltransferases have 1'-$^{14}$C KIE between 1.00 and 1.03 (Singh et al., 2005a; Lewandowicz and Schramm, 2004), and have dissociative $S_N1$ mechanisms with significant ribooxacarbenium character. The primary 1'-$^{14}$C IE of unity for S. pneumoniae MTAN indicates a dissociative $D_N*A_N$ mechanism. Loss of bond order to the leaving group is compensated by increased bond order to O4', H1' and C2', since all 3N-6 vibrational modes in the reactant and oxacarbenium ion contribute the isotope effects. Thus, the loss of C1-N9 bond at the transition state is compensated by the increase in bond order to the neighboring atoms. Bond order is inversely related to bond length and it is observed that in the transition state relative to substrate the bond length of anomeric carbon to H1' decreased to 1.0905 Å from 1.0936 Å, to C2' the bond length decreased from 1.0537 Å to 1.0505 Å and to the ring oxygen (O4') it decreased from 1.412 Å to 1.249 Å from, indicating significant increase in bonding to these atoms at the transition state of S. pneumoniae MTAN, compensating the loss of bond order to adenine. Due to this compensation the decrease or loss of the C1' N9 vibrational mode does not cause isotope effect at the anomeric carbon in dissociative $S_N1$ transition states, because all 3N-6 normal modes contribute calculate isotope effects.

Natural bond orbital analysis of the transition state and MTA indicates that the anomeric carbon is $sp^{1.84}$ hybridized at the transition state relative to $sp^{2.82}$ in the substrate (Table 6). These changes increase the cationic character at the transition state (positive charge on O4' and C1' increases by +0.14 and +0.34 respectively) relative to MTA. This sharing of charge is characteristic of ribooxacarbenium ions (Berti and Tanaka, 2002). The transition state is also characterized by a partially empty p-orbital on the anomeric carbon that causes isotope effects at α-, β- and δ-positions.

Protonation of N7 and primary [9-$^{15}$N] Isotope Effect (IE). The maximum 9-$^{15}$N theoretical KIE value predicted for loss of the C1'-N9 bond is 1.04. In MTA, loss of the N-glycosidic bond predicts a 9-$^{15}$N IE of 1.036 (Table 9) and partial restoration of conjugation in the adenine ring system through protonation of N7 decreases the 9-$^{15}$N IE from 1.036 to 1.025. The 9-$^{15}$N intrinsic KIE of 1.036 measured for S. pneumoniae MTAN indicates a complete loss of the C1'-N9 bond at the transition state, a conclusion also supported by the 1'-$^{14}$C KIE. Complete loss of the C1'-N9 bond causes significant re-hybridization of N9 and natural bond orbital analysis predicts N9 to be $sp^{1.89}$ hybridized at the transition state compared to se in MTA. The 9-$^{15}$N intrinsic KIE of 1.036 indicates adenine is not protonated and therefore is anionic at the transition state. Protonation of adenine in S. pneumoniae MTAN occurs after the substrate has passed the transition state and breaking the N-glycosidic bond precedes adenine protonation. The transition state of S. pneumoniae MTAN differs from the transition state of MTAN from E. coli (Singh et al., 2005a), which involves activation of the leaving group in the form of N7 protonation. Breaking the N-ribosidic without leaving group activation suggests that a major force in achieving the transition state is conversion of the ribosyl group to the ribooxacarbenium ion (discussed further with 4'-$^3$H KIE).

Sugar puckering and the 2'-$^3$H KIE. The O-secondary 2'-$^3$H ME is influenced by hyperconjugation of the σ (C2'-H2') electrons to the partially empty $2p_z$ orbital of C1', polarization of the 2'-OH and orientation of the H2'-C2'-O—H torsion angle. The extent of hyperconjugation depends on overlap between the C2'-H2' sigma bond and the electron-deficient p-orbital on the anomeric carbon. The KIE is greatest when the C2'-H2' bond is parallel to the carbenium ion p-orbital and reaches a minimum when the C—H bond is perpendicular to the orbital. The isotope effect varies as a $\cos^2\theta$ function of this overlap. The extent of hyperconjugation is also affected by the amount of positive charge or the emptiness of the p-orbital on the anomeric carbon. For a fully-dissociated $S_N1$ transition state a 2'-$^3$H KIE of 1.12 was calculated for a $2p_z$-C1'-C2'-H2' dihedral angle of 0° (FIG. 9). The intrinsic KIE of 1.092 measured for S. pneumoniae MTAN corresponds to a H1'-C1'-C2'-H2' torsion angle of 70° (or p-orbital-C1'-C2'412' of 20°) indicating substantial overlap with the partially empty $2p_z$ orbital at C1'. A H1'-C1'-C2'-H2' torsion angle of 70° indicates 3-exo puckering for the ribosyl group and a O4'-C1'-C2'-C3' dihedral angle of 13°. The magnitude of the 2'-$^3$H KIE is also sensitive to polarization of the 2'-hydroxyl and orientation of the H2'-C2'-O—H torsion angle. Glu174 is within hydrogen bonding distance from the 2'-hydroxyl in S. pneumoniae and is conserved in MTANs, suggesting polarization of the 2'-OH may contribute to the 2'-$^3$H KIE (Singh et al., 2005a; 2006). With the sugar pucker of the transition state fixed to that of MT-ImmA bound to MTAN (Singh et al., 2006), a H1'-C1'-C2'-H2' torsion angle of 65° was obtained and corresponds to an isotope effect of 1.064 (FIG. 9). Of the total 2'-$^3$H KIE of 1.092, 1.064 comes from hyperconjugation and 1.028 is from polarization of 2'-hydroxyl or 3'-hydroxyl and/or orientation of the H2'-C2'-O—H torsion angle.

1'-$^3$H KIE. The intrinsic 1'-$^3$H KIE of 1.23 contains contributions from the out-of-plane bending modes of C1'-H1' to give a normal KIE as well as altered C1'-H1' stretching modes which contribute inversely to the KIE (inverse effects).

The nature of α-secondary tritium isotope effect in dissociative $S_N1$ transition states was studied using Methylchloride ($CH_3Cl$). Dissociation of $CH_3Cl$ to methyl cation and chloride anion represents a minimal model to study α-secondary $^3$H 16 in dissociative $S_N1$ transition states. The isotope effects of three methyl hydrogens increase steadily with the increase in C—Cl bond distance. They increase linearly up to 3.2 Å and then plateaus, suggesting complete formation of methyl cation at this distance (FIG. 6). The change in $^3$H isotope effects if identical for three methyl CHs bonds.

Isotope effects are predominantly vibrational effects and contain contribution from stretching as well as bending modes. Both magnitude of stretching as well as bending modes contribute too the isotope effects. Decrease in frequency of stretching and bending modes is associated with increased isotope effect. The dissociation of MeCl increases the magnitude of stretching modes due to increased bond order and contribute negatively to the isotope effects. Stretching modes of three CHs increase from 3108 cm$^{-1}$, 3208 cm$^{-1}$ and 3208 cm$^{-1}$ in MeCl (C—Cl distance of 1.0803 Å) to 3164 cm$^{-1}$, 3357 cm$^{-1}$ and 3357 cm$^{-1}$, respectively in methyl cation (C–Cl distance of 5.0 Å). The increase in isotope effect of methyl hydrogens due to dissociation of MeCl comes entirely from the reduction in bending modes following dissociation of C—Cl bond (supplementary material). Three CHs of methyl group have five bending modes, their magnitude decrease from 1519 cm$^{-1}$, 1519 cm$^1$, 1422 cm$^{-1}$, 1051 cm$^{-1}$, and 1051 cm$^{-1}$ in MeCl (C—Cl distance of 1.0803 Å) to 1449 cm$^{-1}$, 1449 cm-1, 979 cm$^{-1}$, 107 cm$^{-1}$, 107 cm$^{-1}$ in methyl cation (C—Cl distance of 5.0 Å), respectively. Last two of five bending modes contribute maximally to the observed increase in α-secondary tritium isotope effect.

Figure 23:
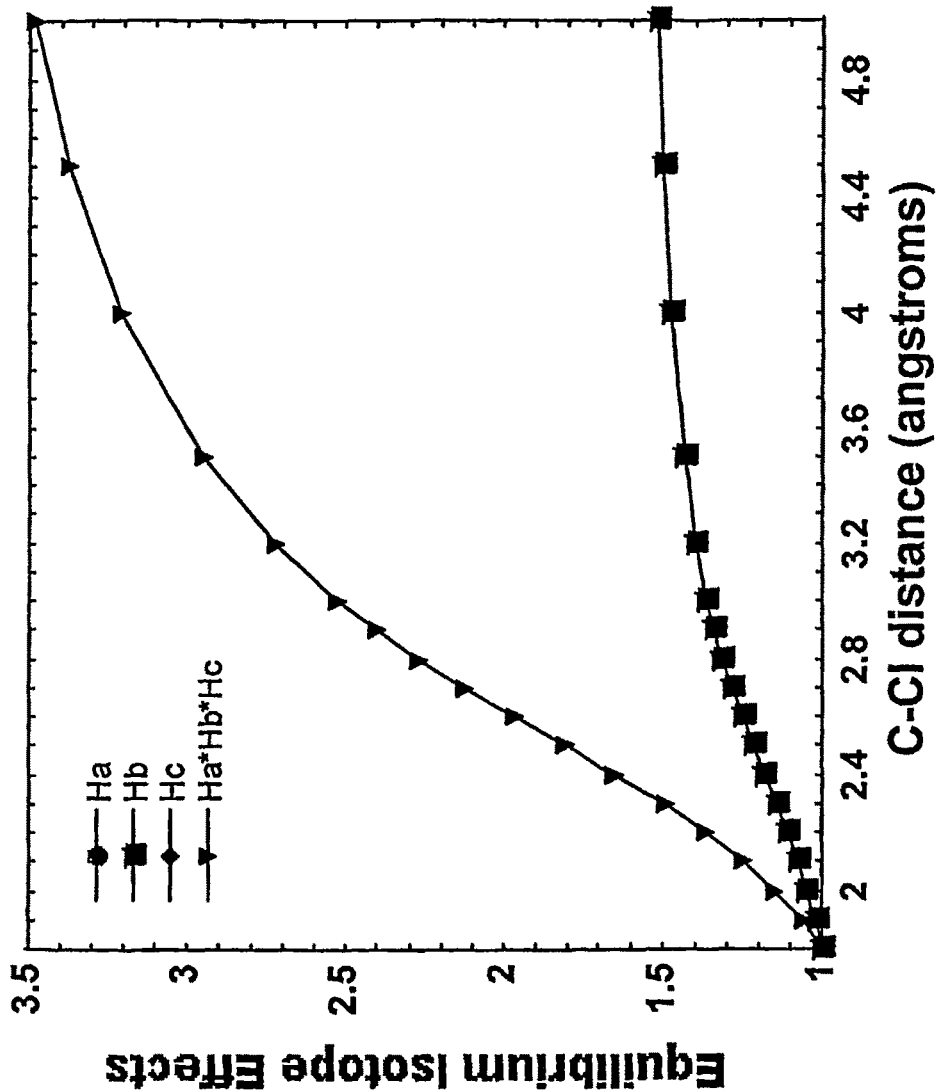
FIG. 23 is a graph of experimental results showing the increase in C—Cl bond distance in methylchloride and α-secondary $^3$H IE.
Figure 24:
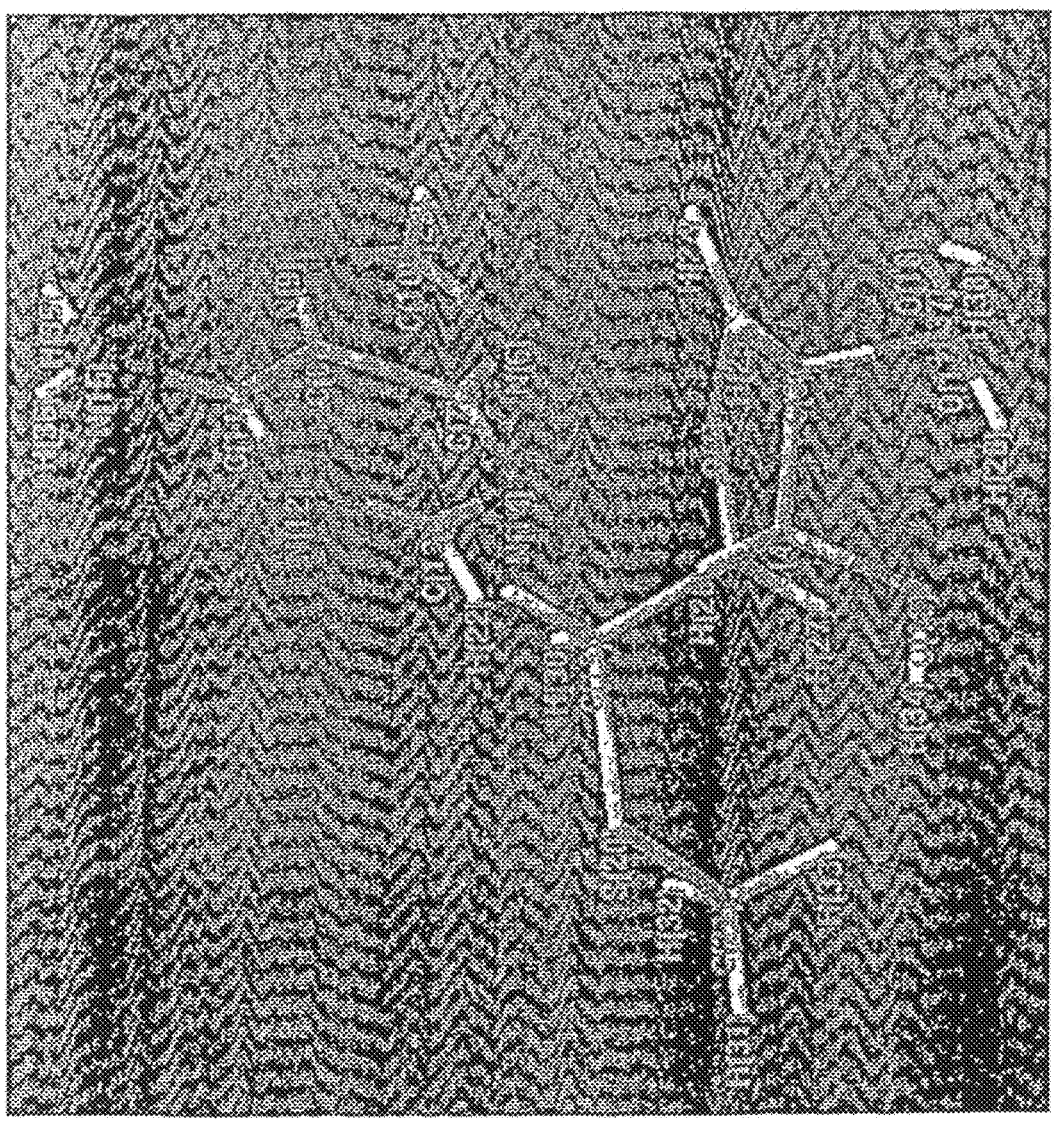
FIG. 24 is a model showing the structure of the transition state determined at B1LYP/6-31G* without any constraints, by including both the leaving group and the water nucleophile.
Figure 25:
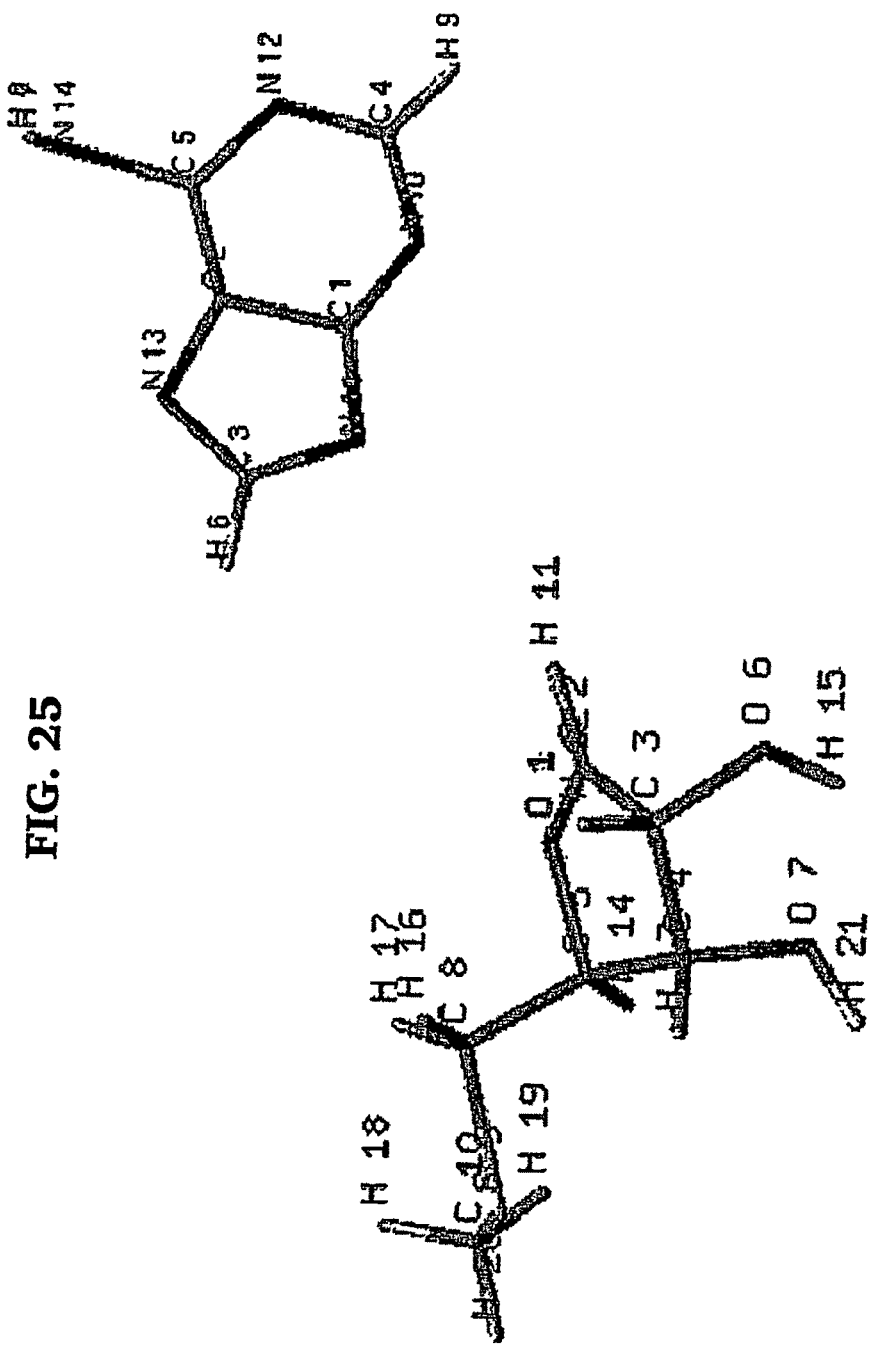
FIG. 25 is a model showing the transition state intermediate of *S. pneumoniae* MTAN determined at B1LYP/6-31G* using constraints as described in Example 2. The ribosyloxacarbenium ion intermediate and the unprotonated adenine at the transition state were modeled separately.

Model calculation on methyl chloride predict that the 1'-$^3$H KIE for $S_N1$ transition states comes primarily from the decrease in bending modes of cationic methyl CHs (Table 10, FIG. 23). The normal isotope effect caused by increased out-of-plane bending motion is always opposed by increased stretching mode force constants (Pham et al., 1997). Although both factors contribute to the magnitude of this KIE, the relative variation in the observed 1'-$^3$H KIE for different enzymes is dominated by decreased force constants for bending modes at the transition state.

contribute about 1.14 to the calculated 1'-$^3$H IE, but still do not account for the large discrepancy in the calculated 1'-$^3$H IE. Dampening of bending modes due to van der Waal interactions is also unlikely as these interactions increase the calculated isotope effect further due to a decrease in stretching modes. Crystal structures of MTANs from *S. pneumoniae* and *E. coli* show the region surrounding C1'-H1' with no residue in van der Waal contact, although dynamic excursions involved in the transition state formation cannot be ruled out. It is also possible that the discrepancy between intrinsic and calculated 1'-$^3$H isotope effects is due to the inaccuracy of density function theory (DFT) and Hartree-Fock (HF) methods in predicting the bending modes. For example, the semiempirical PM3 method predicts a value of 1.17 close to the intrinsic 1'-$^3$H KIE of 1.23. The geometry of the transition state does not depend on matching the 1'-$^3$H KIE and the value is consistent with KIEs measured for other ribooxacarbenium ion transition states.

The [4'-$^3$H] KIE and transition state structure. The C4'-H4' bond is three bonds from the reaction center but is alpha to the C4'-C4' bond. In MTA the lone pair ($n_p$) of O4' hyperconjugates with the σ* (C4'-H4') antibonding orbital and decreases its bond order. The cationic transition state causes diversion of $n_p$ of O4' towards the cationic anomeric carbon (C1'). Hyperconjugation towards the C1' at the transition state is compensated by decreased hyperconjugation of $n_p$ of O4' into the σ* (C4'-H4') antibonding orbital, causing shortening of

TABLE 10

Change in normal modes of methylchloride with the increase in C—Cl bond distance.

| | MeCl (1.803 Å) | 1.9 Å | 2.0 Å | 2.1 Å | 2.2 Å | 2.3 Å | 2.4 Å | 2.5 Å |
|---|---|---|---|---|---|---|---|---|
| 1 | 723.6755 | 559.5371 | 415.0956 | 289.6813 | 176.3741 | 25.296 | −134.311 | −167.903 |
| 2 | 1051.497 | 1002.446 | 949.8306 | 895.1005 | 838.7071 | 781.4466 | 728.9777 | 674.7765 |
| 3 | 1051.497 | 1002.447 | 949.8314 | 895.1013 | 838.708 | 781.4477 | 728.9791 | 674.7781 |
| 4 | 1422.927 | 1365.748 | 1309.539 | 1256.389 | 1207.289 | 1163.281 | 1128.293 | 1097.454 |
| 5 | 1519.454 | 1506.483 | 1494.619 | 1484.45 | 1476.051 | 1469.309 | 1465.372 | 1461.7 |
| 6 | 1519.454 | 1506.484 | 1494.619 | 1484.45 | 1476.051 | 1469.309 | 1465.372 | 1461.701 |
| 7 | 3108.747 | 3130.067 | 3146.372 | 3159.372 | 3169.885 | 3178.453 | 3177.642 | 3180.235 |
| 8 | 3208.122 | 3248.73 | 3281.726 | 3308.56 | 3330.296 | 3347.754 | 3353.289 | 3361.012 |
| 9 | 3208.122 | 3248.731 | 3281.727 | 3308.56 | 3330.296 | 3347.754 | 3353.29 | 3361.012 |

| | 2.6 Å | 2.8 Å | 2.9 Å | 3.0 Å | 3.2 Å | 3.5 Å | 4.0 Å | 4.5 Å | 5.0 Å |
|---|---|---|---|---|---|---|---|---|---|
| 1 | −190.759 | −209.879 | −209.075 | −206.46 | −198.561 | −178.867 | −146.16 | −116.028 | −89.3237 |
| 2 | 622.265 | 527.0553 | 485.9228 | 448.4001 | 385.7862 | 314.8306 | 227.3623 | 161.8587 | 107.1458 |
| 3 | 622.2665 | 527.056 | 485.9234 | 448.4008 | 385.7871 | 314.8313 | 227.3623 | 161.8589 | 107.1459 |
| 4 | 1072.699 | 1041.647 | 1033.588 | 1028.3 | 1022.806 | 1018.578 | 1007.478 | 993.2815 | 979.2785 |
| 5 | 1458.952 | 1455.405 | 1454.304 | 1453.479 | 1452.367 | 1451.45 | 1450.573 | 1450.074 | 1449.801 |
| 6 | 1458.953 | 1455.406 | 1454.304 | 1453.48 | 1452.368 | 1451.45 | 1450.574 | 1450.075 | 1449.802 |
| 7 | 3181.335 | 3180.722 | 3179.621 | 3178.22 | 3175.165 | 3171.522 | 3167.711 | 3165.708 | 3164.867 |
| 8 | 3365.929 | 3370.076 | 3370.364 | 3369.939 | 3368.037 | 3364.98 | 3361.099 | 3358.568 | 3357.174 |
| 9 | 3365.929 | 3370.077 | 3370.365 | 3369.939 | 3368.038 | 3364.98 | 3361.1 | 3358.568 | 3357.175 |

The table shows the change in normal modes of methylchloride as the C—Cl bond distance is increased from 1.803 Å to 5.0 Å.
1 Normal mode corresponding to the reaction coordinate (C—Cl)
2-6 Bending modes of methyl CH bonds.
7-9 Stretching modes of methyl CH bonds.

Computational modeling of the 1'-$^3$H KIE to match experimental values is difficult and has been discussed (Berti and Tanaka, 2002). The computed isotope effect for 1'-$^3$H MTA for the *S. pneumoniae* MTAN transition state at 298K in vacuum using the B1LYP/6-31G(d) level of theory is 1.47, almost double the intrinsic 1'-$^3$H KIE of 1.23. Although van der Waal interactions have been implicated, these interactions have an opposite effect in the calculated 1'-$^3$H IE (see above). Ground state effects including the O4'-C1'-N9-C8 torsion angle, polarization of the 2% OH and rotation of the H2'-C2'-O—H bond can also influence the 1'-$^3$H IE. Together they can C4'-H4' sigma bond (FIG. 14). Natural bond orbital analysis predicted a large electron delocalization energy (6.59 kcal/mol) for the $n_p$ (O4') to σ* (C4'-H4') hyperconjugation in MTA but less than <0.5 kcal/mol in the transition state. This change predicts a stiffer C4'-H4' bond at the transition state to give an inverse 4'-$^3$H KIE. An inverse 4'-$^3$H IE of 0.94 was calculated for the transition state, in contrast to the experimental intrinsic KM of 1.015. The 4'-$^3$H KIE measured for *S. pneumoniae* MTAN is similar to that of 1.010 measured for *E. coli* MTAN. Based on calculations with on 2-propanol, it was argued that 3'-hydroxyl polarization would increase hyperconjugation between lone pairs of the 3'-hydroxyloxygen and the σ*(C4'-H4') antibonding orbital (Singh et al., 2005). The crystal structure of *E. coli* MTAN with MT-ImmA shows the Glu174 carboxylate 2.7 Å from the 3'-hydroxyl (Shi et al., 2001b). *S. pneumoniae* MTAN also has Glu174 interacting with the 3'-hydroxyl, therefore a similar mechanism of 3'-hydroxyl deprotonation at the transition state would explain the KIE. Using a hydroxyl anion to polarize the 3'-hydroxyl of the *S. pneumoniae* MTAN transition state gave an isotope effect of 1.015 for 4'-$^3$H for complete ionization of the 3'-hydroxyl, due to increased $n_p$(O4') to σ* (C4'-H4') hyperconjugation and greater charge accumulation on O4'. The increased charge on O4' also stabilizes the transition state by electron sharing with the cationic C1'.

Remote Me-$^3$H and 5'-$^3$H KIEs. An intrinsic isotope effect of 1.055 was measured for methyl-$^3$H$_3$ MTA for *S. pneumoniae* MTAN. The methylthio group of 5'-methylthioadenosine is fixed in the active site of *S. pneumoniae* MTAN by hydrophobic interaction with non-polar residues including Met9, Ile50, Val102, Phe105 and Phe207 (Singh et al., 2006). Freezing the C4'-C5'-S—C$^{Me}$ torsion angle subsequent to MTA binding gives rise to the observed isotope effect (FIG. 15).

An intrinsic KIE of 1.019 for 5'-$^3$H$_2$ MTA in *S. pneumoniae* MTAN is small compared to other N-ribosyl transferases such as purine nucleoside phosphorylase and thymidine phosphorylase. The 5'-methylthio group of MTA differs from the hydroxymethyl of inosine in its lack of hydrogen bonding potential, which is responsible for most of the 5'-$^3$H KIE observed in PNPs and thymidine phosphorylase (Birck and Schramm, 2004). For *S. pneumoniae* MTAN the calculation predicted a 5'-$^3$H$_2$ KIE of 1.00 (the product of 5'-pro-R and 5'-pro-S hydrogen isotope effects). The 5'-pro-R and 5'-pro-S hydrogens behave differently to give isotope effects of 1.022 and 0.98 respectively. The normal isotope effect for the 5'-pro-R hydrogen is due to hyperconjugation between lone pair of sulphur and its σ* antibonding orbital. For the 5'-proS hydrogen the inverse isotope effect is due to the change in hyperconjugation from the sigma bond of the C5'-H5' proS hydrogen to the antibonding orbital of C4'-C5'. Freezing of the torsional angle upon binding and during the transition state gives rise to the observed 5'-$^3$H KIE.

Ribose hydroxyls and the catalytic rate of *S. pneumoniae* MTAN. The transition state for *S. pneumoniae* MTAN has unprotonated adenine as the leaving group, uncoupling activation of the leaving group from N-glycosidic bond loss. Transition state analysis, mutation studies and kinetics of substrate analogues for *E. coli* MTAN have demonstrated the importance of ribose hydroxyls in catalysis. Mutation of Glu174 to Ala or Gln completely abolishes the catalytic activity in *E. coli* MTAN. Further 3'-deoxy-MTA is not a substrate whereas 2'-deoxy-MTA retains 85% of its catalytic activity. These studies imply that ionization of 3'-OH by Glu174 may be essential for catalysis in *E. coli* MTAN. Ionization of the 3'-OH by Glu 174 releases electrons towards the purine ring, raising the pK$_a$ of N7, causing it to abstract a proton from the Asp197. Mutation of Asp197 completely abolishes catalytic activity in *E. coli* MTAN.

The crystal structure of *S. pneumoniae* MTAN with MT-ImmA shows complete conservation of active site residues supporting a similar mechanism. However the approximately 1000-fold decrease in catalytic efficiency by *S. pneumoniae* MTAN indicates an altered mechanism of transition state stabilization. The intrinsic KIE for 4'-$^3$H KIE of 1.015 for *S. pneumoniae* MTAN and 1.010 for *E. coli* MTAN supportionization of the 3'-hydroxyl by Glu174 for transition states of both enzymes. Unlike *E. coli* MTAN, the N7 in *S. pneumoniae* MTAN is not protonated, indicating a high energy transition state for *S. pneumoniae* MTAN. The $k_{cat}/K_m$ of *E. coli* MTAN for hydrolysis of MTA is ~1000 times greater than the $k_{cat}/K_m$ for *S. pneumoniae* MTAN, caused by the asynchronous loss of the N-ribosidic bond and proton donation to adenine.

Catalysis in *S. pneumoniae* MTAN is initiated by significant or complete polarization of the 3'-hydroxyl by Glu174, causing electron density to increase in the ribosyl group. The C1'-N9 bond strength weakens due to increased occupancy of σ*(C1'-N9) antibonding orbital. Cleavage of the N-ribosidic bond is slow in the absence of leaving group activation in *S. pneumoniae* MTAN. In contrast, the combination of 3'-OH ionization combined with the protonation of N7 accelerates the catalysis in *E. coli* MTAN.

Related purine N-ribosyltransferases achieve transition state with a neutral purine leaving group because of N7 protonation and a cationic ribooxacarbenium ion. In *S. pneumoniae* MTAN, the leaving group adenine is anionic at the transition state. To compensate, the ribosyl becomes a charge neutral but strongly polarized zwitterion, anionic at the 3'-OH and cationic at C1'. In both mechanisms, the net charge difference between the ribosyl group and the leaving group is the same.

Conclusion

*S. pneumoniae* MTAN has a fully dissociative S$_N$1 mechanism. The leaving group adenine is anionic at the transition state and therefore *S. pneumoniae* MTAN has a high energy transition state compared to the transition state of closely related *E. coli* MTAN. To achieve leaving group separation, the 3'-hydroxyl is deprotonated or strongly polarized at the transition state to form a zwitterionic ribosyl group. The dissociative transition state for *S. pneumoniae* MTAN predicts tighter binding of DADMe-Immucillins compared to Immucillins and this has been experimentally confirmed (Singh et al., 2006). Changing the dielectric field constant does not influence KIEs. van der Waal interactions between catalytic site residues and the transition state increases the 1'-$^3$H KIE and does not explain computational anomaly of large KIE at this site. A general conclusion is that perturbation (deprotonation, formation of carbocation, rotation of torsion angles) in any part of the molecule influences all other atoms and is manifested in alterations in the isotope effects.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:
1. A method of screening for an inhibitor of a 5'-methylthioadenosine/S-adenosylhomocysteine nucleosidase (MTAN) having 5'methylthioadenosine and S-adenosylhomocysteine substrates, the method comprising the steps of:
   (i) measuring kinetic isotope effects on the MTAN catalyzed hydrolysis of 5'-methylthioadenosine to obtain the MTAN transition state structure, wherein the MTAN transition state comprises the structure

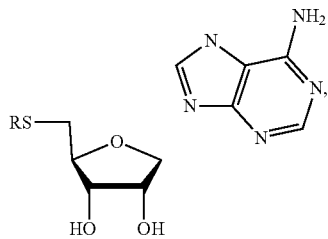

where R is CH$_3$ or homocysteine;
(ii) determining the molecular electrostatic potential at the van der Waals surface computed from the wave function of the MTAN transition state and the geometric atomic volume of the MTAN transition state;
(iii) obtaining a chemically stable compound that resembles the molecular electrostatic potential at the van der Waals surface computed from the wave function of the MTAN transition state and the geometric atomic volume of the MTAN transition state,
wherein the compound comprises a moiety resembling the molecular electrostatic potential surface of the ribosyl group at the transition state,
wherein the moiety resembling the molecular electrostatic potential surface of the ribosyl group at the transition state is a substituted iminoribitol, a substituted hydroxypyrrolidine, a substituted pyridine or a substituted imidazole,
wherein the compound comprises an atomic moiety inserted into the inhibitor providing a compound that mimics the C1'-N9 ribosyl bond distance of a 5'-methylthioadenosine or S-adenosylhomocysteine at the transition state,
wherein the atomic moiety inserted into the inhibitor that provides a compound that mimics the C1'-N9 ribosyl bond distance of a 5'-methylthioadenosine or S-adenosylhomocysteine at the transition state is a methylene, a substituted methylene, an ethyl, or a substituted ethyl bridge, and
wherein the compound comprises a purine moiety or a deazapurine moiety; and
(iv) testing the compound for inhibitory activity to MTAN by determining if the compound inhibits MTAN-catalyzed hydrolysis of 5'-methylthioadenosine to generate adenine and 5-methylthioribose or if the compound inhibits MTAN-catalyzed hydrolysis of S-adenosylhomocysteine to generate adenine and S-ribosylhomocysteine,
wherein a compound that inhibits MTAN-catalyzed hydrolysis of 5'-methylthioadenosine or S-adenosylhomocysteine is an inhibitor of MTAN.

2. The method of claim 1, wherein the compound comprises a purine moiety.

3. The method of claim 1, wherein the compound comprises a deazapurine moiety.

4. The method of claim 1, wherein the compound comprises a moiety resembling methylthioribose at the transition state.

5. The method of claim 1, wherein the compound comprises a moiety resembling S-homocysteinyl ribose at the transition state.

6. The method of claim 1, wherein the substituent is an aryl- or alkyl-substituted thiol group.

7. The method of claim 6, wherein the substituent is a methylthiol group.

8. The method of claim 1, wherein the compound exhibits a similarity value S$_e$ to the transition state greater than to either substrate.

9. The method of claim 1, wherein the 5'-methylthioadenosine/S-adenosylhomocysteine nucleosidase is from a bacterial pathogen.

10. The method of claim 9, wherein the bacterial pathogen is a mammalian pathogen.

11. The method of claim 10, wherein the mammalian pathogen is an *E. coli*, a *Staphylococcus* sp., a *Streptococcus* sp., an *Enterococcus* sp., a *Bacillus* sp., *Bifidobacterium bifidum*, a *Lactobacillus* sp., *Listeria monocytogenes*, a *Nocardia* sp., *Rhodococcus equi*, *Erysipelothrix rhusiopathiae*, *Corynebacterium diptheriae*, *Propionibacterium acnes*, an *Actinomyces* sp., a *Clostridium* sp., a *Mobiluncus* sp., a *Peptostreptococcus* sp., a *Neisseria* ap., *Moraxella catarrhalis*, a *Veillonella* sp. *Actinobacillus actinomycetemcomitans*, *Acinetobacter baumannii*, *Bordetella pertussis*, a *Brucella* sp., a *Campylobacter* sp., a *Capnocytophaga* sp., *Cardiobacterium hominis*, *Eikenella corrodens*, *Francisella tularensis*, a *Haemophilus* sp., *Helicobacter pylori*, *Kingella Kingae*, a *Pasteurella*, a *Klebsiella* sp., an *Enterobacter* sp., a *Proteus* sp., a *Salmonella* sp., a *Shigella* sp., *Serratia marcescens*, a *Yersinia* sp. an *Aeromonas* sp., *Plesiomonas shigelloides*, a *Vibrio* sp., an *Acinetobacter* sp., a *Flavobacterium* sp., a *Pseudomonas* sp., a *Burkholderia* sp., a *Xanthomonas* sp., a *Bacteroides* sp., a *Prevotella* sp., a *Fusobacterium* sp., *Spirillum minus*, a *Borrelia* sp., *Bartonella henselae*, a *Chlamydia* sp., a *Chlamydophila* sp., *Coxiella burnetii*, an *Ehrlichia* sp., an *Anaplasma* sp., a *Legionella* sp., a *Leptospira* sp., a *Mycobacterium* sp., a *Rickettsia* sp., an *Orientia* sp., or *Treponema pallidum*.

12. The method of claim 10, wherein the mammalian pathogen is an *E. coli*.

13. The method of claim 10, wherein the mammalian pathogen is a *Streptococcus pneumoniae*.

14. The method of claim 1, wherein the 5'-methylthioadenosine/S-adenosylhomocysteine nucleosidase transition state comprises properties as set forth in Table 2 or Table 7.

15. The method of claim 1, wherein the 5'-methylthioadenosine/S-adenosylhomocysteine nucleosidase transition state is highly dissociative with very low bond order to the leaving group, no significant bond order to the attacking water nucleophile and the ribosyl moiety to have significant oxacarbenium ion character.

16. The method of claim 1, wherein a reaction catalyzed by 5'-methylthioadenosine/S-adenosylhomocysteine nucleosidase undergoes a dissociative (D$_N$*A$_N$) (S$_N$1) mechanism with little involvement of the leaving group or participation of the attacking nucleophile at the transition state, causing the transition state to have significant ribooxacarbenium ion character.

17. The method of claim 1, wherein the 5'-methylthioadenosine/S-adenosylhomocysteine nucleosidase transition state has a small bond order to the leaving group and little participation of the attacking nucleophile.

18. The method of claim 1, wherein the 5'-methylthioadenosine/S-adenosylhomocysteine nucleosidase transition state exhibits significant cationic character with low Pauling bond order to the leaving group and insignificant bond order to the attacking nucleophile.

19. The method of claim 1, wherein the 5'-methylthioadenosine/S-adenosylhomocysteine nucleosidase transition state is a dissociative transition state with oxacarbenium ion character.

20. The method of claim 1, wherein the 5'-methylthioadenosine/S-adenosylhomocysteine nucleosidase transition inhibitor resembles 5'-methylthioadenosine (MTA) with riboxacarbenium features in the ribosyl group and elevated $pK_a$ values in the leaving group adenine analogue.

* * * * *